(12) United States Patent
Robinson

(10) Patent No.: US 9,239,321 B2
(45) Date of Patent: Jan. 19, 2016

(54) ADVANCED EGG BREAKING SYSTEM

(75) Inventor: Jonathan D. Robinson, Grand Blanc, MI (US)

(73) Assignee: FPS Food Processing Systems, B.V., Amstelveen (NL)

(*) Notice: Subject to any disclaimer, the term of this patent is extended or adjusted under 35 U.S.C. 154(b) by 681 days.

(21) Appl. No.: 13/636,804

(22) PCT Filed: Mar. 24, 2011

(86) PCT No.: PCT/US2011/029782
§ 371 (c)(1),
(2), (4) Date: Sep. 24, 2012

(87) PCT Pub. No.: WO2011/119825
PCT Pub. Date: Sep. 29, 2011

(65) Prior Publication Data
US 2013/0008475 A1  Jan. 10, 2013

Related U.S. Application Data

(60) Provisional application No. 61/317,064, filed on Mar. 24, 2010.

(51) Int. Cl.
*A01K 43/00* (2006.01)
*G01N 33/08* (2006.01)
(Continued)

(52) U.S. Cl.
CPC ............... *G01N 33/08* (2013.01); *A01K 43/00* (2013.01); *A01K 43/04* (2013.01); *A47J 43/145* (2013.01); *A01K 43/005* (2013.01)

(58) Field of Classification Search
CPC ..... A01K 43/00; A01K 43/005; A01K 43/04; G01N 33/08; A47J 43/14; A47J 43/145
USPC ............ 209/10, 510, 511, 576, 588; 119/6.8; 422/63, 65, 527, 552
See application file for complete search history.

(56) References Cited

U.S. PATENT DOCUMENTS 1,764,802 A * 6/1930 Mahlstedt ................. 99/500
3,532,144 A  10/1970 Halvorson
(Continued)

FOREIGN PATENT DOCUMENTS

JP  59151007 A  8/1984
JP  07209209 A  8/1995
(Continued)

OTHER PUBLICATIONS

International Search Report, PCT/US2011029782—FPS Food Processing Systems, B.V., 8 pages, dtd. Sep. 8, 2014.

*Primary Examiner* — Joseph C Rodriguez
(74) *Attorney, Agent, or Firm* — Dinsmore & Shohl LLP; Douglas J. McEvoy

(57) ABSTRACT

An egg transfer system for providing automated inspection and tracking of eggs prior to entering an egg breaker, as well as broken egg contents following breaking, and in which the transfer system includes a series of processing and inspection component interfacing with a central processor for grading and segregating the eggs into one of a number of classes including removal eggs. Removal gates are provided at intermediate locations of the egg transfer system, prior to the egg breakers, and are associated with removal of varying classes of eggs. The central processor interfaces with the various stations in order to assemble a dedicated data packet of egg related data which is assigned to a progressing location on the egg conveyor upon which a specified egg is located, and which can further include the central processor assigning the data packet to a location subsequent to the breakers holding specified shell egg contents. At least one, and typically two, manual removal locations are additionally provided, such as associated with the intermediate egg detection and removal station as well as the post-breaker station.

20 Claims, 50 Drawing Sheets

(51) Int. Cl.
*A01K 43/04* (2006.01)
*A47J 43/14* (2006.01)

(56) References Cited

U.S. PATENT DOCUMENTS

| | | | |
|---|---|---|---|
| 4,321,864 A * | 3/1982 | Willsey | 99/500 |
| 4,519,505 A | 5/1985 | Thomas | |
| 4,805,778 A * | 2/1989 | Nambu | 209/3.3 |
| 5,017,003 A | 5/1991 | Keromnes et al. | |
| 5,277,320 A * | 1/1994 | Corkill et al. | 209/511 |
| 5,321,491 A | 6/1994 | Summers et al. | |
| 5,325,768 A | 7/1994 | van den Hazel | |
| 5,460,083 A | 10/1995 | Hutchinson et al. | |
| 5,483,872 A | 1/1996 | Nield | |
| 5,527,550 A | 6/1996 | Miles et al. | |
| 5,634,397 A | 6/1997 | Hutchinson et al. | |
| 5,858,434 A | 1/1999 | Thomas | |
| 6,032,311 A * | 3/2000 | Nambu | 15/3.15 |
| 6,145,668 A | 11/2000 | DePauw et al. | |
| 6,149,375 A | 11/2000 | Hebrank | |
| 6,213,709 B1 | 4/2001 | Hebrank | |
| 6,224,316 B1 | 5/2001 | Hebrank et al. | |
| 6,234,320 B1 * | 5/2001 | Hebrank | 209/510 |
| 6,427,844 B2 | 8/2002 | Hebrank | |
| 6,433,293 B1 | 8/2002 | Bollinger et al. | |
| 6,446,784 B1 | 9/2002 | Veldhuizen et al. | |
| 6,506,570 B1 * | 1/2003 | Phelps | 435/7.21 |
| 6,527,498 B2 | 3/2003 | Chalker, II et al. | |
| 6,532,064 B1 | 3/2003 | Hearn et al. | |
| 6,883,528 B2 * | 4/2005 | Kuhl | 134/72 |
| 7,041,439 B2 * | 5/2006 | Phelps et al. | 435/4 |
| 7,111,740 B2 | 9/2006 | Ogawa et al. | |
| 7,474,392 B2 | 1/2009 | Van Soest | |
| 7,573,566 B2 | 8/2009 | Hebrank et al. | |
| 7,611,277 B2 | 11/2009 | Hebrank et al. | |
| 7,988,792 B2 * | 8/2011 | Cavallaro et al. | 134/57 R |
| 8,235,003 B2 * | 8/2012 | Hebrank et al. | 119/6.8 |
| 8,330,809 B2 * | 12/2012 | Thomas | A01K 43/00 348/89 |
| 8,339,587 B2 * | 12/2012 | Hebrank | 356/53 |
| 8,610,018 B2 * | 12/2013 | Phelps | A01K 45/00 119/6.8 |
| 2005/0120964 A1 | 6/2005 | Moayeri et al. | |
| 2008/0292758 A1 | 11/2008 | Kristensen et al. | |
| 2009/0217826 A1 | 9/2009 | Kristensen et al. | |
| 2011/0189720 A1 * | 8/2011 | Goldstein et al. | 435/29 |
| 2012/0148714 A1 * | 6/2012 | Holst | A47J 43/145 426/298 |
| 2013/0008475 A1 * | 1/2013 | Robinson | A47J 43/145 134/115 R |
| 2013/0319335 A1 * | 12/2013 | Hebrank | A01K 43/00 119/6.8 |
| 2014/0261189 A1 * | 9/2014 | Chait | A01K 43/00 119/6.8 |

FOREIGN PATENT DOCUMENTS

| | | |
|---|---|---|
| JP | 11-287763 A | 10/1999 |
| JP | 2004-344040 A | 12/2004 |
| JP | 2006-018420 A | 1/2006 |
| WO | WO-2007-066724 A1 | 6/2007 |
| WO | WO-2007133063 A2 | 11/2007 |

* cited by examiner

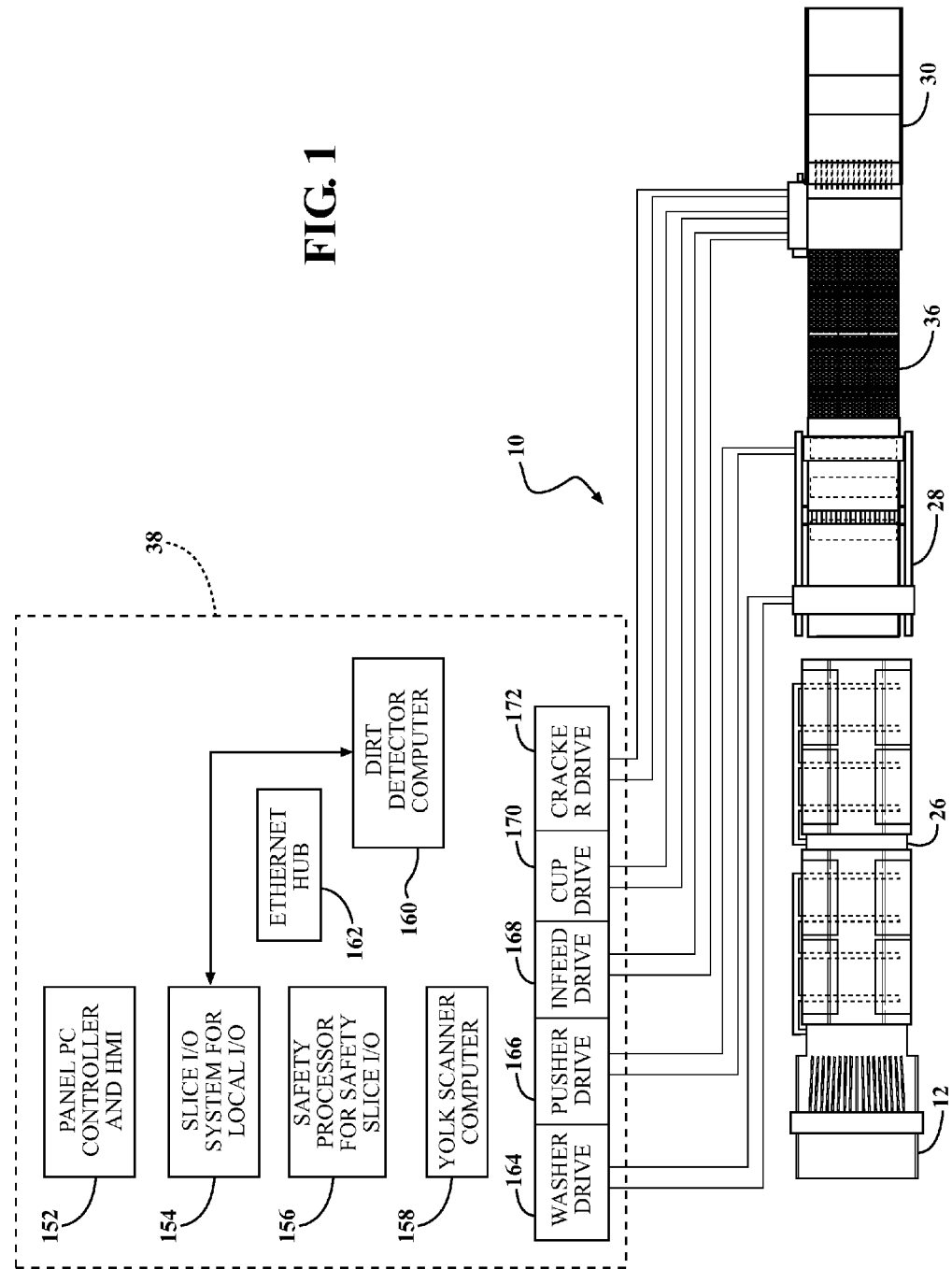

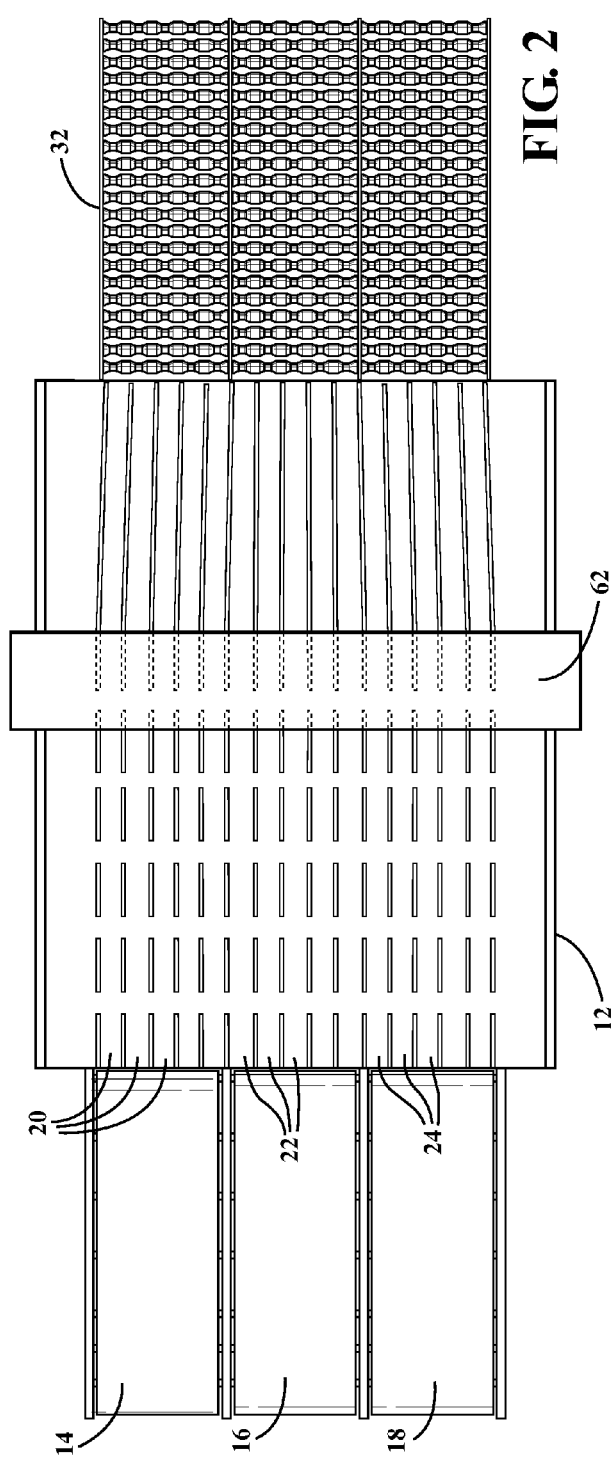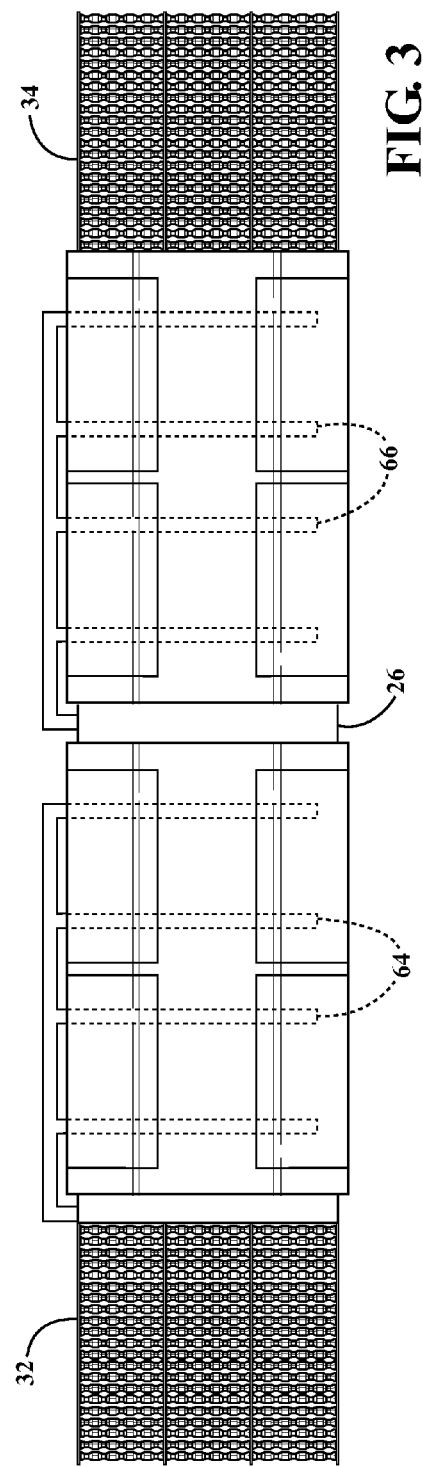

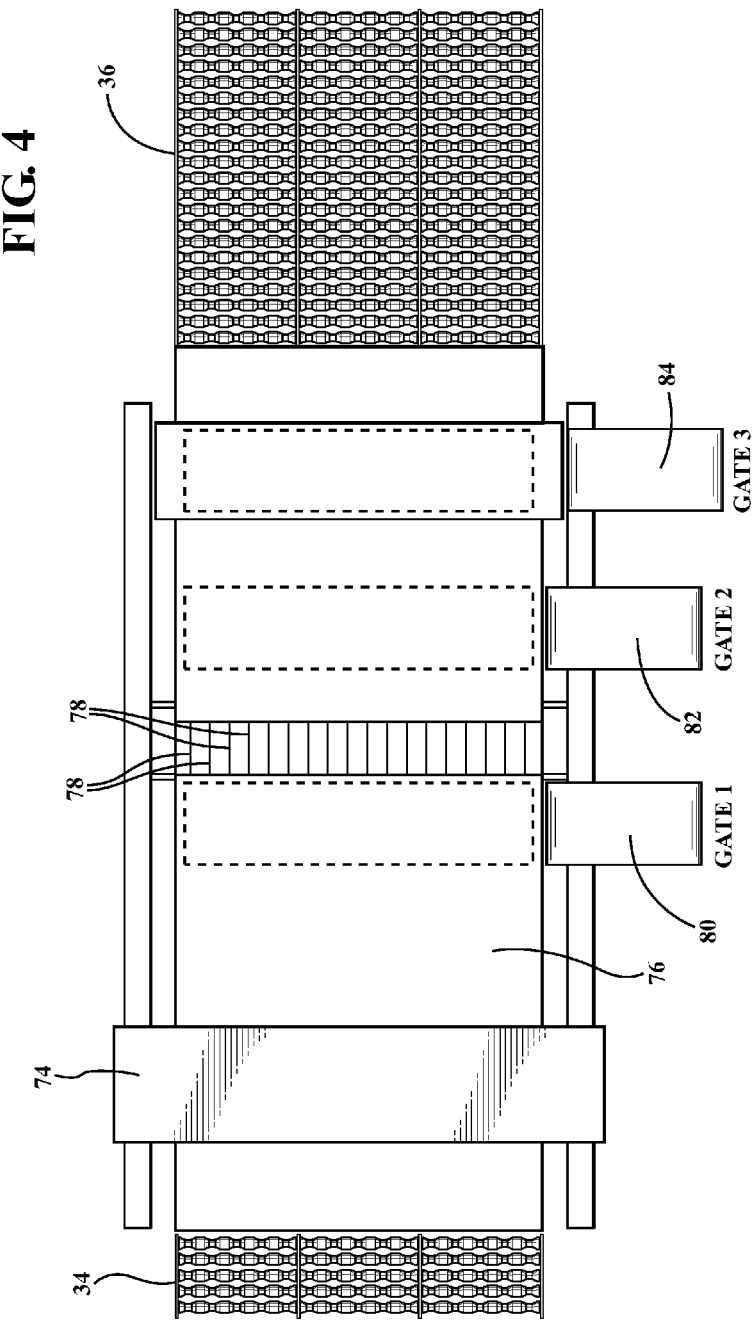

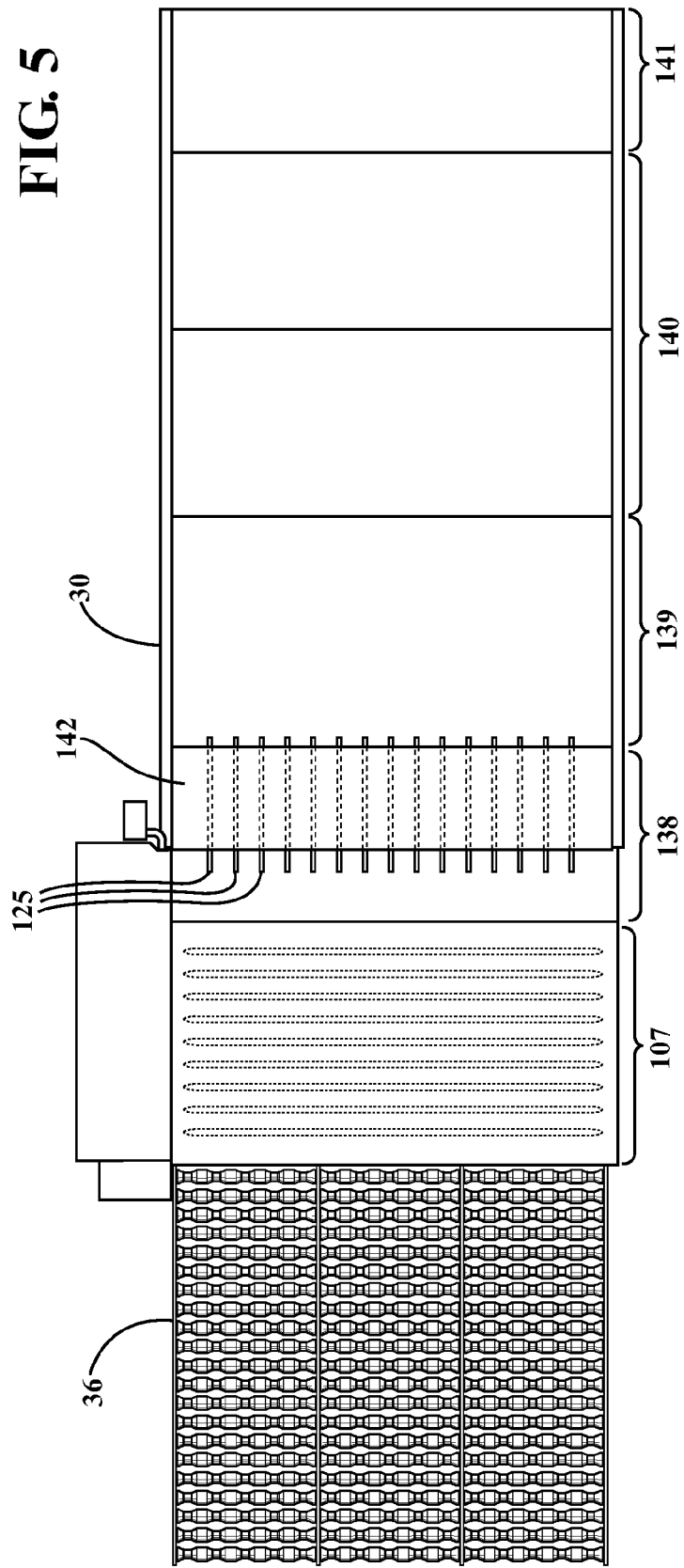

FIG. 21

Scale Diagnostics — 186

IDLE/STOPPED

Information | Service | Calibration History | Calibrate

| | 1 | 2 | 3 | 4 | 5 | 6 | 7 | 8 |
|---|---|---|---|---|---|---|---|---|
| Serial No. | 24/23 | 27/45 | 27/46 | 27/47 | 27/48 | 27/49 | 27/50 | 27/ |
| Version | 918 | 918 | 918 | 918 | 918 | 918 | 918 | 918 |
| Manufacture Date | 11/12/08 | 06/2/09 | 06/2/09 | 06/2/09 | 06/2/09 | 06/2/09 | 06/2/09 | 06/3 |
| Installation Date | 0/0/000 | 0/0/000 | 0/0/000 | 0/0/000 | 0/0/000 | 0/0/000 | 0/0/000 | 0/0/ |
| Date | 7/27/09 | 6/2/09 | 6/2/09 | 6/2/09 | 6/2/09 | 6/2/09 | 6/2/09 | 6/2/ |
| Weight | 100 | 50 | 50 | 50 | 50 | 50 | 50 | 50 |
| Scale Factor | 921.4 | 947.3 | 930.9 | 939.7 | 894.6 | 894.6 | 943.8 | 949 |
| Tare | 183.7 | 183.6 | 177 | 177.7 | 180.8 | 180.8 | 183.6 | 184 |
| By | xx | nw | nw | nw | nw | nw | nw | nw |

188 — Serial No.
190 — Version
192 — Manufacture Date
194 — Installation Date
196 — Date
198 — Weight
200 — Scale Factor
202 — Tare
204 — By

Preventative Maintenance Log

| Frequency | Service Activities | Task(s) | Part Number | Part Manual | Manual Page | Quality | Notes | Current Odometer 5 |
|---|---|---|---|---|---|---|---|---|
| Daily | Screens | Inspect, Clean | | | | | | Due in:7.9 Hours |
| Daily | Holding Tanks and Coils | Inspect, Clean | | | | | | Due in:7.9 Hours |
| After CIP | Inspect and Clean Spray Orifices (Nozzles) | Inspect, Clean | | | | | | Due in:After CIP |
| After CIP | Inspect Egg Oiler | Inspect | | | | | | Due in:After CIP |
| Weekly | Shift Washer Brushes | Adjust | | | | | | Due in:39.9 Hours |

IDLE/STOPPED  
2:08:47 1:0:0:0

324

ADVANCED EGG BREAKING SYSTEM

CROSS-REFERENCE TO RELATED APPLICATIONS

This application is the U.S. National Phase of PCT/US2001/029782 filed Mar. 24, 2011, which claims the benefit of U.S. Provisional Application 61/317,064 filed on Mar. 24, 2010, the disclosures of which are incorporated by reference herein in their entirety.

FIELD OF THE INVENTION

The present invention generally addresses a system for providing automated inspection, removal and tracking of eggs advancing along an egg conveying apparatus and prior to an egg breaking stage. More specifically, the present invention discloses a system for providing inspection, tracking and removal of selected eggs, the latter feature especially desirable in situations where eggs of a quality exceeding that minimally necessary for the breaker can be reclaimed from the main conveyor for use such as in higher demand or more lucrative in shell applications.

BACKGROUND OF THE INVENTION

The prior art is well documented with examples of egg transfer and processing machinery, such as which are located within industrial egg laying facilities and which are communicated by egg conveying belts extending from the various hen laying houses. Typical egg transfer systems include each of egg orienting, washing, and grading operations, as well as optional egg breaking in which the previously shelled eggs are reduced to yolk and albumen components for given applications, and as an alternative to other applications in which it is desirous to package the shell eggs.

Shortcomings associated with known egg transfer devices include the lack of an integrated processor control interfacing in cumulative fashion with each step of the egg transfer and processing operations, such as for constructing dedicated egg data profiles for a specified conveyor location. Additional shortcomings include the inability to effectively differentiate certain grades (including weight, color and the like) off shell eggs prior to entering the breakers, and in particular instances where it is desirable to remove certain types of eggs to be utilized in packaging operations and as opposed to being reduced to yolk and albumen components.

SUMMARY OF THE INVENTION

The present invention discloses an egg transfer system for providing automated inspection and tracking of advancing eggs prior to entering an egg breaker as well as subsequent tracking of broken egg contents. The transfer system includes a series of processing and inspection component interfacing with a central processor for grading and segregating the eggs into one of a number of classes including removal eggs. An egg accumulator communicates a series of conveyors extending from the various laying houses for delivery of a plurality of eggs. The accumulator may also include individual sub-pluralities of lanes dedicated to specified laying houses which may be independently processor controlled.

The accumulator in turn delivers the accumulated flow of eggs to one or more of an egg washer, a pre-breaker scanner, a crack detection unit, a weighing unit, an egg counter and a post breaker scanner. A plurality of strategically positioned removal gates are provided at intermediate locations of the egg transfer system, prior to the egg breakers, and which are intended to assist in the removal of specific types of eggs. In one variant, a first gate is provided for removing leaking or significantly defective eggs, a second gate for dirty eggs to be rerouted back to a preceding egg washer for rewashing, and a third gate for rerouting desirable shell eggs from a conveyor leading to the breaker for reclamation and use in alternate shell applications.

The central processor interfaces with the various stations in order to assemble a dedicated data packet of egg related data which is assigned to a progressing location on the egg conveyor (this typically consisting of interconnecting spool bar sections) upon which a specified egg is located. The central processor further includes the feature of assigning a data packet to a location subsequent to the breakers which holds specified shell egg contents (e.g. yolk cup and underneath positioned albumen tray). At least one, and typically two, manual removal locations are provided at both an intermediate (pre-breaker) egg detection and removal station, as well as the post-breaker removal station at which targeted air circulators are provided for assisting the individual sense of smell in detecting any rotten liquid egg contents indicative of a contaminated batch.

The present invention also discloses a processor control "smart box" subassembly which is capable of being retrofit installed with any existing egg transfer assembly including any one or more of the accumulating, washing, inspection/removal, and breaking stations. In this application, the necessary sensors and/or controller interfaces are installed upon the various transfer stations and are communicated to such as an Ethernet hub incorporating the any combination of controller panels and visual screen displays (such as further with touch screen capability). In this fashion, the retrofit version of the control subassembly again provides both the assembly of data profiles associated with each egg conveying location, as well as the ability to adjust (such as speed) the operational parameters associated with each station and such as in response to detected conditions.

BRIEF DESCRIPTION OF THE DRAWINGS

Reference will now be made to the attached drawings, when read in combination with the following detailed description, wherein like reference numerals refer to like parts throughout the several views, and in which:

FIG. 1 is an overall schematic view of an egg transfer system and incorporating a combination of pre-breaker functions including vision/crack detection, weighing, selected egg removal, candling and counting along with breaker and post breaker yolk and albumen scanning and liquid removal;

FIG. 2 is a sectional illustration of an inlet accumulator/organizer subassembly of the egg transfer system, such as which is arranged in communication with egg feeds originating from multiple hen laying houses and illustrating mechanical guides for influencing eggs from a given house into assigned lane positions;

FIG. 3 is a sectional view of an egg washer succeeding the accumulator and through which the pre-segregated eggs are maintained in position during passage through the washer and are further tracked according to process parameters including, without limitation, wash/rinse temperatures, ph level, conductivity, detergent level and time in wash;

FIG. 4 is an enlarged sectional view of a post washer and pre breaker egg inspection and removal subassembly which combines a series of inspection, detection, weighing, tracking and removal components and including each of vision inspection, crack lane detection and lane assignment, weighing and targeted egg removal, and counting;

FIG. 5 is a further succeeding illustration of a downstream egg breaker sub assembly and in which the tracked and data assigned eggs being fed into the egg breaker, following the manual removal/candling and egg counting in FIG. 4, and which further provides the several post-breaker functions for inspecting and empting yolk and albumen as well as attending to shell waste removal;

FIG. 21 illustrates a control screen used to fetch and view information stored on digital scales also associated with the egg inspection and removal subassembly and including serial number, firmware version, manufacture date, installation date, calibration date, calibration weight, calibration factor, tare and initials of the individual who last calibrated the scale;

FIG. 33 is a control screen used to display preventative maintenance tasks loaded on a control computer in the form of site customizable spreadsheets, which allow the control software to inform operators of preventative maintenance tasks due and to track and log the completion of tasks as well as the operator completing the work and operator notes;

DETAILED DESCRIPTION OF THE PREFERRED EMBODIMENTS

Figure 6:
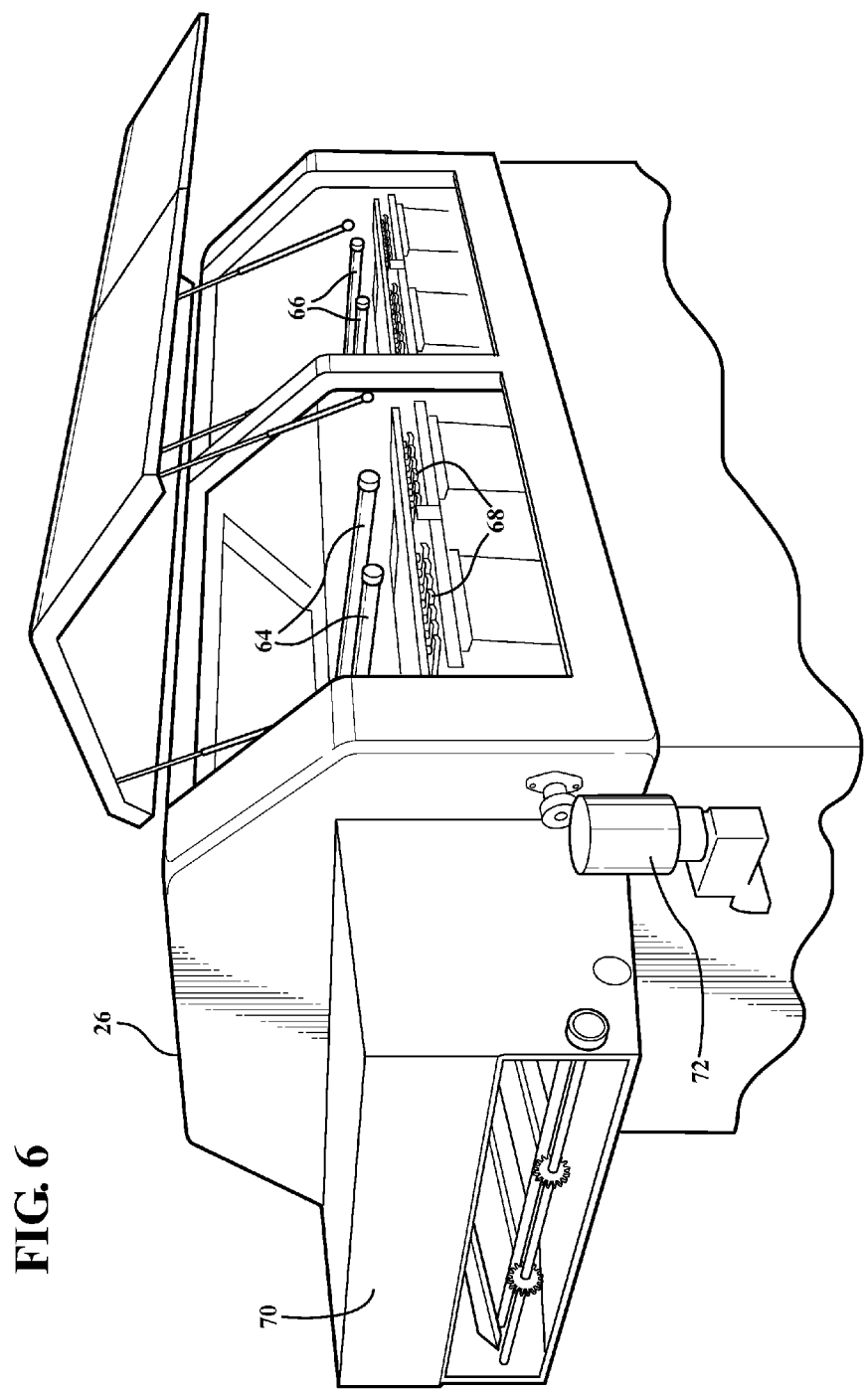
FIG. 6 is a perspective view of a dual station washer such as depicted in FIG. 3 and which further shows the arrangement of the overhead sprayer bars in relation to an underneath positioned conveyor, as well as depicting an inlet side and accumulator interfacing component.

As previously described, the present invention discloses an egg transfer system, such as utilized in an industrial egg laying and processing facility, and which generally addresses the need for establishing automated identification and tracking of eggs, such as during handling operations preceding an egg breaking stage. As will be described in detail below, the egg transfer system incorporates processor technology which interfaces with each interconnecting station and which assists in assembling a data file associated with each identified and advancing egg position in order to both track and assemble data of individual egg properties and process parameters throughout the entire orientation, washing, inspection/removal and breaking processes. The processor control aspects further interface with a midpoint located egg inspection and removal subassembly which enables eggs to be selectively rerouted from the main transfer system out through one or more gates for varying purposes such as re-washing, removing damaging or leaking eggs or selective removal of superior quality eggs.

The feature of selective egg removal from the transfer assembly at a point preceding the egg breaker is especially desirable in situations where eggs of a quality exceeding that minimally necessary for the breaker (such as specialized colored and larger sized eggs) can be reclaimed from the system prior to being sent to the egg breakers. The rescue of such desirable eggs allowing for their more profitable use in higher market demand and/or more lucrative in shell applications and while ensuring that only eggs of requisite condition are sent to the breakers for reduction to yolk and albumen components.

The above stated, and referring to FIG. 1, an overall schematic view is generally illustrated at 10 of an egg transfer system. The system 10 is typically located within an industrial egg laying operation and incorporates a plurality of components or stations (hereinafter termed subassemblies) for washing, grading, and handling raw eggs from the varying laying houses.

As further depicted in the schematic view of FIG. 2, preceding the initial egg accumulator (or orientor) 12 are a plurality of individual belts 14, 16 and 18 which are intended to signify different laying houses (not shown) associated with the installed location of the egg transfer system. As is known, the laying houses each include a dedicated network of conveyors and feeders extending from the industrial laying pens, and in order that eggs laid by the hens are routed to the belts 14, 16 and 18 for subsequently delivery to the accumulator 12. It is also understood that the accumulator 12 for purposes of the disclosure can be substituted by any other form of inlet equipment or sourcing for direct in-feed of eggs to the overall system.

The accumulator 12 defines a first or inlet subassembly associated with the overall egg transfer system 10 and, as further depicted in schematic fashion in FIG. 2, a plurality of individually defined lanes and which, depending upon the size and orientation of the inlet feeder belts 14, 16, 18, define individual sub-pluralities 20, 22, and 24 of lane entry positions for feeding the eggs delivered from the respective laying houses. As will be subsequently described, the associated processor control aspects assign specified lane and spool positions to given eggs originating from a given laying house and throughout the egg transfer system.

The conveyors are each moved using such as an electric motor (servo) with a positioning device which defines where the eggs are as they are moved through the entire system. Beyond the arrangement depicted, it is understood that any other scalable arrangement can be employed, such as using fewer or more than the three laying houses depicted and/or either more or fewer lanes provided per laying house. It is also envisioned that the eggs provided along the in feed belts 14, 16 and 18 do not necessarily need to originate from laying houses, but could rather be provided from any number of offline suppliers (e.g. eggs not communicated from a facility located laying house but rather introduced in bulk after being transported from a remote location). Beyond that described, it is envisioned that any laying house or offline supplier can be assigned to any position or number of positions defined in the computer system.

As is further described in succeeding illustrations FIGS. 2-5, the transfer system 10 depicted in the non-limiting embodiment includes, in addition to the inlet accumulator 12, an egg washer subassembly 26, egg inspection and removal subassembly 28, and an egg breaker 30.

Interconnecting each of the accumulator 12, washer 26, inspection/removal 28 and breaker 30 subassemblies are individual sections of spool bars, as further shown at 32 (FIGS. 2-3) extending between the accumulator 12 and washer 26, at 34 (FIGS. 3-4) extending between washer 26 and inspection/removal subassembly 28 and, at 36 (FIGS. 4-5) extending between the inspection/removal subassembly 28 and breaker 30. The spool bar sections 32, 34, 36 each consist of a plurality of parallel aligned and spaced apart spool bars, specified ones of which are powered/rotated and, in combination with any adjoining and free-wheeling/rotating spool bars, operate to advance eggs between the subassemblies. The spool bars are of a given width and configuration which correspond to number and placement of lanes (such as fifteen) originating with the accumulator 12 and extending to the breaker 30.

As is further schematically referenced in FIG. 1, a processor/control sub-system 38 includes a plurality of input communication lines fed by sensors mounted at specified locations within each of the associated egg transfer subsystems, and in addition to a plurality of output lines (physical and/or wireless) connecting to servo-motors associated with each of the transfer subassemblies as well as inlet feed belts 14, 16 and 18 and interconnecting spool sections 32, 34 and 36. Illustrated in FIG. 1 are inlet lines 42 (washer drive), 44 (pusher drive), 46 (infeed drive), 48 (cup drive) and 50 (cracker drive). Corresponding outlet lines 52, 54, 56, 58 and 60 extend from servo motors (not shown) mounted to the driving components incorporated into each piece of equipment in paired fashion with each of the above referenced inlet lines 42, 44, 46, 48 and 50.

In this fashion, an aggregating series of input parameters are fed to the processor 38 and which progressively assemble the data packets of information beginning with each egg placement location established at lane entry positions 20, 22, 24 interfacing with the laying house belts 14, 16 and 18 and terminating in the yolk cup/albumen trays associated with each remaining egg passing through the breakers. The corresponding output lines communicate signals from the processor/controller 38 to the servo drives associated with the individual components in order to adjust various parameters (including but not limited to operating speed) associated with the laying house belts, transfer subassemblies, and interconnecting spool sections.

It should also be noted that, additional to the hardwiring scheme illustrated in FIG. 1, processor connections to the in-feed laying house belts 14, 16, 18, the accumulator 12, and washer 26 are understood to either be routed through additional wiring extending from the egg inspection/removal subassembly 28 and/or breaker subassembly 30 or, alternatively or additionally, additional wiring (or wireless connections) can be incorporated into the communication architecture between the controller 38 and these other components in order to selectively or simultaneously adjust the operating parameters of each.

Referring again to FIG. 2, each of the laying houses 14, 16 and 18 include mechanical guides for influencing eggs from a given house into assigned lane positions. As shown in FIG. 2, the non-limiting example shown includes the accumulator 12 exhibiting 1-3 entry lane positions (identified again at 20) for laying house 14, positions 4-10 (also lanes 22) for laying house 16 and positions 11-15 (also lanes 24) for laying house 18.

Alternate to laying houses it is also envisioned that the accumulator 12 can be communicated with multiple offline suppliers, and to which any position or number of positions can be defined by the associated computerized processor system. The central processor controller system see, again at 38 in FIG. 1 and as will be further described in reference to the succeeding illustrations FIGS. 19-51, precisely controls the flow of eggs, process parameters, and inspection properties of each egg through the entire transfer process, this being accomplished through the accretion of information assembled by the several successive inspection stations and which is compiled into a data packet associated with the specific egg at its dedicated conveyor position, again beginning at the point that the eggs are received at their respective lane entry positions from the laying houses 14, 16, 18 to the accumulator 12 and extending through their removal through each of the gates associated with the inspection/removal subassembly 28 or their eventual reduction in the breaker subassembly 30 to assigned yolk cups and albumen trays.

The purpose of the accumulator 12 is accumulate and orient the eggs into specific positions onto a conveyor that mechanically separates the eggs from each other through the entire process via the mechanical dividers or guides (at 62 in FIG. 2). Some or all of the individual spool bars incorporated into the interconnecting spool conveyor sections 32, 34 and 36 are again concurrently rotated utilizing an electric motor (servo), with the positioning technology incorporating subassembly specific located sensors and input lines extending to the processor 38 establishing a specific (and data assigned) advancing location for each egg as advanced through the transfer system, this also including that location being assigned to a yolk and albumen cup holder associated with post breaker operations.

Referring to FIG. 3, an enlarged sectional view is shown of the egg washer 26, succeeding the accumulator 12 as further depicted in the overall view of FIG. 1, and through which the pre-segregated eggs are maintained in position upon the interconnecting spool bar conveyor section 32. Reference is also made to FIG. 6 which illustrates a perspective view of a dual station washer 26 and which further shows the arrangement of overhead sprayer bars 64 (initial station) and 66 (succeeding station) in relation to a looped and underneath positioned conveyor (see individual sections 68). The washer 26 further depicts an inlet side 70 which connects to the spool bar section 32 depicted in FIG. 3. Also shown is a brush drive 72 with additional servo drives (not shown) being located at the removal subassembly 28 and such as which can be accessed by output line 52 schematically depicted in FIG. 1 in order to adjust the speed of the looped conveyor 68 within the washer in cooperation with or alternately from the inlet spool bar section 32 and outlet section 34.

During conveyance through the washer 26, the individual eggs (not shown) are tracked according to process parameters including without limitation wash/rinse temperatures, pH level, conductivity, detergent level and time in wash. As is further known, the purpose of the washer 26 is to clean the surface of the egg shell to an acceptable level for further processing. The ability to track washing parameters and egg shell inspection results can be used to optimize the parameters of the washing system to provide maximum throughput of eggs. The ability to provide processor based data tracking of the individual eggs, through the parameters identified, further can be used to determine if there are specific positions within the washer which are not performing correctly or if eggs from a given supplier may require different washing parameters, so as to again improve throughput.

Figure 9:
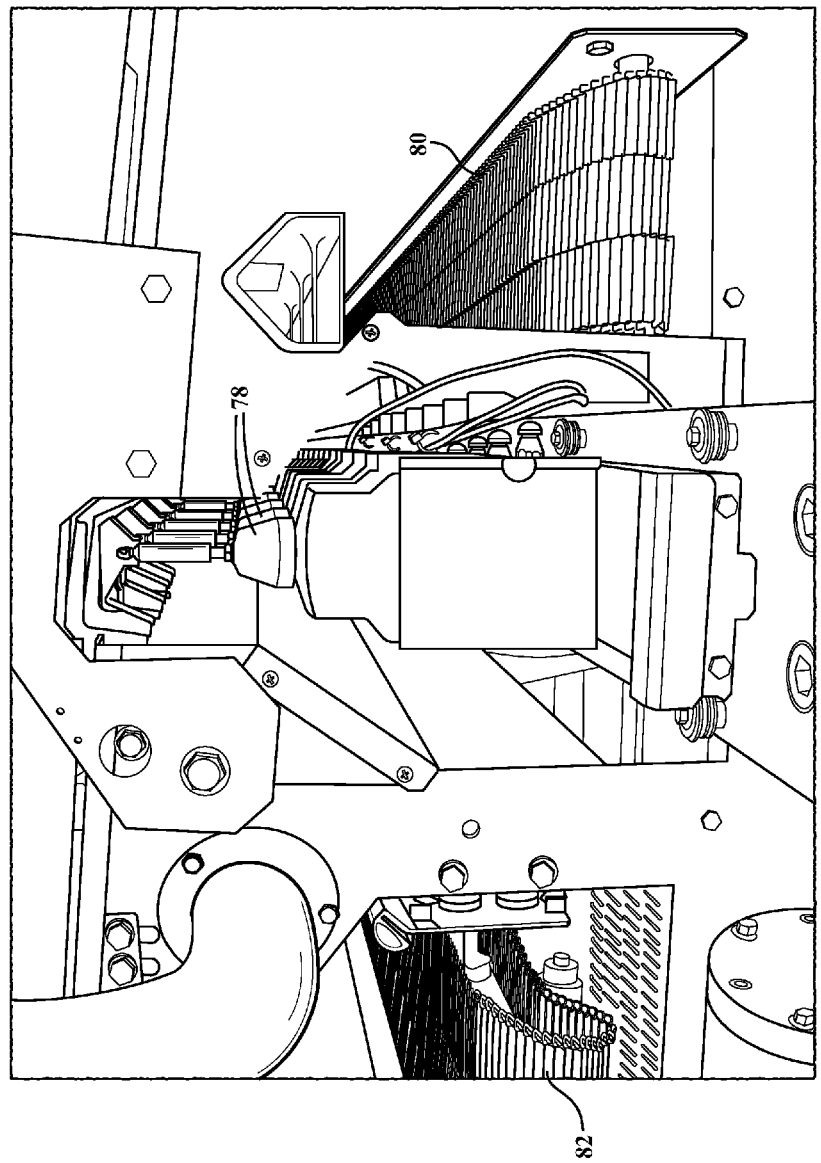
FIG. 9 is a side view of a plurality of digital weight scales associated with a succeeding station incorporated into the inspection and removal subassembly.

Referring to FIG. 4 (in cooperation with succeeding FIGS. 7-13) an enlarged schematic view is illustrated of the egg inspection/removal subassembly 28 which is interconnected by spool bar sections 34 and 36. As will be individually described in succession, the inspection/removal subassembly 28 incorporates a series of stations including, from an inlet end, a vision inspection station 74, a crack detection, segregation and data assignment station 76, weighing station (see as depicted by underneath located digital scales at 78 in FIG. 9), and a plurality of targeted and automated egg removal gates (see at 80, 82, and 84). Additional features including manual (station located) egg removal, as well as egg candling (rotating) and counting (via location identity sensors as depicted in FIG. 13) occur upon the outlet spool conveyor section 36 extending from the inspection/removal subassembly 28 prior to delivery to the breaker subassembly 30.

Figure 7:
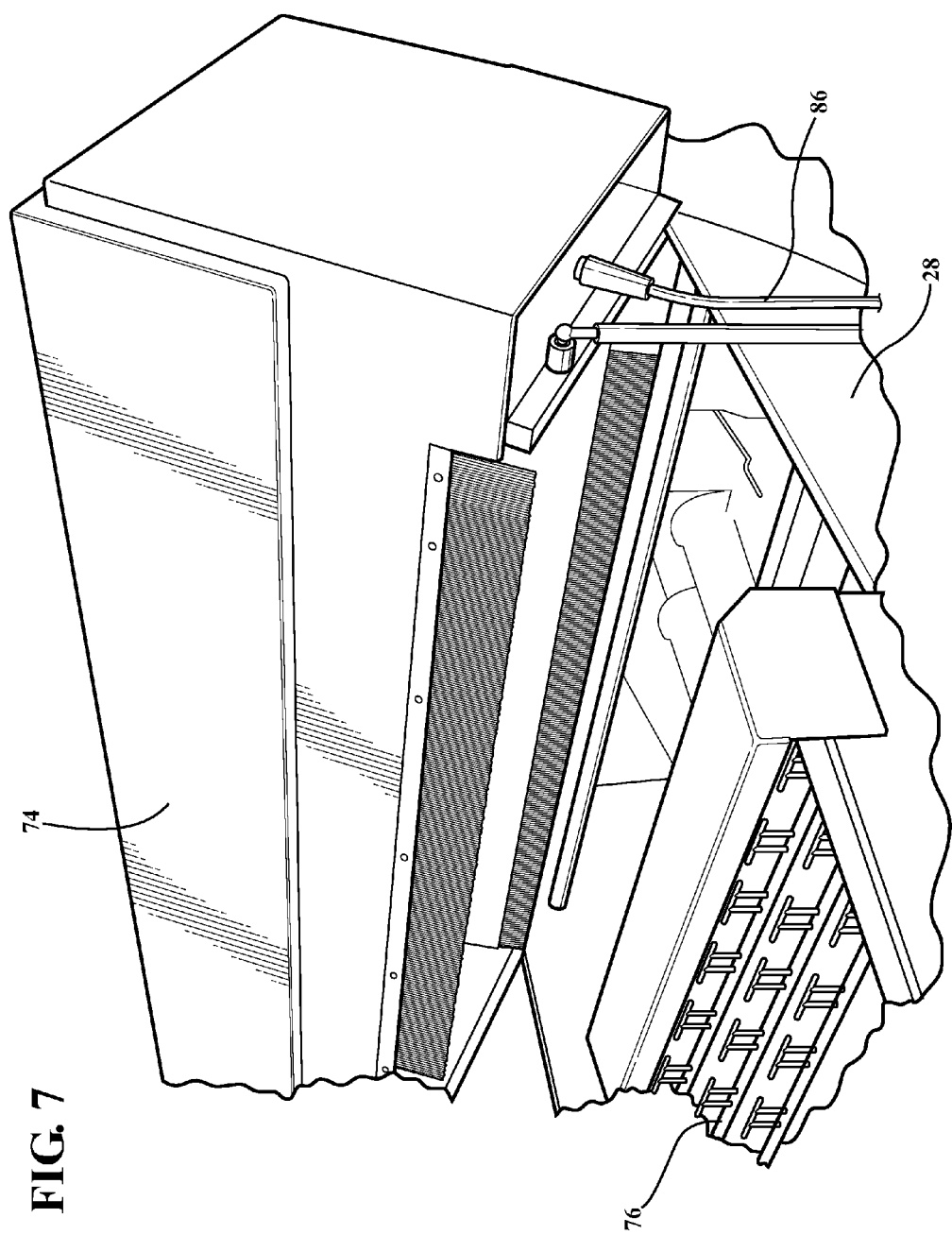
FIG. 7 is a sectional perspective of an initial vision and crack detection component associated with the egg inspection and removal subassembly depicted in FIG. 4.
Figure 8:
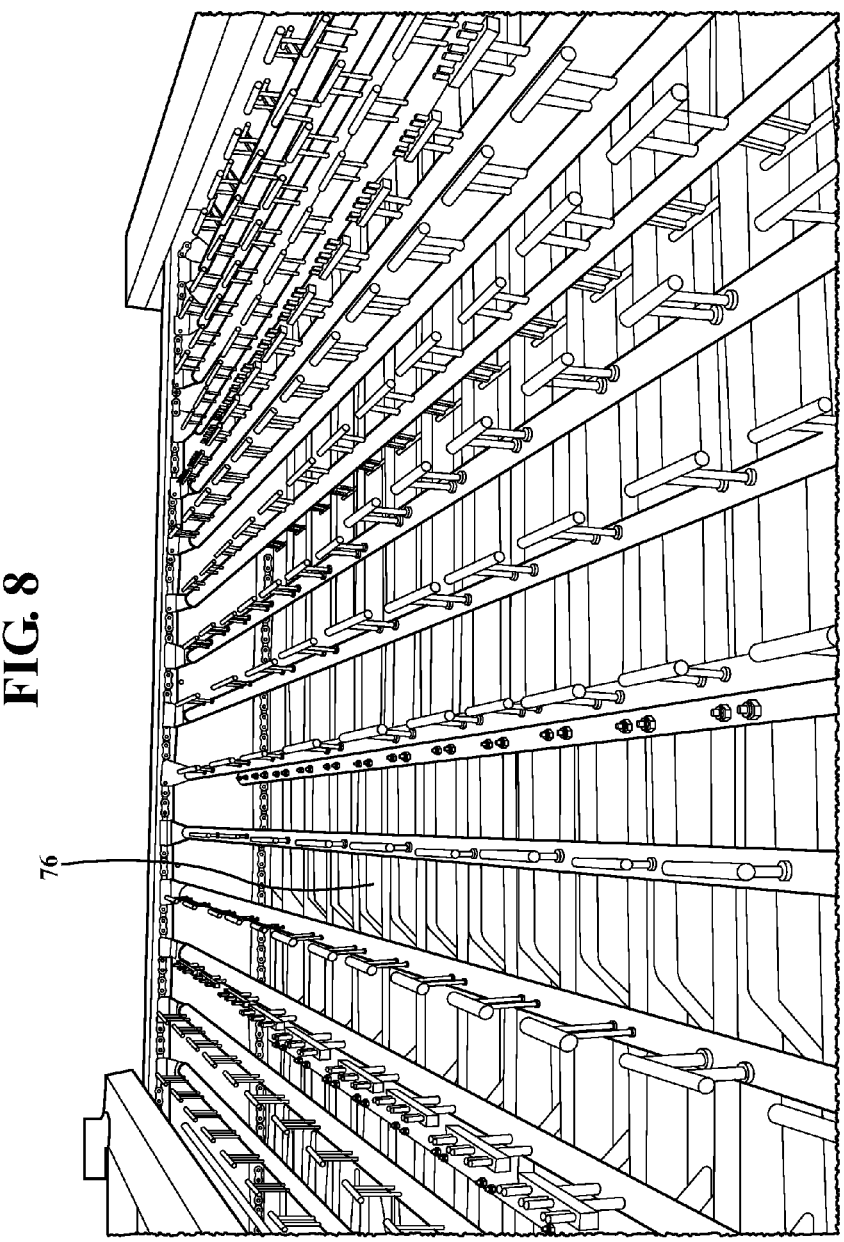
FIG. 8 is an illustration of the egg conveying/candling lanes established upon the egg inspection and removal subassembly.

FIG. 7, in combination with FIG. 4, depicts the first station vision inspection system 74. As previously described, the associated processor/controller 38 assigns advancing spool positions to each egg beginning at its receipt location from the specified laying house to a given entry lane 20, 22, 24 of the accumulator 12. By the point in time that the egg has been conveyed through the washer 26 to the inlet location of the inspection/removal subassembly 28, an interim/incomplete record of information pertaining to the washer parameters has already been assembled.

The vision system 74 exhibits a three dimensional cabinet or enclosure which is representatively depicted in FIG. 7 positioned in overhead and downwardly/angular positioned fashion. Although not shown, the vision system 74 incorporates a combination of light illumination and high resolution cameras (e.g. such as Ethernet connected digital cameras or the like) in order to inspect properties of each egg including without limitation dirt on shells, color of shells, broken or leaking eggs, mutilated shells or the absence of eggs. This information is interfaced to the central processor/controller 38, such as via a communication line or hardwire (see as depicted at 86) extending from the vision system 74.

Succeeding the vision system 74, the crack detection system 76 operates to inspect each egg for the existence of cracks and, if detected, an associated degree or severity. Without limitation, crack detection capabilities can be built into the overhead positioned vision system 74, such as which can provide a desired infrared or other wavelength illumination which, in combination with the rotating or candling of eggs upon a multiple lane defined conveyor construction (see FIG. 8), allow for quickly determining if any eggs are cracked or otherwise damaged. Data collected for each egg scan is incorporated into a file transmitted to the central processor 38 and assigned to each advancing egg location (throughout each spool section and interfacing/internal conveyor structure incorporated into each of the accumulator 12, washer 26, inspection/removal 28 and breaker 30 subassemblies). Also, and although not shown in FIG. 8, it is also envisioned that other or additional sensors could be located at locations, above, below or aside the conveying lanes illustrated in FIG. 8.

Following crack detection, obviously damaged and leaking eggs are discarded through the initial removal gate 80, with all remaining eggs being advanced to the next succeeding weighing component (see again FIG. 9) and which includes a plurality of individual digital scales 78 positioned within the subassembly 28 following the crack detection zone and prior to the second and third removal gates 82 and 84. The configuration of the digital scales are each such that they individually weigh each lane specific and advanced egg, with the data resulting from the digital weighing likewise being communicated to the processor 38 for incorporation into the aggregating data file/packet for that advancing egg location.

At this point, all shell egg quality data and parameters have been assigned and such that the processor 38 is configured to remove any number of the advancing eggs from the subassembly 28, such as to laterally extending and egress spool bar sections (not shown in FIG. 4) and based upon pre-set criteria which is compared to the individual egg data files assembled, such as by a look up table or the like built into the processor component 38. In one non-limiting variant, this can include the first gate 80 being instructed to remove eggs which are either leaking or exhibit major defects, the second gate 82 subsequently removing dirty eggs for rerouting by the egress spool section (again not shown) extending from the gate 82 to a reintroduction location prior to the washer 26. The third gate 84 is utilized to remove desirable eggs (typically larger sized and/or colored eggs) prior to be sent to the breaker subassembly 30, these eggs being more desirously used in more profitable shell packaging applications, with the remaining eggs being of a generally acceptable but non-remarkable quality suitable for delivery to the breakers and resultant reduction in to yolk and albumen components.

Once an egg is removed (either at this stage or subsequently) the pre-stored data characteristics need no longer be tracked through the system, with he associated egg record such as being stored in a database for purposes of future statistical evaluation. Along these lines, outright defective eggs are rejected (again gate 80), with other eggs being reprocessed if still dirty (gate 82) or subject to alternate processing (again gate 84) if higher quality or specific demand shell eggs possessing characteristics such as weight or color for routing to a grader for shell egg sales. Without limitation, the present invention contemplates the use of any number of removal gates, from one gate to any plurality thereof, and it is further understood that the removal parameters associated with any removal gate are also not limiting, this including the removal of quality shell eggs for alternate application, as well as the removal of poorer quality eggs (both shell or liquid) for either recycling (e.g. rewashing) or disposal.

Figure 10:
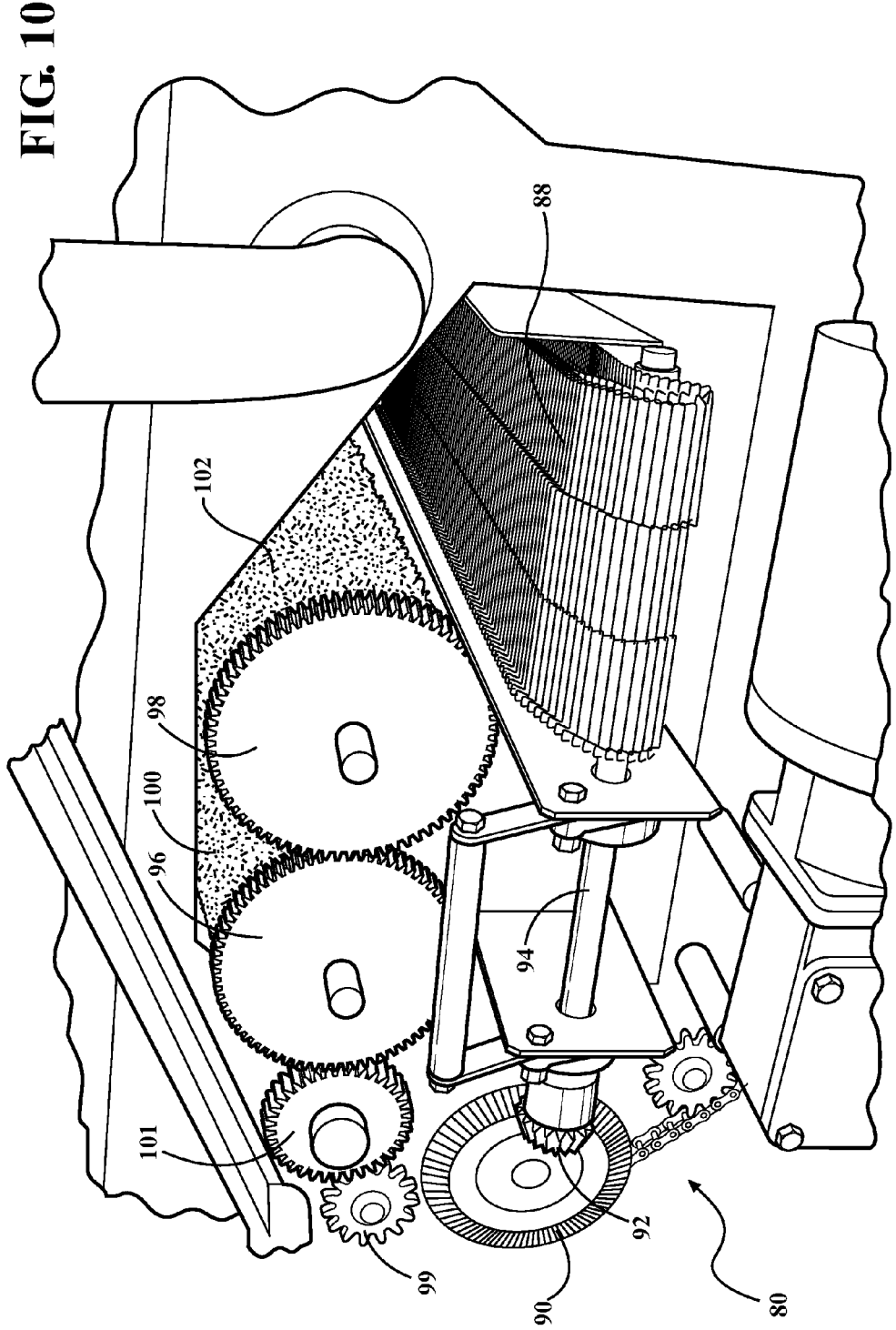
FIG. 10 is a sectional perspective of a selected removal gate associated with the inspection and removal station depicted in FIG. 4.
Figure 11:
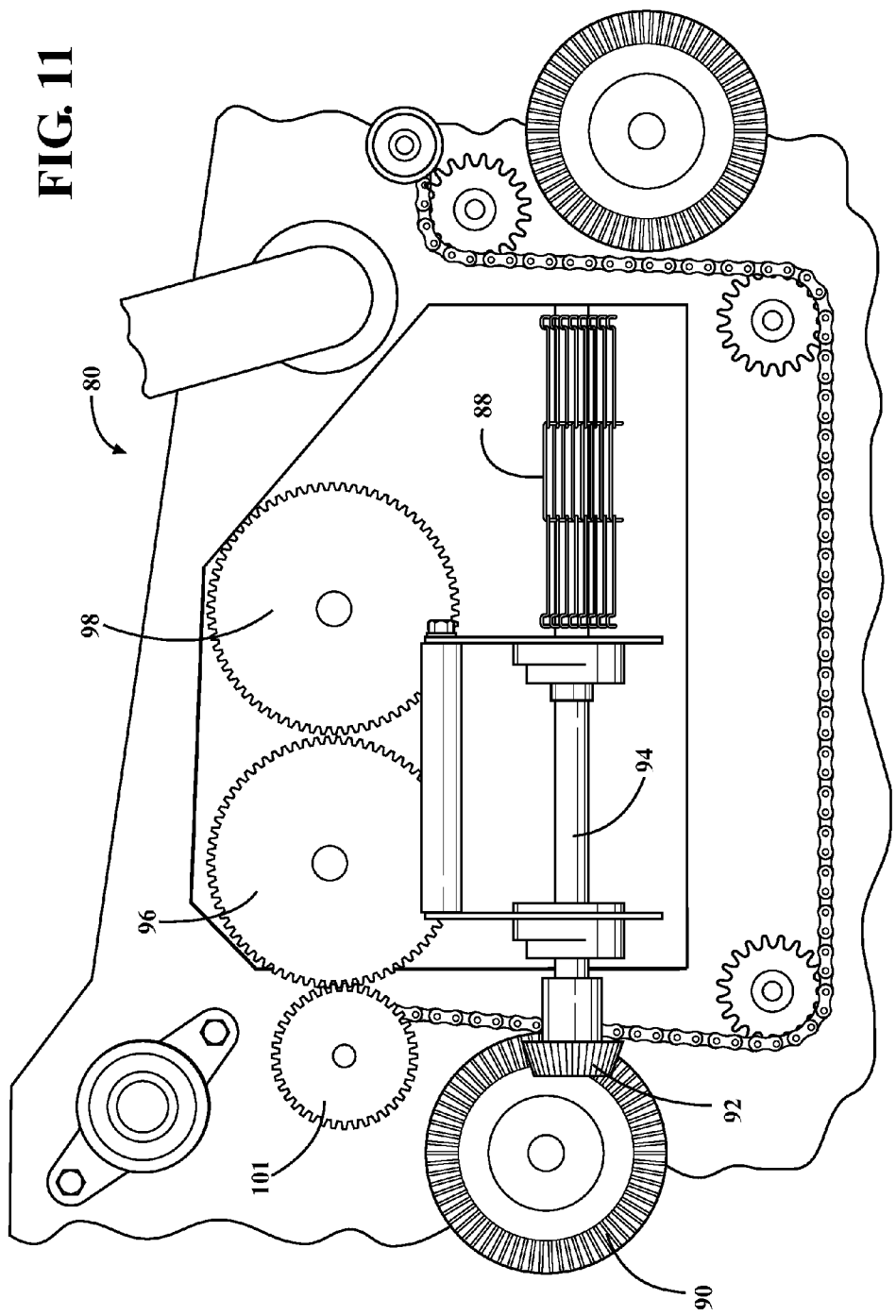
FIG. 11 is a side view of the removal gate in FIG. 10 and further depicting the gearing configuration for safely delivering shell eggs from overhead/internal conveyor extending lengthwise along the removal station to the underneath and lateral exit conveyor.
Figure 12:
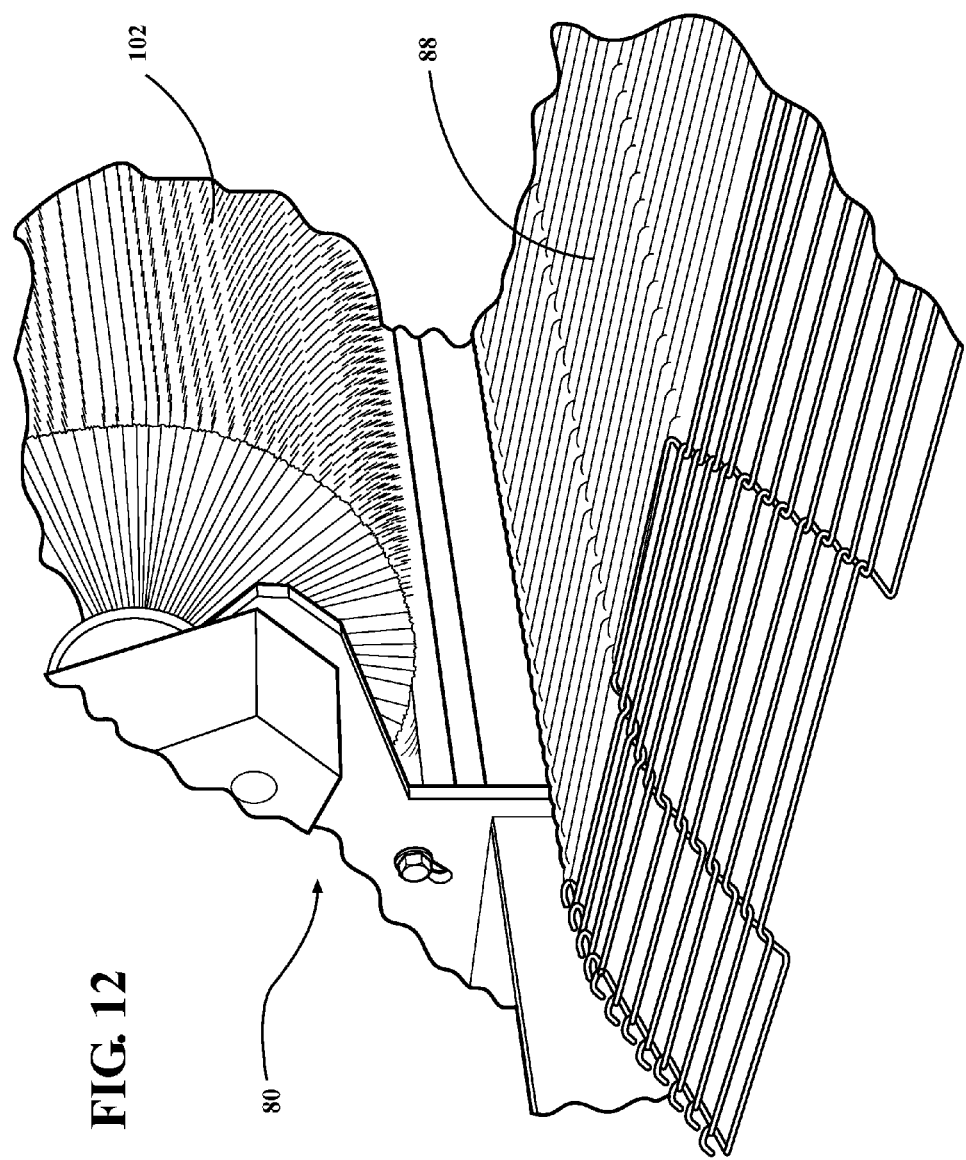
FIG. 12 is an enlarged partial illustration of a selected rotating egg delivery brush wheel also depicted in FIG. 9 and which is incorporated in opposing and spatially arrayed pairs for each removal gate and in order to facilitate safe delivery of eggs from the inspection and removal subassembly.
Figure 13:
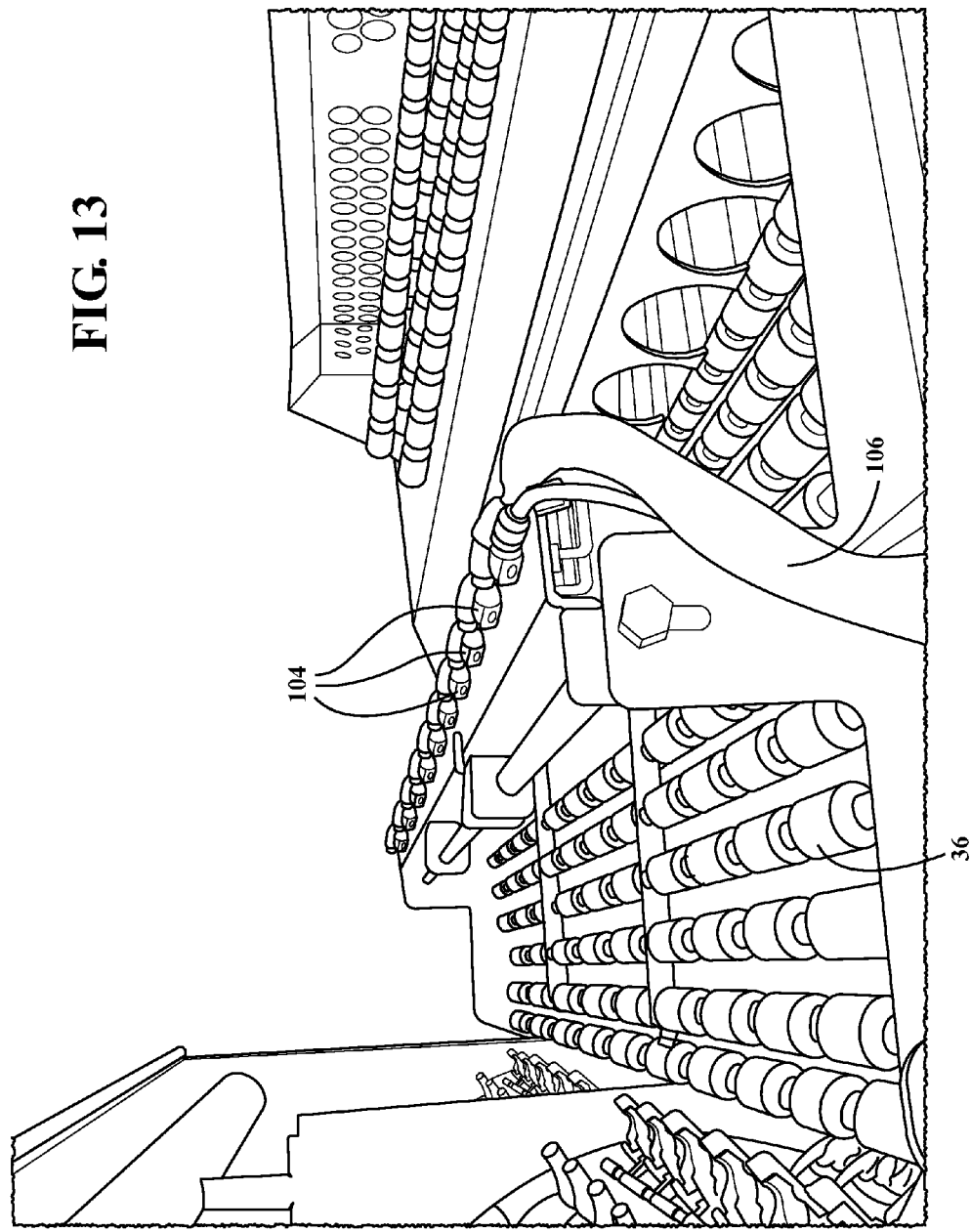
FIG. 13 is an illustration of egg counting sensors associated with the egg inspection and removal subassembly and which determine the presence of an egg in each conveyor position following manual candling and prior to delivery to the egg breaker subassembly.

FIGS. 10-12 illustrate a series of perspective, side and enlarged partial views of first selected removal gate 80 extending in communicating fashion with a side location of the subassembly 28 and which includes a belt conveyor 88 (connected to an exit ramp or other spool conveyor section depending upon the intended destination of the removed eggs and which could include damaged eggs such as from first gate 80 being quickly collected and disposed by an egress ramp, as opposed to additional spool sections for the second and third gates which carefully maintain and reroute the eggs to their intended destination). First and second bevel drive gears 90 and 92 are provided, with a shaft 94 extending from the second (driven) gear 92 both supporting and continuously drive the belt 88.

Additional to the constant lateral conveying direction of the belt 88 is the provision of a pair of widthwise extending, cylinder shaped and opposingly rotating brush elements, these including geared outer end plates 96 and 98 as best shown in FIG. 10 which are driven by a further pair of drive gear 99 and 101, the plates 96 and 98 in turn exhibiting inwardly extending and 360 degree extending tufts of bristles (see further at 100 and 102 respectively in FIG. 10 as well as illustrated in further detail at 102 in FIG. 12) in order to safely communicate eggs deposited, via descending passageways, from the above communicating lanes 76 for safe delivery upon the outlet conveyor belt 88.

By example, eggs of specific weight can be removed and rerouted through third gate 84 to a grader (not shown) for sale as shell egg product. Along these lines, a detected combination of characteristics can be used to remove specific eggs according to laying house, color, weight, cleanliness and absence of cracks. The provision of automatic removal gates results in a labor and material handling reductions (beyond that disclosed below in reference to the succeeding manual candling, inspection and removal stage) and, as a result, fewer employees are required to inspect the eggs visually and materially handle the eggs for reprocessing.

Following the three removal gates, and referring to FIG. 13, the remaining eggs pass underneath a plurality of lane aligned egg counting sensors 104 which determine the presence of an egg in each conveyor position following manual candling and prior to delivery to the egg breaker subassembly 30. A bundled communication line defining a wiring harness 106 extends from the individual sensors to the processor 38 and confirms 1) that eggs previously instructed to be to withdrawn through one of the gates are no longer present and 2) that eggs which are intended to proceed on to the breaker subassembly 30 are in fact present at this location.

The counting sensors 104 inspect the presence of each egg at an assigned conveyor lane (advancing) location established along the spool bars, following manual candling/removal and prior to breaking. Upon a designated egg counting sensor 104 detecting an egg missing where one is supposed to be, a determination is made that it is manually removed.

Reciprocally, the counting sensors 104 may detect an egg presence at a location where an egg is not supposed to be (such as indicative of one or more error conditions associated with functioning of the egg transfer system). In this instance, the processor system 38 will track the invalid egg through the remainder of the transfer system and, depending upon the system parameters, the machine can be stopped immediately, processed normally, or removed at a next available removal station.

Figure 14:
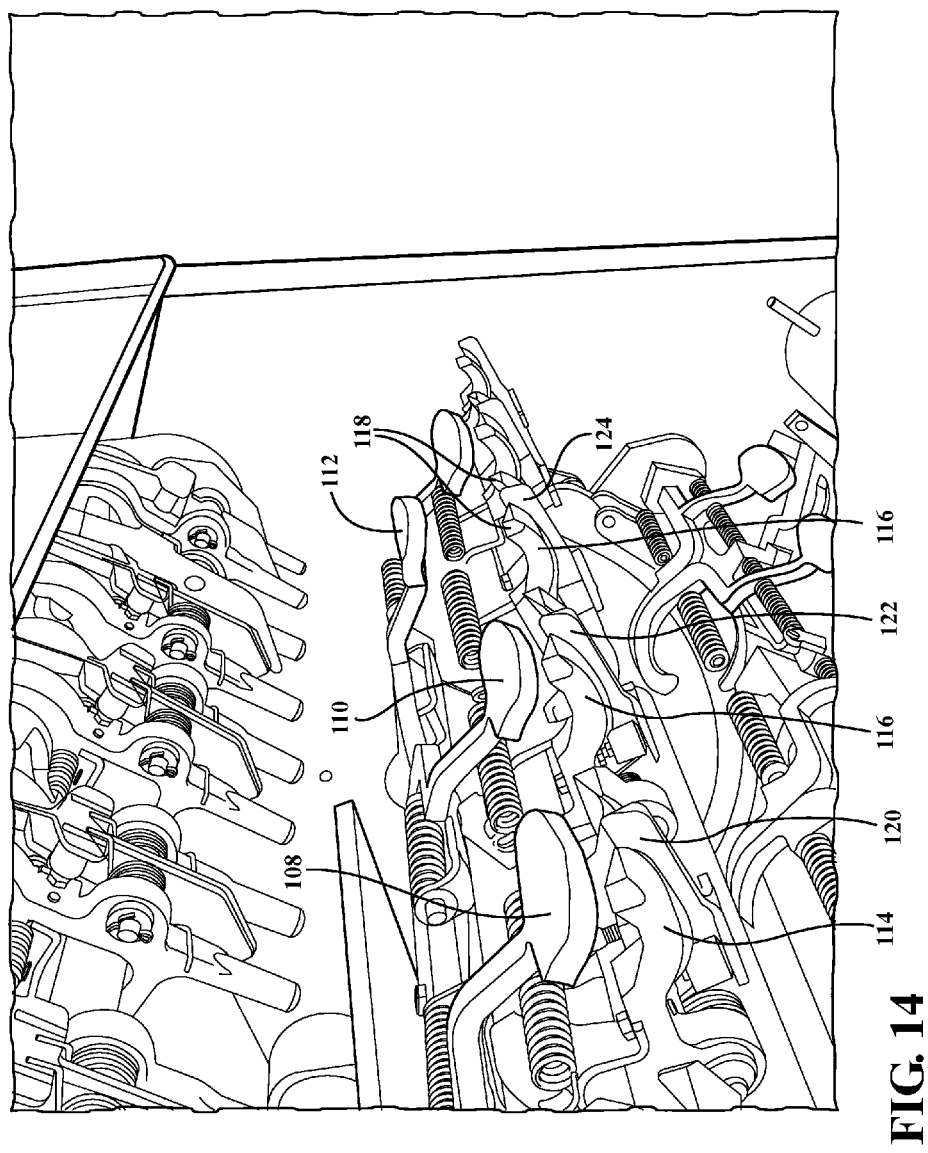
FIG. 14 is a sectional perspective of a plurality of egg holders/breakers and associated knives defining an initial component of the subassembly previously depicted in FIG. 5, the egg holders/breakers forming a continuous looped conveyor and including specified delivery locations interfacing with assigned conveyor locations at an outlet of the egg inspection subassembly downstream of the egg removal gates.

Referring to FIG. 5, in combination initially with FIG. 14, the egg breaking subassembly 30 provides a plurality of individual breakers which are formed in multiple rows and columns defining a continuous belt extending in continuous looped fashion within a forward end of the breaker subassembly and such that a selected row of breakers (equivalent in number to the number of lanes associated with the spool section 36) are arranged in synchronized communication with delivery locations of the spool section 36. An egg breaking zone is representatively illustrated at 107 in FIG. 5 and each of the breakers depicted in FIG. 14 include upper egg configured pad supports 108, 110, 112 et seq., opposing lower and spaced apart pairs of egg supports 114, 116, 118 et seq., and lower knifes 120, 122, 124, et seq. which are respectively located between the lower egg supports.

Figure 15:
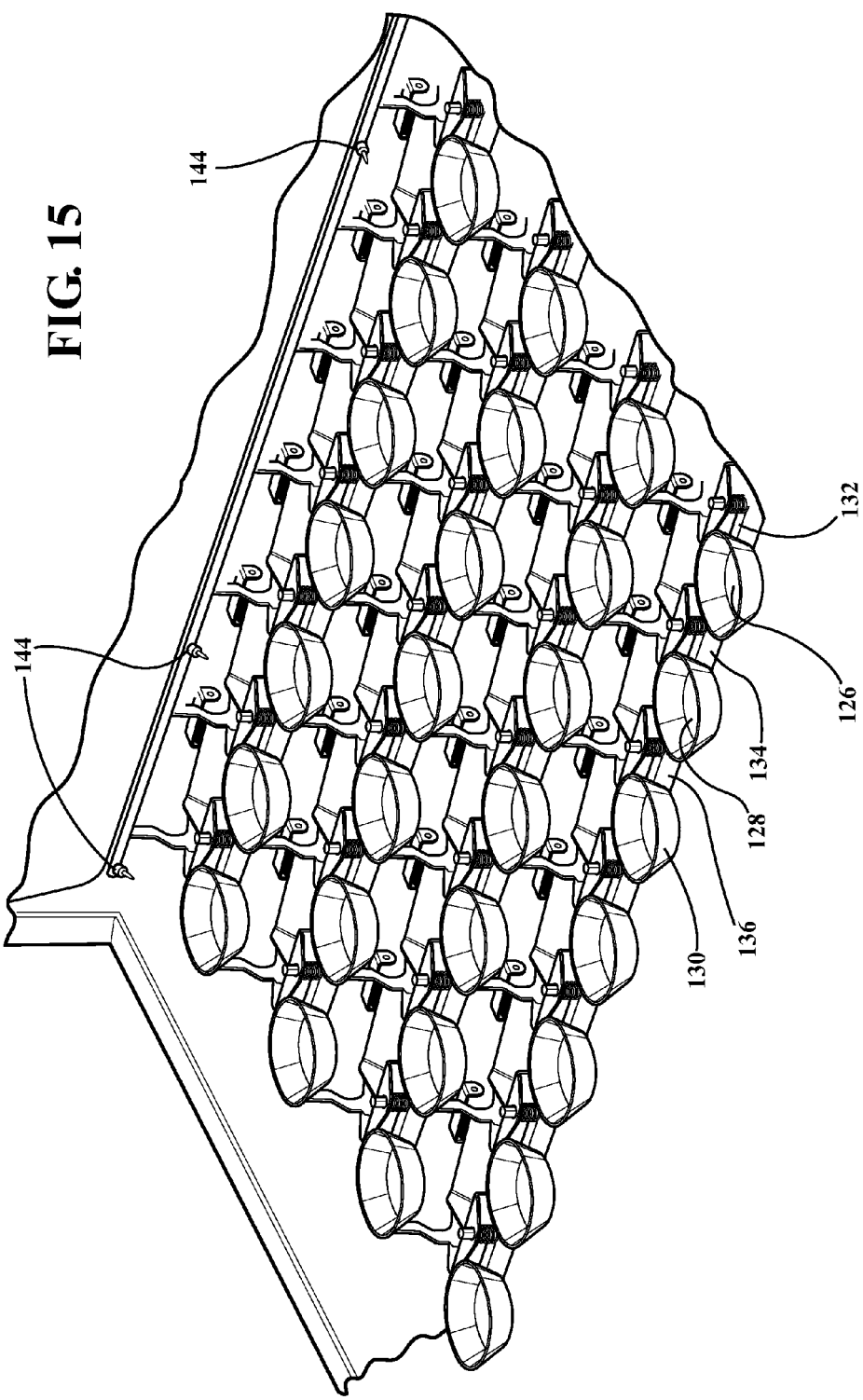
FIG. 15 a sectional perspective of a sub-plurality of yolk cup and albumen trays associated with the egg breaker subassembly and for receiving the contents of individually broken eggs, along with air displacement nozzles located at the initial receipt trays for quickly indicating the presence of rotten eggs to a manual inspector.

Referring further to FIG. 15, and upon the eggs being delivered to a specified breaker, the breaker is advanced to a location at which the knife is pivoted upwardly between the lower egg supports and so that the shell egg can be fractured for reduction of its yolk and albumen components, these being delivered in gravity fashion at a removal gate location 125 (again FIG. 5) into aligning yolk cups 126, 128, 130 et seq. and albumen holders 132, 134, 136 et seq. positioned underneath the breakers (see further zone 138 in FIG. 5). Similar to the breakers, the yolk cups and albumen trays are likewise mounted in similar row and column arrangement such that they define a second looped belt which interfaces with the breakers (subsequent reference is made to screen illustration 260 in FIG. 28 and in which cracker/breaker belt 135 interfaces with fluid cup/tray belt 137). At this point, the central processor control 38 records which set of tooling is employed to break the shell and separate the inner egg contents.

As previously described, the eggs entering the breaker subassembly 30 are tracked through the entire breaking process from the central processor system 38, with the specific tooling used to break the eggs also assigned to the egg breaking data. The pluralities of yolk holding cups and underneath communicating albumen trays receive the yolk and albumen contents of each broken egg, with each specified pair of cup and tray identified by the processor 38 as holding the fluidic contents of a previously designated shell egg for which the processor has assembled a data record.

Figure 16:
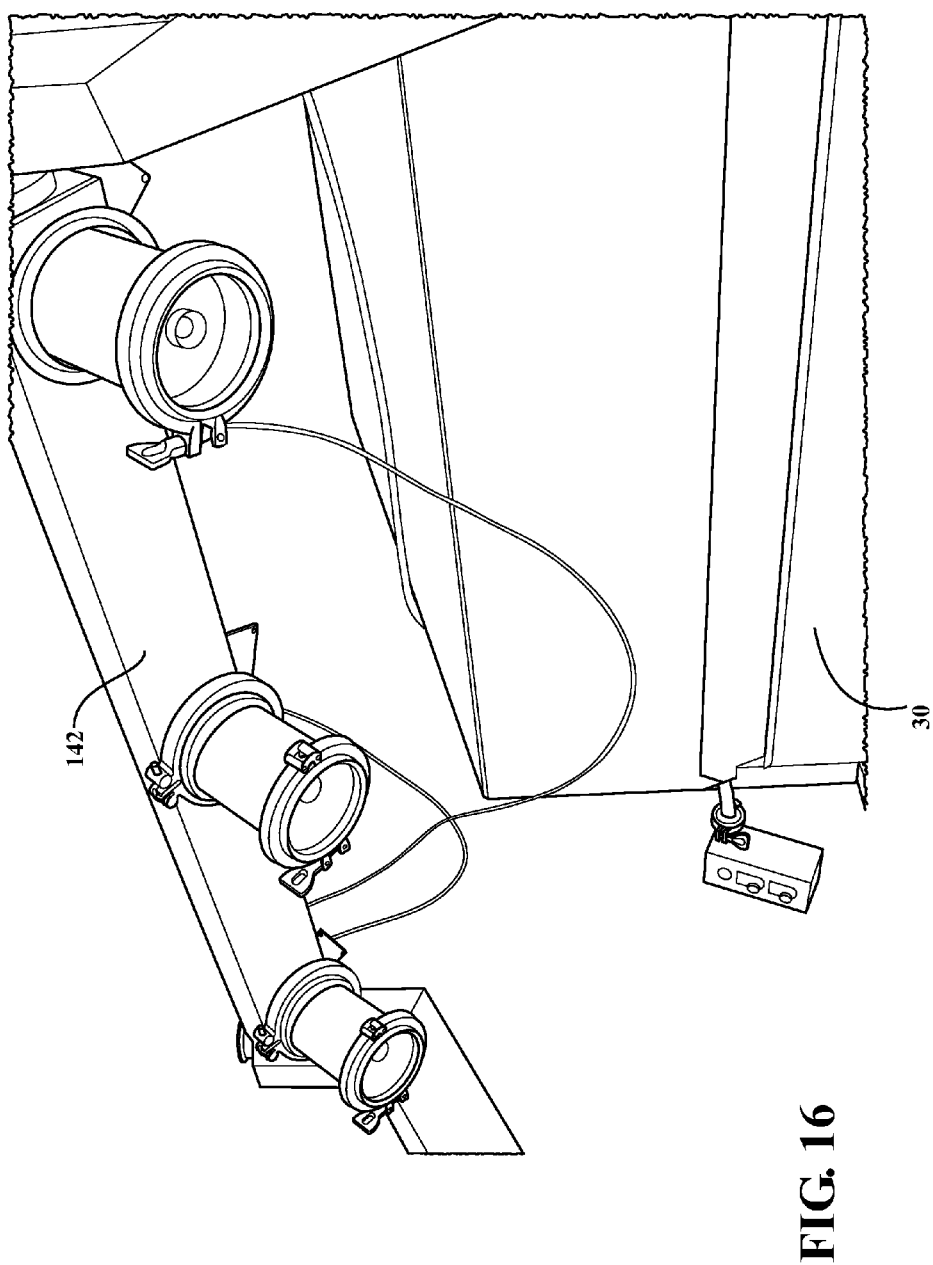
FIG. 16 is a succeeding view of a scan component associated with the egg breaker subassembly and such as for identifying without limitation such parameters as the absence of yolk and/or the existence of blood in the yolk.

At this point, the egg yolk and albumen held within a given cup and tray is successively advanced through a series of stations including a post-breakage yolk manual operator and inspection station 139, a vision inspection station 140 with concurrent albumen (including also combined yolk/albumen and whole egg contaminated) tray emptying and, following this, yolk fluid emptying station 141 at which the contents are emptied for further processing and the date and time of this being recorded to the central processor 38. Upon being delivered to a processor identified cup and holder, the yolk cups and underlying albumen trays are passed underneath a vision scanner 142 (see again FIG. 16) which is likewise in communication with the central processor 38 which maintains the process parameters and characteristics of the yolk and albumen resulting from the breaker operation and as visualized across station 140.

The post breakage vision scanner 142 (as contrasted from the shell egg inspection vision system 74 in FIG. 7) determines, among other possible parameters, absence of yolk or the existence of blood or other impediments in the yolk indicative of a bad egg or batch of eggs and which may require disposal of the yolk and/or albumen prior to fluid collection, such as further by triggering the selected cups and trays to dump their contents into a waste drain (see as schematically depicted at 143 in screen shot 260 of FIG. 28 and as further identified at 145 in FIG. 18) incorporated into the breaker subassembly 30. Air displacement nozzles 144 (again FIG. 15) are also located at the initial receipt trays for quickly indicating the presence of rotten egg fluid contents to a manual inspector located at station 139 and in order to quickly dispose of any such contents prior to collection and contamination within a larger safe yolk and/or albumen reservoir.

As previously indicated, any cup/tray containers which have been manually (operator) emptied during the previous operation are identified and recorded to the central processor 38, with the egg content defect data stored to the central system 38. Following desirable albumen removal through drain 148, whole egg removal is accomplished through drain 150 as indicated by vision inspection station 142, and at which point the contents then progress through the automatic removal station 141 at which the contents of each cup and tray are selectively removed based upon the previously assembled inspection criteria (data record) corresponding to a desired application (yolk only, white only, admixture, etc.). Again, the record of each cup and try is recorded to the central processor 38 with any remaining egg contents are emptied for further processing.

Figure 17:
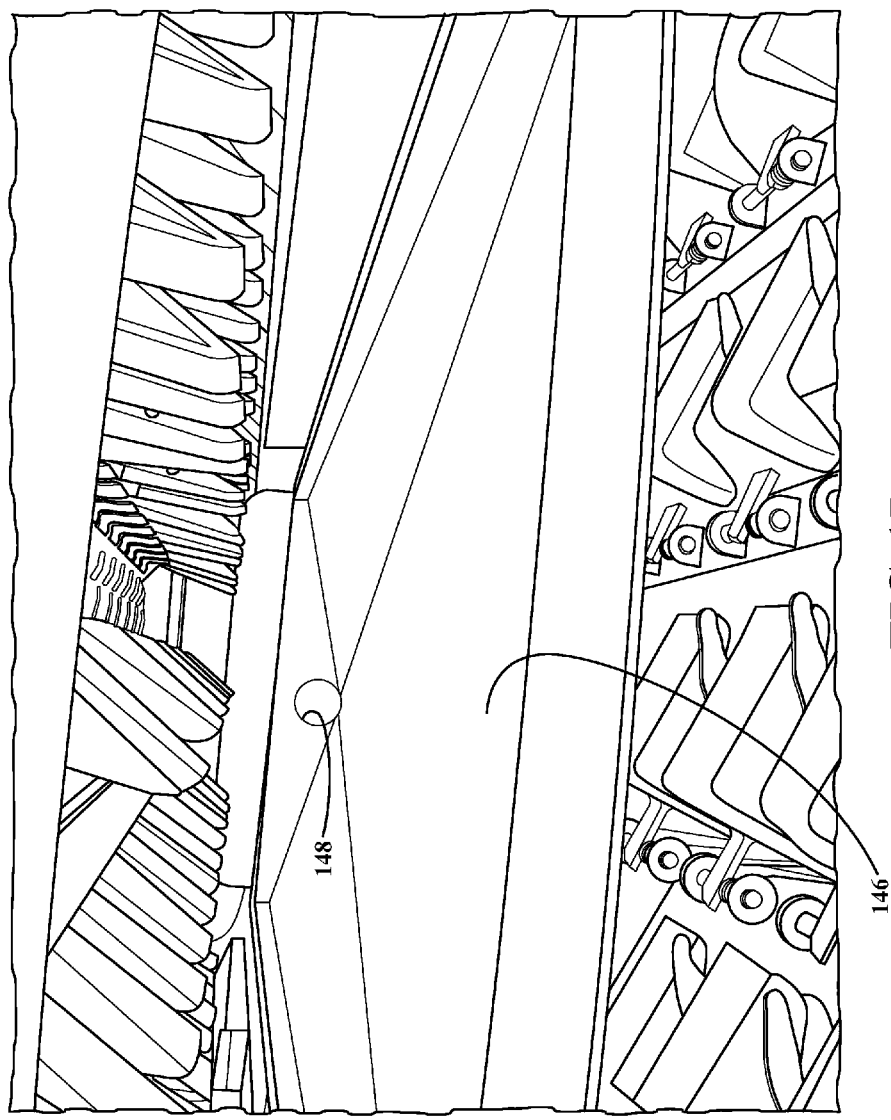
FIG. 17 is an internal view of an inclined albumen fluid collection ramp located underneath a section of pivoting albumen holding trays, a subsequent yolk collection ramp receiving yolks deposited from pivoting yolk holding cups
Figure 18:
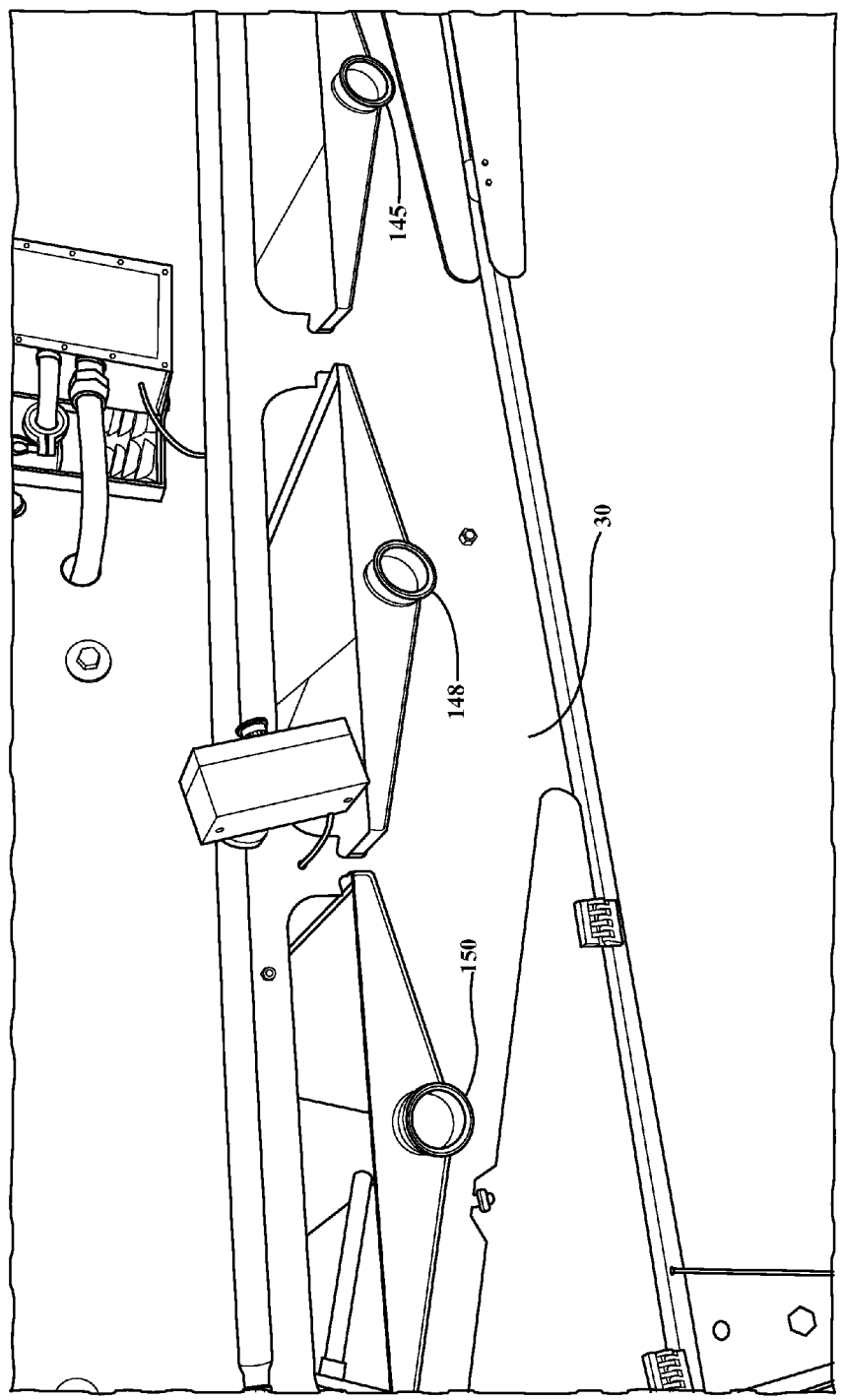
FIG. 18 is a perspective side/end view of fluid exit locations associated with manual operator yolk/albumen, quality albumen, vision inspection triggered yolk/albumen and quality yolk collection discharges associated with the egg breaker subassembly.

Consistent with the final emptying stage 141 of all remaining yolk (and residual albumen) contents which survive both the process controlled vision scanning 142 and the preceding manual inspection/removal 139, FIG. 17 provides an internal view of an inclined albumen fluid collection ramp 146 located underneath a section of fluid release/pivoting albumen holding trays, a subsequent and likewise constructed yolk collection ramp successively receiving yolks deposited from pivoting yolk holding cups. FIG. 18 is a side view of fluid exit locations 145, 148, 150 and 151 again associated respectively with manual operator waste yolk/albumen (145), quality albumen (148), whole egg discharge via vision system (150) and quality yolk discharge 151 associated with the egg breaker subassembly 30.

Although not further shown, additional lengths of conduit are connected to communicate usable yolk (discharge 151) and albumen (discharge 148) from the end stage of the transfer assembly, such as for use in subsequent fluid packaging operations. The yolk discharge 151 is further illustrated at an underside remote end location of the breaker subassembly 30.

Given the above system description, reference is now further made to the screen shot illustrations set forth in FIGS. 19-51 and which collectively detail one non-limiting example of an operating program associated with central processor 38, such as is presented on a screen or monitor display and which can also include the provision of either touch screen or keyboard/mouse input features. The present invention contemplates both the integration of a central processor control into a dedicated design for an egg transfer system, as well as the retrofit adaptation of a processor with associated wiring and controls for use with an existing egg transfer system which may or may not include each of the features depicted in the illustrated design, such as the washer, breakers, and the like.

As further referenced in FIG. 1, the central processor 38 is depicted as a breaker system control panel generally referenced by dashed outline box and which incorporates each of Panel PC Controller and HMI 152, Slice I/O System for Local I/O 154, Safety Processor for Safety Slice I/O 156, Yolk Scanner Computer 158, Dirt Detector Computer 160 and collective Ethernet Hub 162 communication. As previously described, included within the overall control panel are the input/output connections to each of washer drive 164 (input line 42 and output line 52), pusher drive 166 (input line 44 and output line 54), infeed drive 168 (input line 46 and output line 56), cup drive 170 (input line 48 and output line 58) and cracker drive 172 (input line 50 and output line 60).

Figure 19:
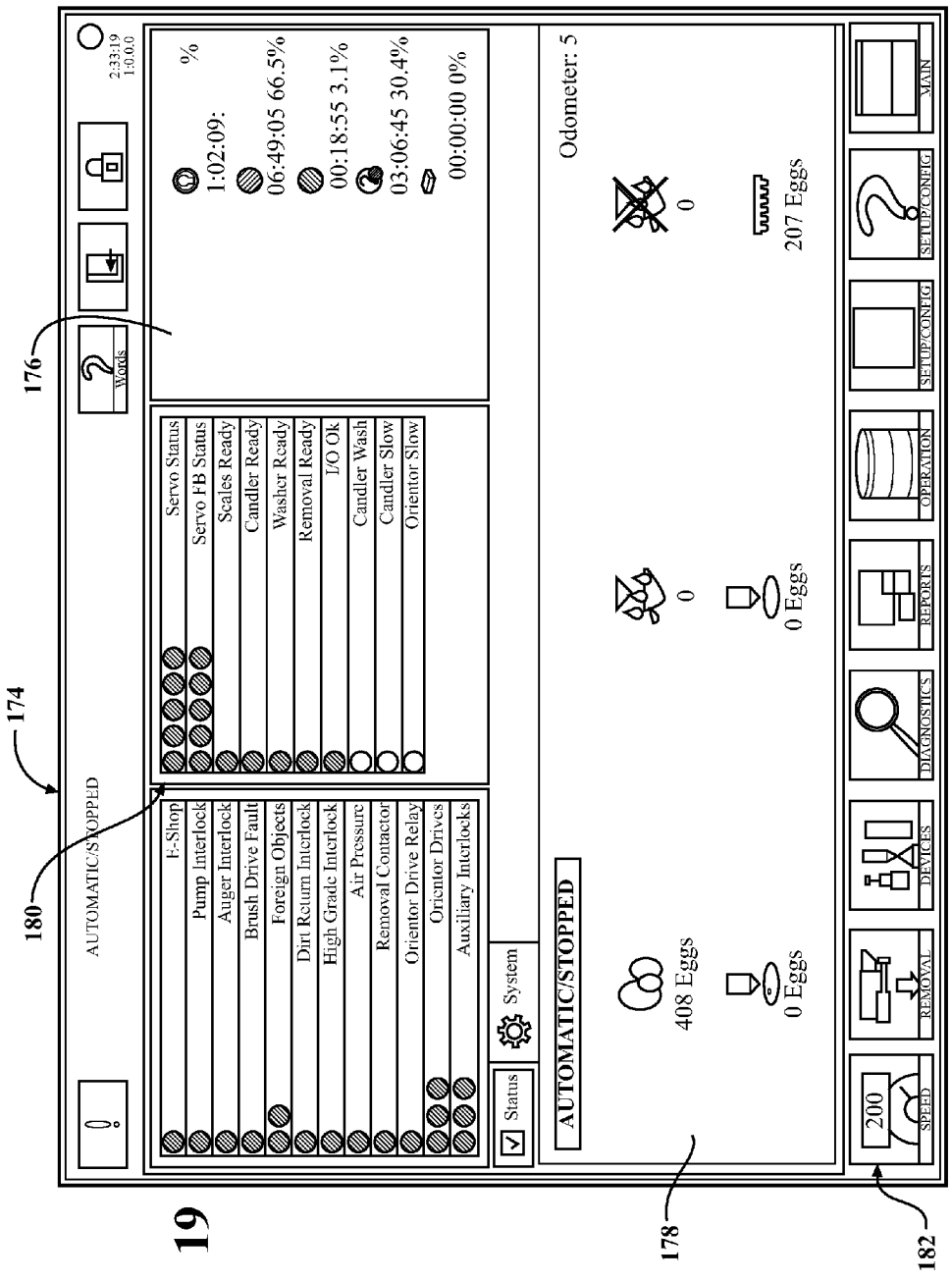
FIG. 19 is an initial screen illustration of an operating program incorporated into the central processor control network schematically depicted in FIG. 1, incorporated into the egg transfer assembly and which illustrates a top level control screen for the control software displaying production timers, production counts, machine state, interlock status and device status, as well as providing notification of system errors and warnings in the form of drop down listings which can include extended help information and shortcuts to appropriate diagnostic screens.

Given the above, and with reference initially to FIG. 19, an initial screen illustration is shown at 174 of an operating program incorporated into the central processor control network, again 38, schematically depicted in FIG. 1 and incorporated into the egg transfer assembly 10. Screen illustration 174 defines a top level control screen for the control software displaying a number of features including production timers (section 176), production counts (section 178), in addition to additional readout features, collectively identified at 180, and including such as machine state, interlock status and device status, as well as providing notification of system errors and warnings in the form of drop down listings (such as depicted at 182 extending along bottom margin) which can include extended help information and shortcuts to appropriate diagnostic screens.

Figure 20:
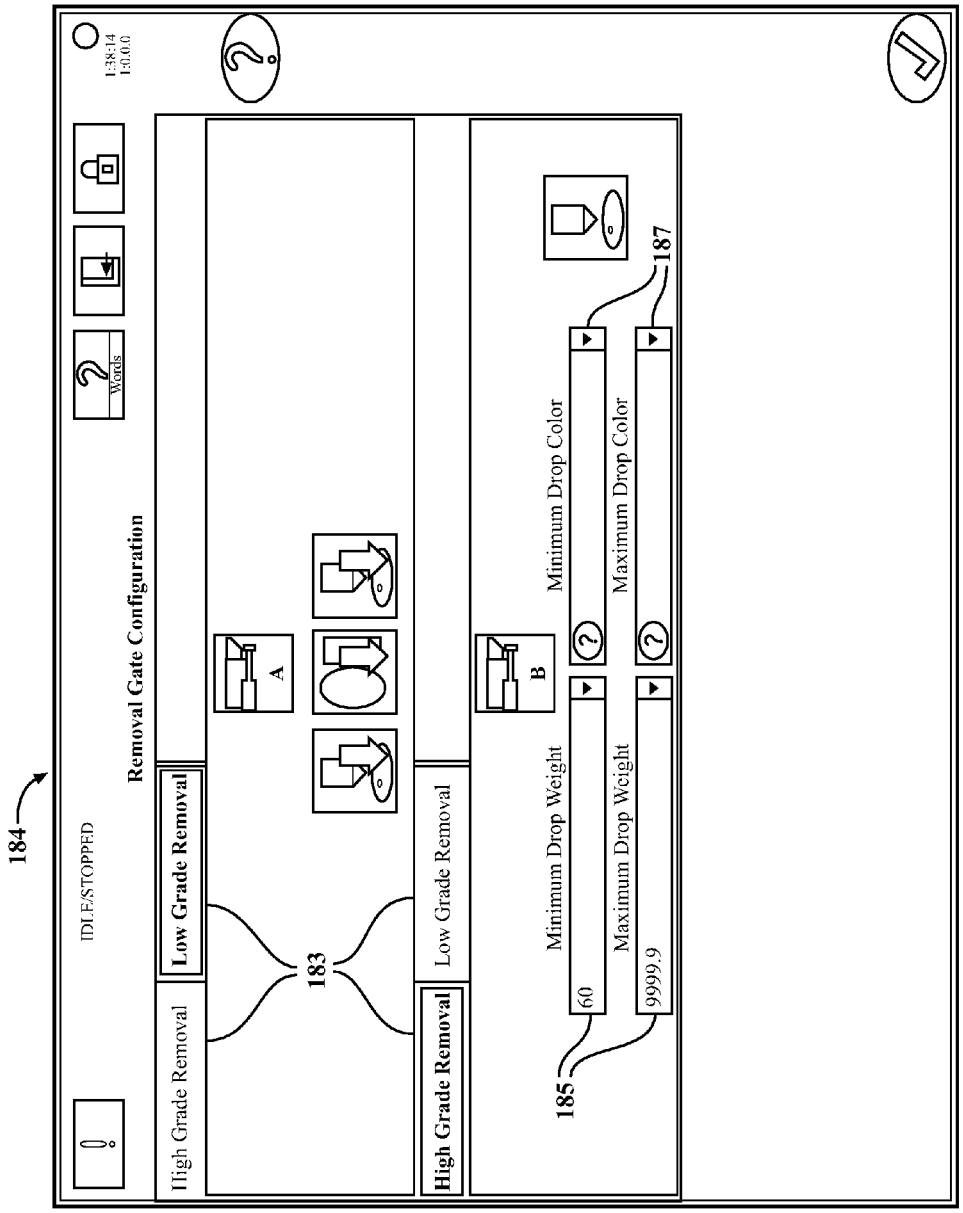
FIG. 20 is a succeeding screen illustration of a control screen used to customize the parameters associated with the removal gates, including removal of high/low grade eggs, dirty, cracked or leaking eggs and, in particular regard to high grade eggs, removal based on weight, color and cleanliness.

FIG. 20 is a succeeding screen illustration 184 of a control screen used to customize and configure the parameters associated with the removal gates 80, 82 and 84, including removal of high/low grade eggs (either gate 80 or 84), dirty, cracked or leaking eggs (again through gate 80 or second gate 82 for rewash eggs as per the illustrated and described variant) and, in particular regard to high grade eggs, removal based on weight, color and cleanliness (such as again through third gate 84). This screen includes particular parameter entry fields which allow for configuring the parameters for specifying the removal of eggs by grade 183, weight 185, or color 187 (again presumably but necessarily exclusively through third gate 84 for selective removal and apart from condition sensed removal of damaged (gate 80) or dirty (gate 82) eggs by the central processor 38.

Proceeding to FIG. 21, control screen 186 is used to fetch and view information stored on the digital scales (again previously illustrated at 78 in FIG. 9 associated with the inspection and removal subassembly 28) and including such information fields as serial number 188, firmware version 190, manufacture date 192, installation date 194, calibration date 196, calibration weight 198, calibration factor 200, tare 202 and initials 204 of the individual who last calibrated the scale.

Figure 22:
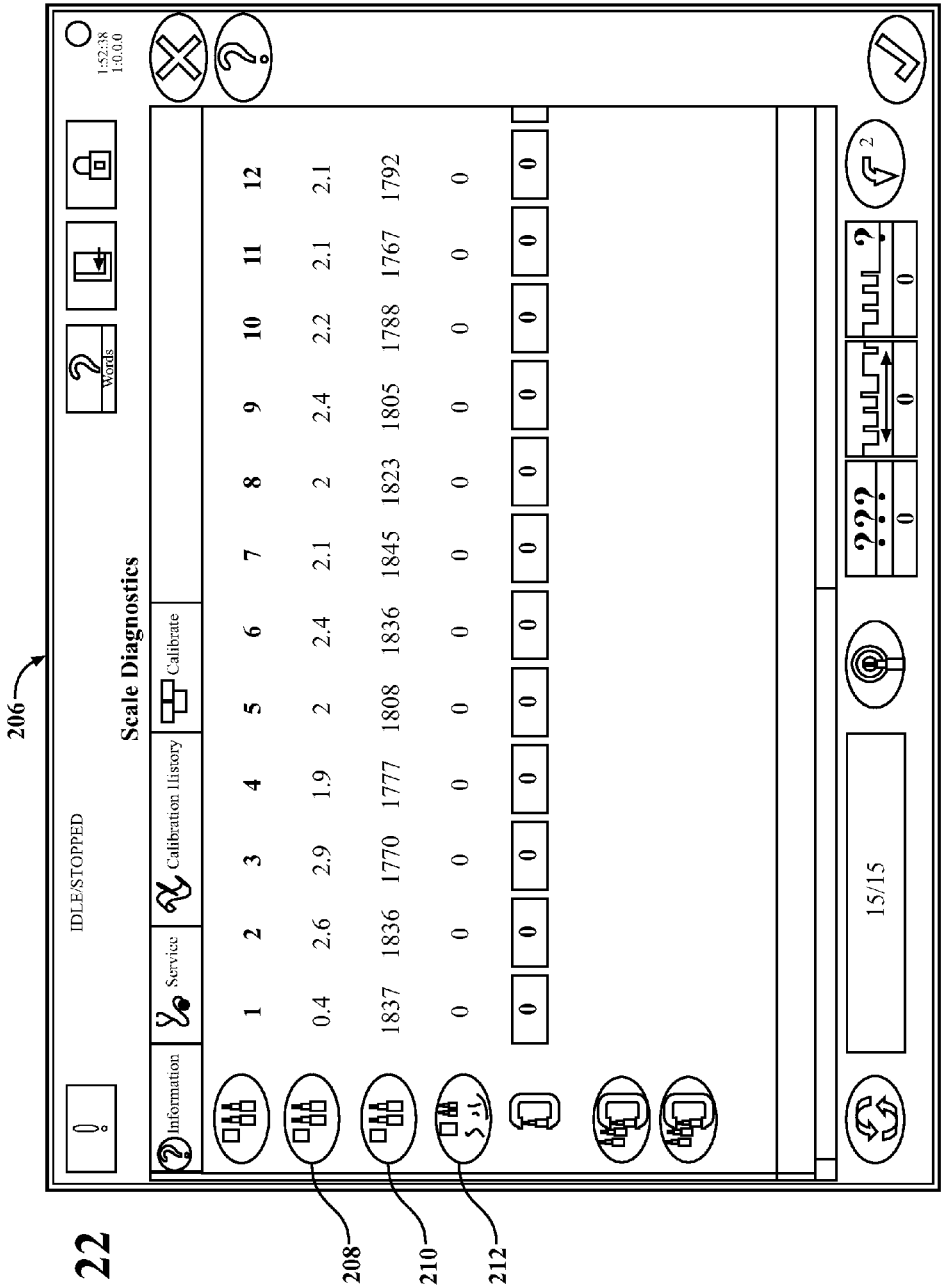
FIG. 22 illustrates a control screen used to fetch, view and change information stored on the digital scales including weight, tare, egg count and fake weight, and which is used to check scale initialization status and communication fault counts such as missing packets, and oversize/undersize packets.

FIG. 22 illustrates a control screen 206 used to fetch, view and change information stored on the digital scales (numbered 1-12) and including specific fields as weight 208, tare, egg count 210 and fake weight 212, and which is used to check scale initialization status and communication fault counts such as missing packets, and oversize/undersize packets.

Figure 23:
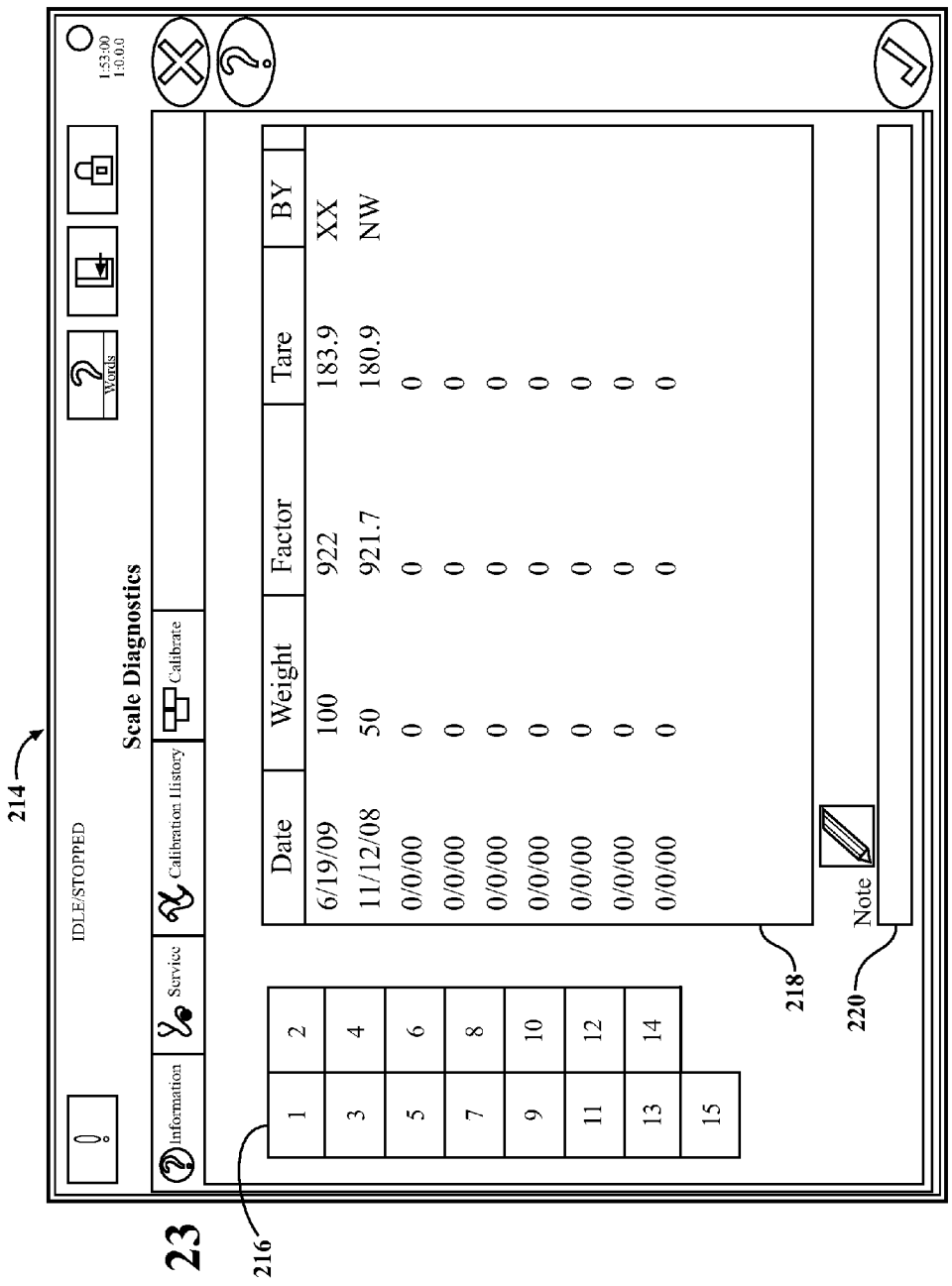
FIG. 23 illustrates a control screen used to view scale calibration history stored on digital scales which includes dates of calibration, calibration weights used, resulting factor, resulting tare, initials of the person calibrating the digital scale, and notes.

FIG. 23 illustrates a control screen 214 used to view scale calibration history stored on digital scales (identified in this Figure at section 216 as scales 1-15) and which includes, in a further exhibit field 218, dates of calibration, calibration weights used, resulting factor, resulting tare, initials of the person calibrating the digital scale, and notes field 220.

Figure 24:
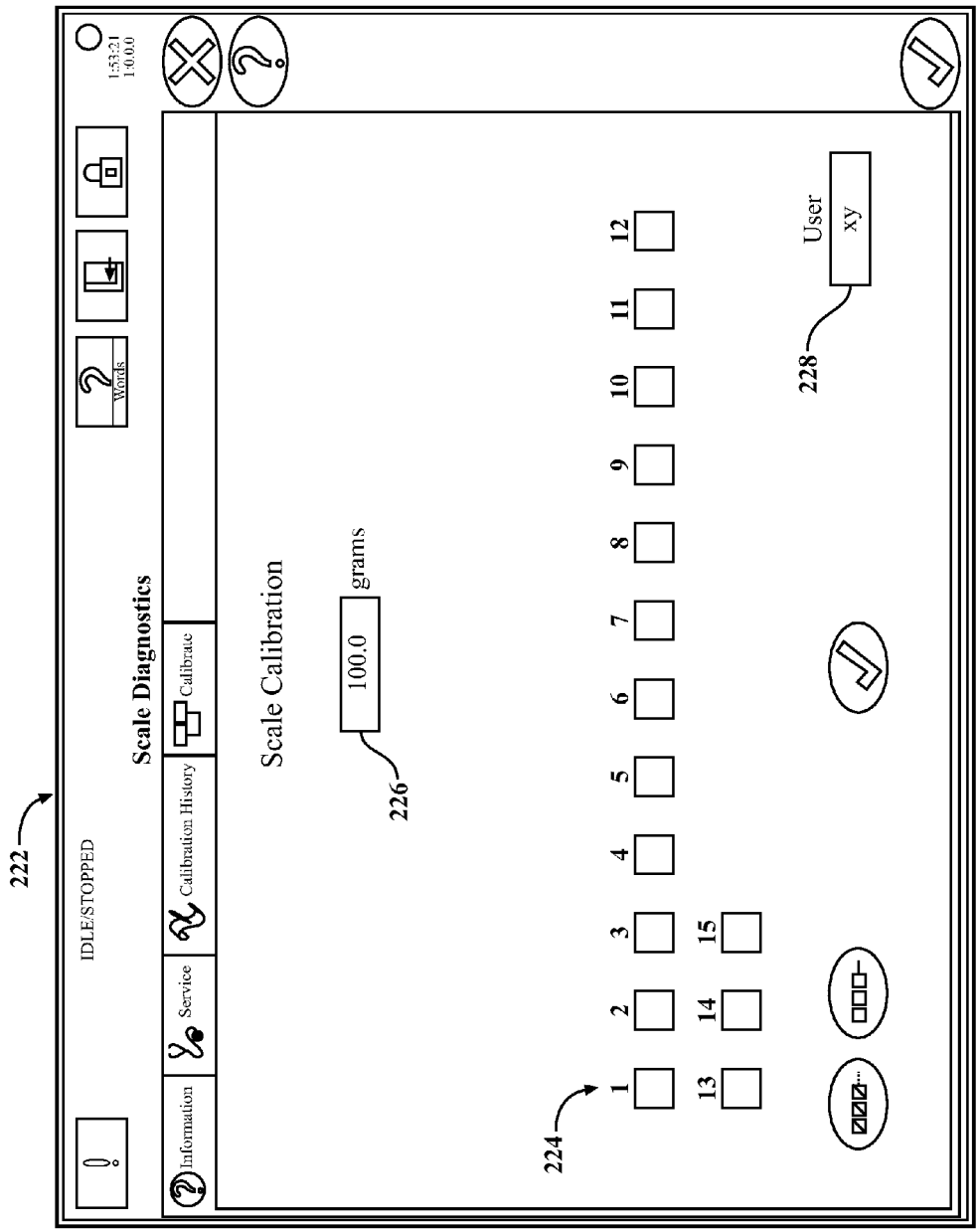
FIG. 24 is an illustration of a control screen used to calibrate one or more digital scales via a calibration wizard given a user specified calibration weight and initials.
Figure 25:
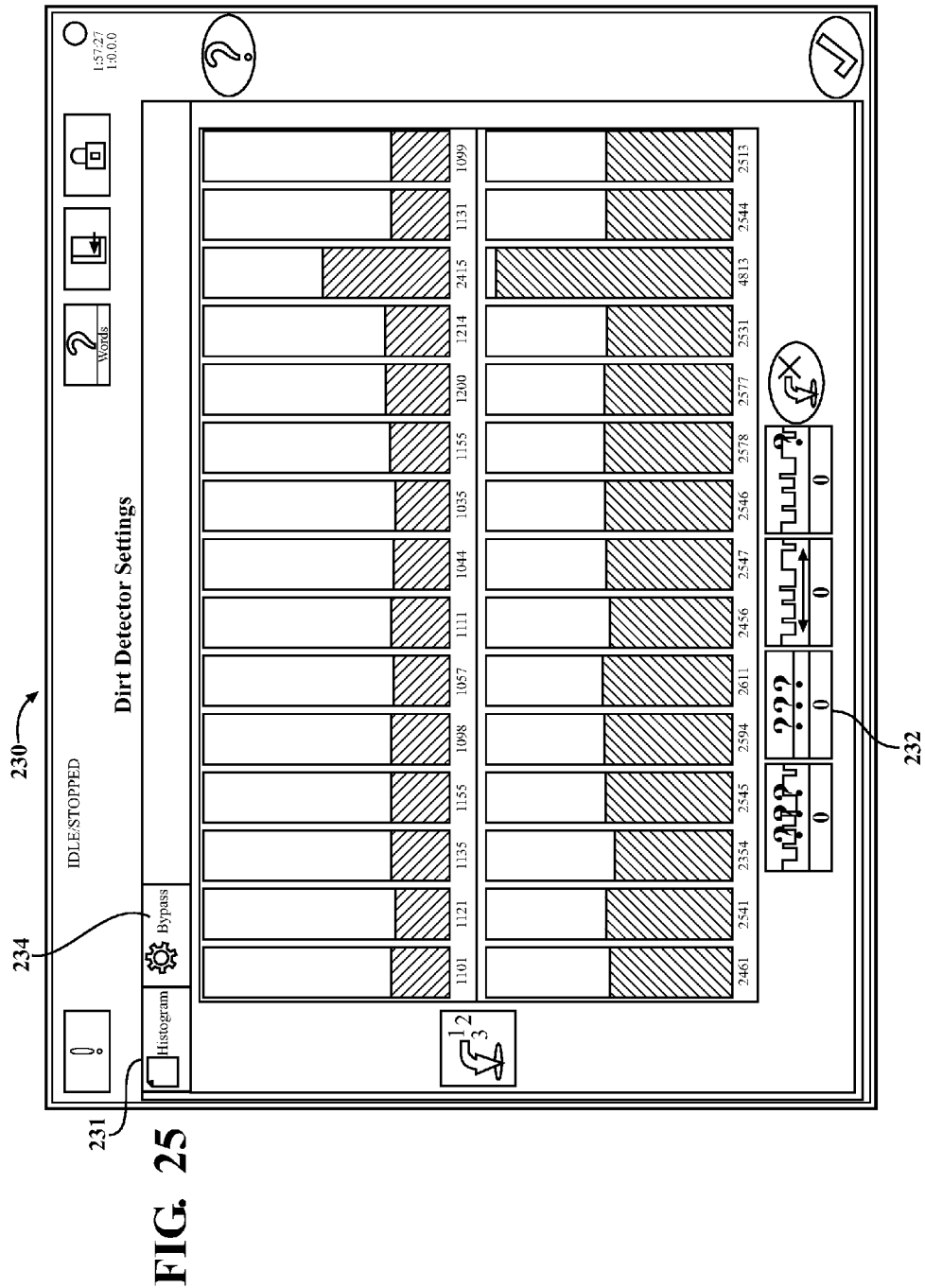
FIG. 25 is a control screen used to display dirt detection and leak detection results in a histogram format, which makes problematic lanes or cameras obvious, as well as providing communication fault counts including invalid, missing, oversize or undersize packets, while also providing bypass functionality to ignore spurious dirt and leak data.

FIG. 24 is an illustration of a control screen 222 used to calibrate one or more of the digital scales 224 via a calibration wizard given a user specified calibration weight 226 and user initials 228. FIG. 25 is a succeeding control screen 230, the main display field of which is used to display dirt detection settings and leak detection results in a histogram format (election field 231), providing the ability to accomplish helps to render problematic lanes or cameras obvious. Additional features include fields 232 for providing communication fault counts including invalid, missing, oversize or undersize packets, while also providing bypass functionality (election field 234) to ignore spurious dirt and leak data.

Figure 26:
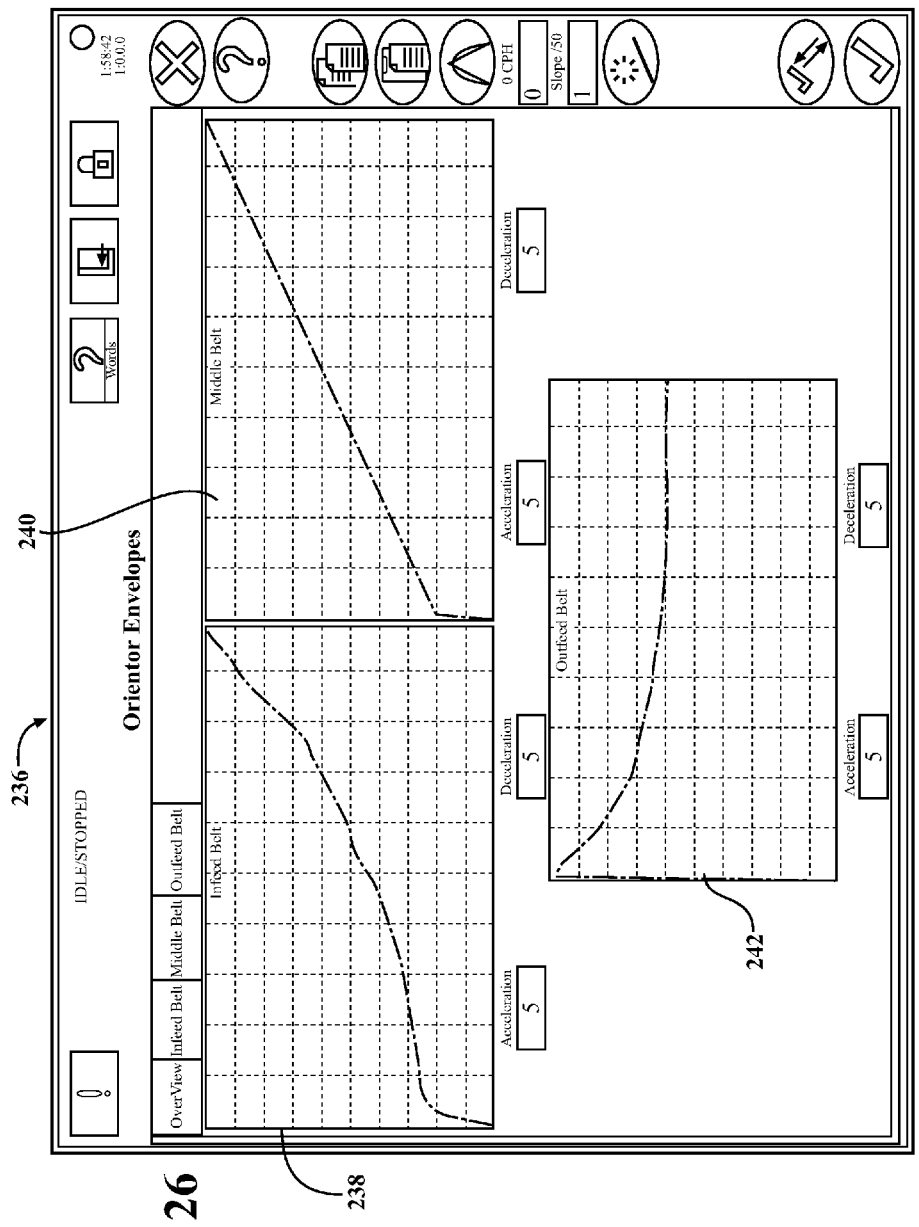
FIG. 26 is a control screen used to display and modify speed envelopes for the orientor/accumulator belts, as well as setting the acceleration and deceleration rates, which control how the orientor changes speed relative to the other machine components.
Figure 27:
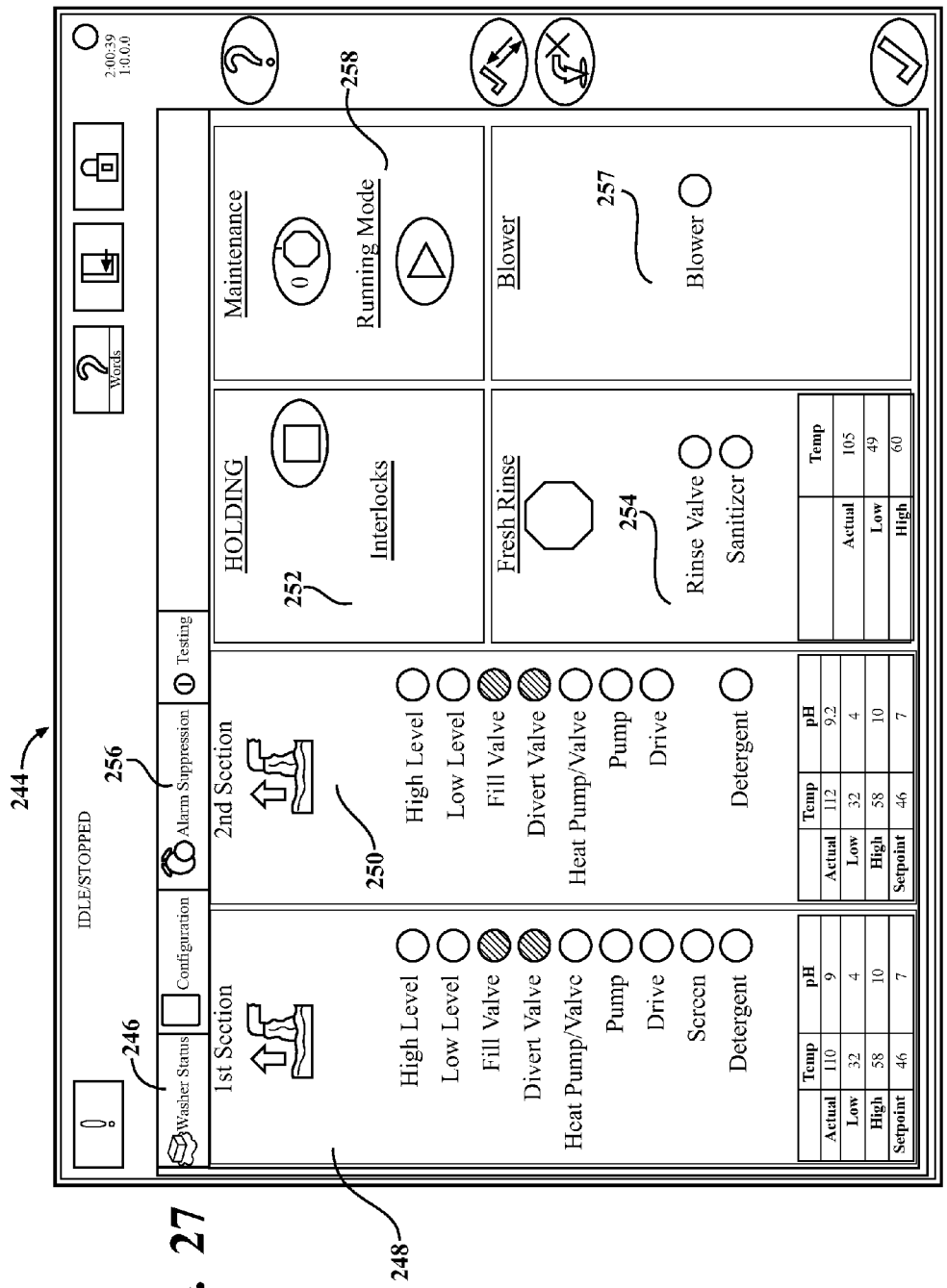
FIG. 27 is a control screen used to monitor and control all aspects of the egg washer subassembly including I/O status, section control states, temperature and pH readouts, tolerance settings, temperature set points, pH set points, failure alarm timeouts, and a maintenance mode which allows forcing I/O for testing and maintenance.

Referring to FIG. 26, control screen 236 displays and modifies speed envelopes for each of the orientor belts (depicted by fields 238 for infeed belt, 240 for middle belt and 242 for outfeed belt) as well as setting individual acceleration and deceleration rates for each belt 238, 240, 242, which control how the orientor/accumulator 12 changes speed relative to the other (succeeding) machine components or subassemblies. FIG. 27 is a control screen 244 used to monitor and control all aspects of the egg washer subassembly 26 notably including the I/O (washer) status 246, section control states (first section 248 and second section 250), temperature and pH readouts for each section 248 and 250, tolerance settings (including hold/interlock 252), temperature set points 254, pH set points (again 248 and 250), failure alarm timeouts 256, blower status 257, and a maintenance mode 258 which allows forcing I/O (input/output) for testing and maintenance.

Figure 28:
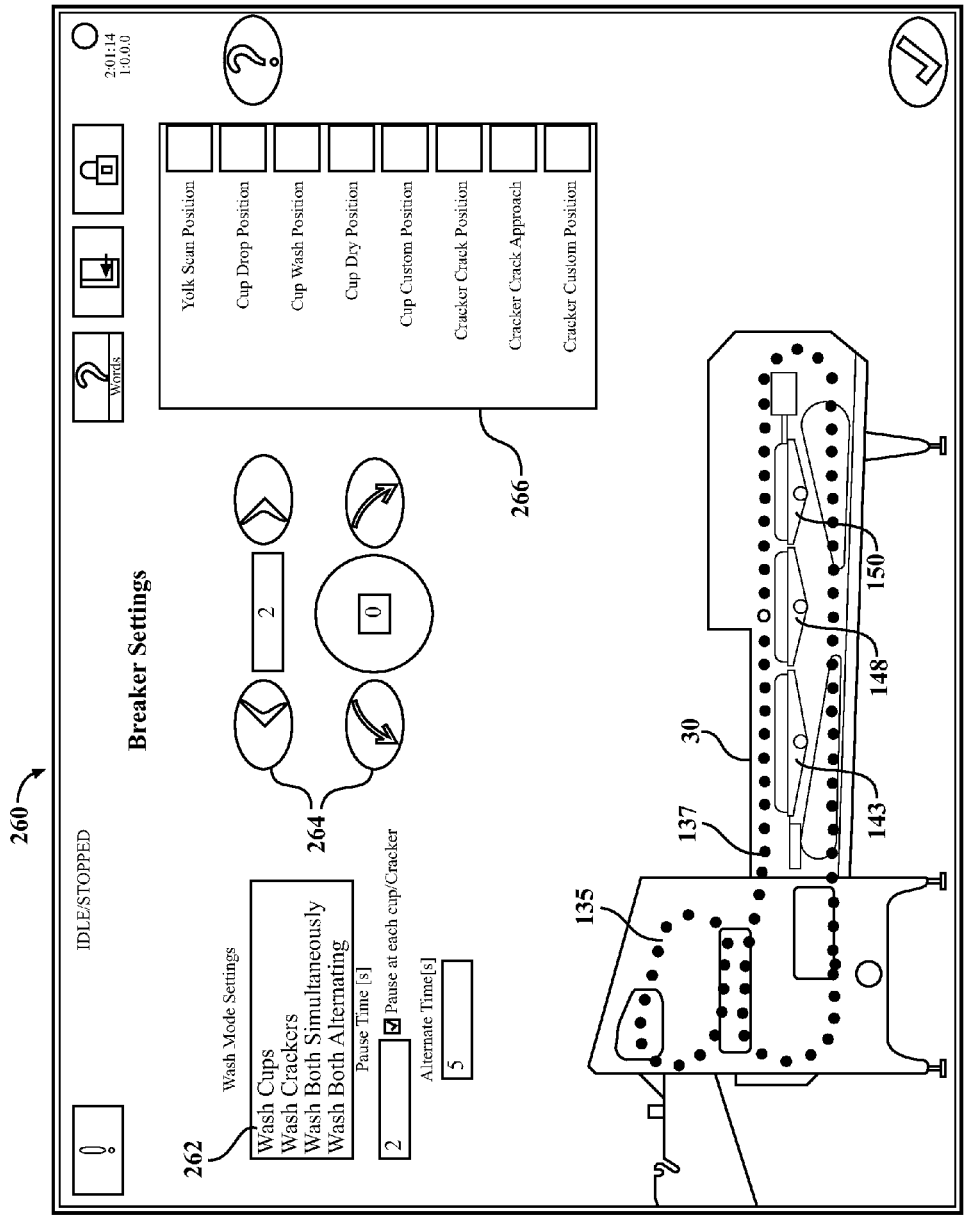
FIG. 28 is a control screen used to configure locations of all key points of the egg breaker subassembly, as well as to configure how the breaker will operate during CIP wash mode, which allows the operator to specify cleaning of cups and crackers separately, alternatively or simultaneously, with the ability to stop and start the machine at every cup and cracker while CIP commences.

FIG. 28 (previously referenced in description of the breaker 30) again presents a control screen 260 used to configure locations of all key points of the egg breaker subassembly 30, as well as to configure how the breaker will operate during CIP wash mode (see wash mode setting window 262 including both pause and alternate timing adjustments). Screen 260 also includes breaker settings 264, which allows the operator to specify a number of parameters and positions (see field 266) covering yolk scan, cup drop/wash/dry, cup custom position, cracker (knife) crack position, crack approach and custom positions, this encompassing cleaning of cups and crackers separately, alternatively or simultaneously, with the ability to stop and start the machine at every cup and cracker while CIP commences.

Figure 29:
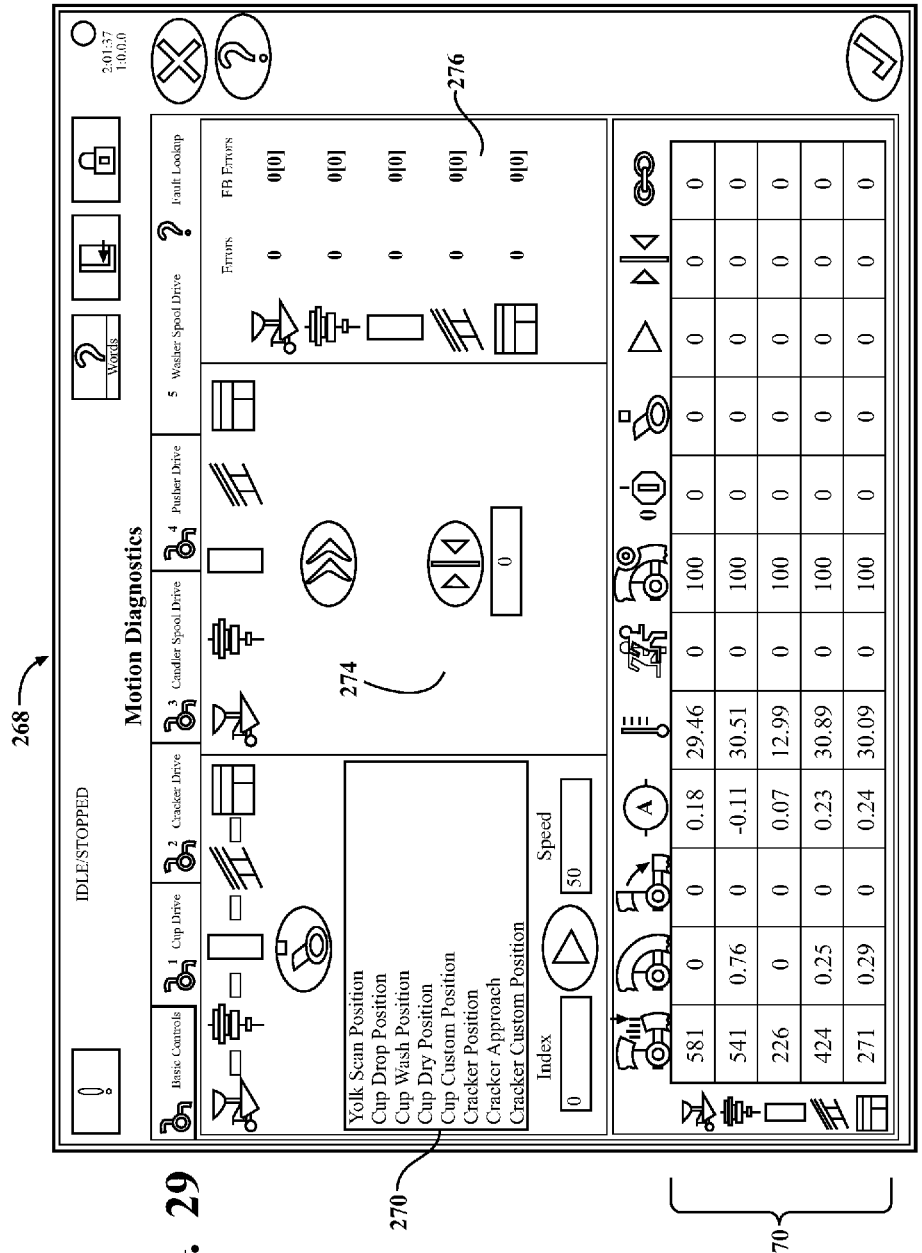
FIG. 29 is a control screen used to monitor servo motor parameters including position, speed, torque, electrical current, temperature, lag, and control states, while also allowing the operator to control servo motion manually by selectively moving one or more servo motors to a specific position, while holding a jog button, or by moving the entire machine to a specific position based on a cup or cracker bar index, the screen also providing servo motor fault information and fault code lookup tables, which can be accessed by clicking or touch pad accessing any error code shown.

Progressing to FIG. 29, control screen 268 is used to monitor servo motor parameters, collectively referenced by subfield 270, and including position, speed, torque, electrical current, temperature, lag, and control states, while also allowing the operator to control servo motion manually by selectively moving one or more servo motors to a specific position (see entry field 272), while holding a jog button, or by moving the entire machine to a specific position based on a cup or cracker bar index (field 274), the screen also providing servo motor fault information and fault code lookup tables (276), which can be accessed by clicking or touch pad accessing any error code shown.

Figure 30:
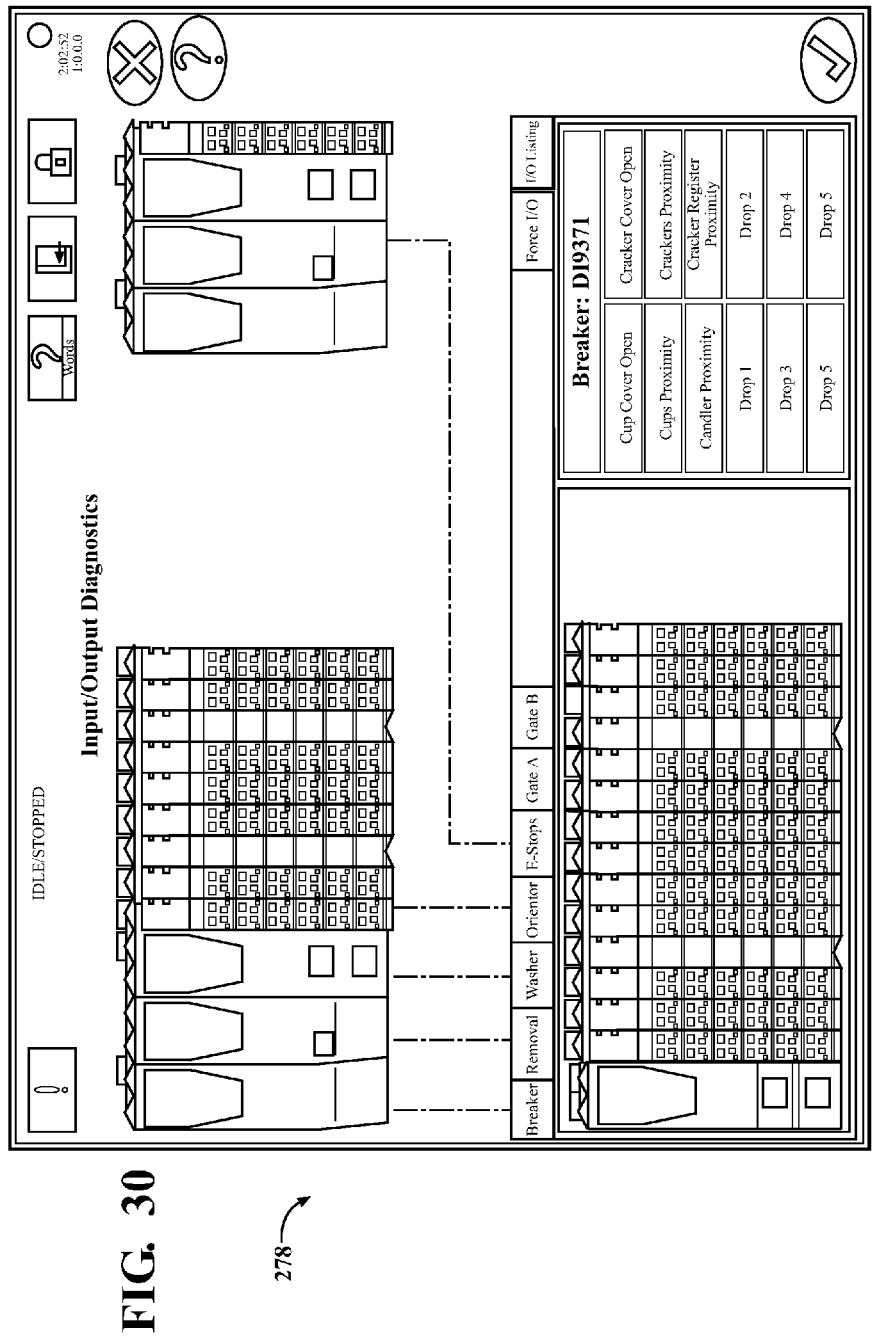
FIG. 30 is a control screen used for monitoring and controlling the machine I/O including the ability to monitor network link status, I/O module status, I/O point status, and complete E-stop circuit analysis, as well providing the ability to force non-safety related digital inputs and outputs on or off for diagnostics and testing.

FIG. 30 is a control screen 278 used for monitoring and controlling machine I/O (again input/output) diagnostics including the ability to monitor network link status, I/O module status, I/O point status, and complete E-stop circuit analysis, as well providing the ability to force non-safety related digital inputs and outputs on or off for diagnostics and testing. For purposes of clarity of illustration, a condensed depiction of the transfer system previously described is set forth and which also exhibits individual breaker condition information.

Figure 31:
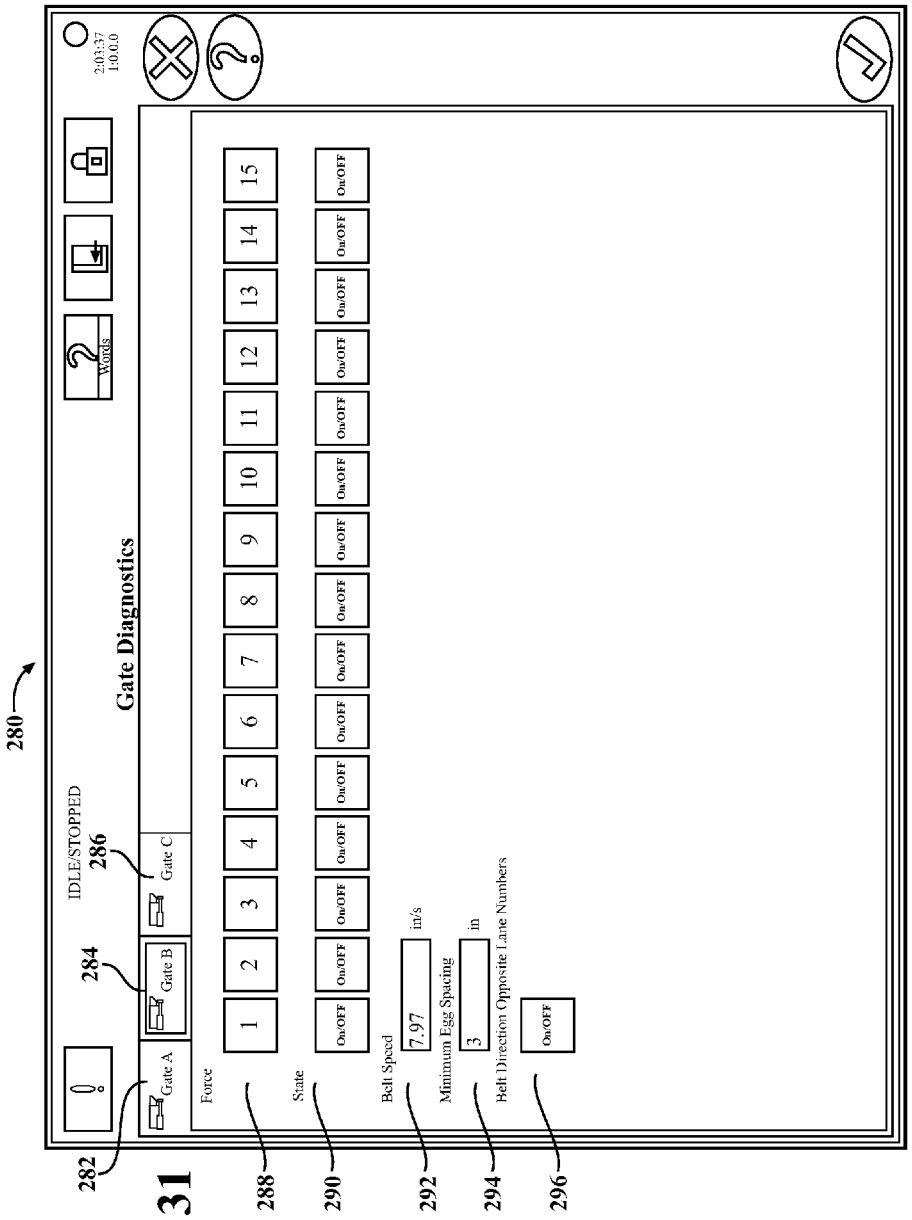
FIG. 31 is a control screen used to force manifold gate operation as well as provide configuration for high grade removal collision prevention, which helps prevent damaging high grade eggs by preventing removal if an egg is expected to land within the specified window of another high grade egg already removed.

FIG. 31 is a control screen 280 used to force manifold gate (again as previously described at 80, 82 and 84) operation as well as provide configuration for high grade removal collision prevention, which helps prevent damaging high grade eggs by preventing removal if an egg is expected to land within the specified window of another high grade egg already removed (reference also again being made to the gear defined widthwise opposing rotating brushes and conveyor drop configuration of FIGS. 10-12 previously described). Gates A, B, C are identified schematically at 282, 284, 286 corresponding to physical gates 80, 82, 84 with additional field callouts for lanes 1-15 (at 288), on/off state 290, belt speed 292, minimum egg spacing 294 and belt direction opposite lane numbers on/off 296.

Figure 32:
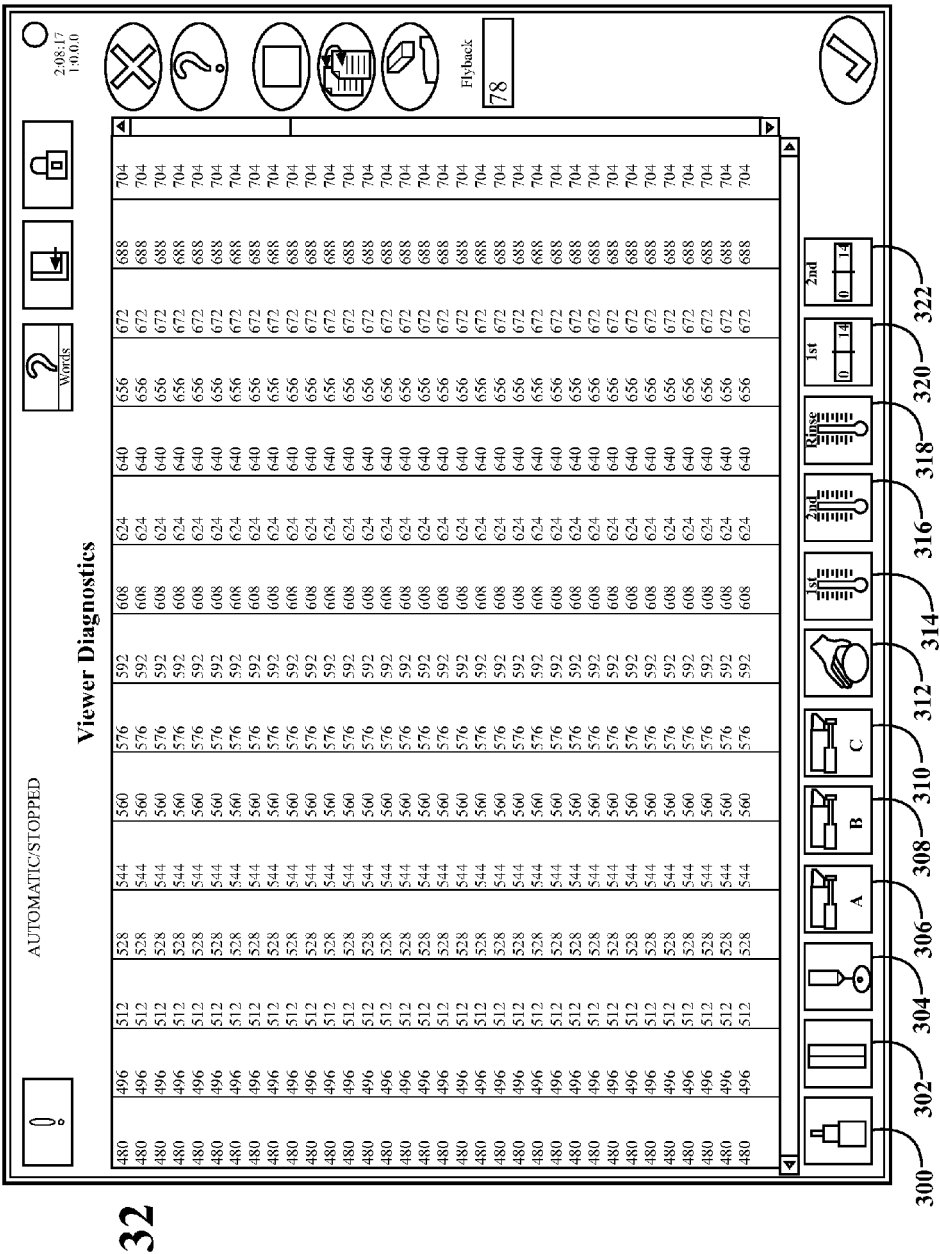
FIG. 32 is a control screen used to monitor real time operation of the machine including scale readouts, crack lane readouts (if applicable), dirt detector readouts, removal gate states, hand removal of eggs by Candler, wash temperatures, and wash pH values.

FIG. 32 is a control screen 298 used to monitor real time operation of the machine and including scale readouts 300, crack lane readouts 302 (if applicable), dirt detector readouts 304, removal gate states 306, 308, 310, hand removal of eggs by Candler 312, wash temperatures 314, 316, 318, and wash pH values (at 320 for first washer station and further at 322 for second washer station).

FIG. 33 is a control screen 324 display a log of preventative maintenance tasks loaded on a control computer in the form of site customizable spreadsheets, which allow the control software to inform operators of preventative maintenance tasks due and to track and log the completion of tasks as well as the operator completing the work and operator notes.

Figure 34:
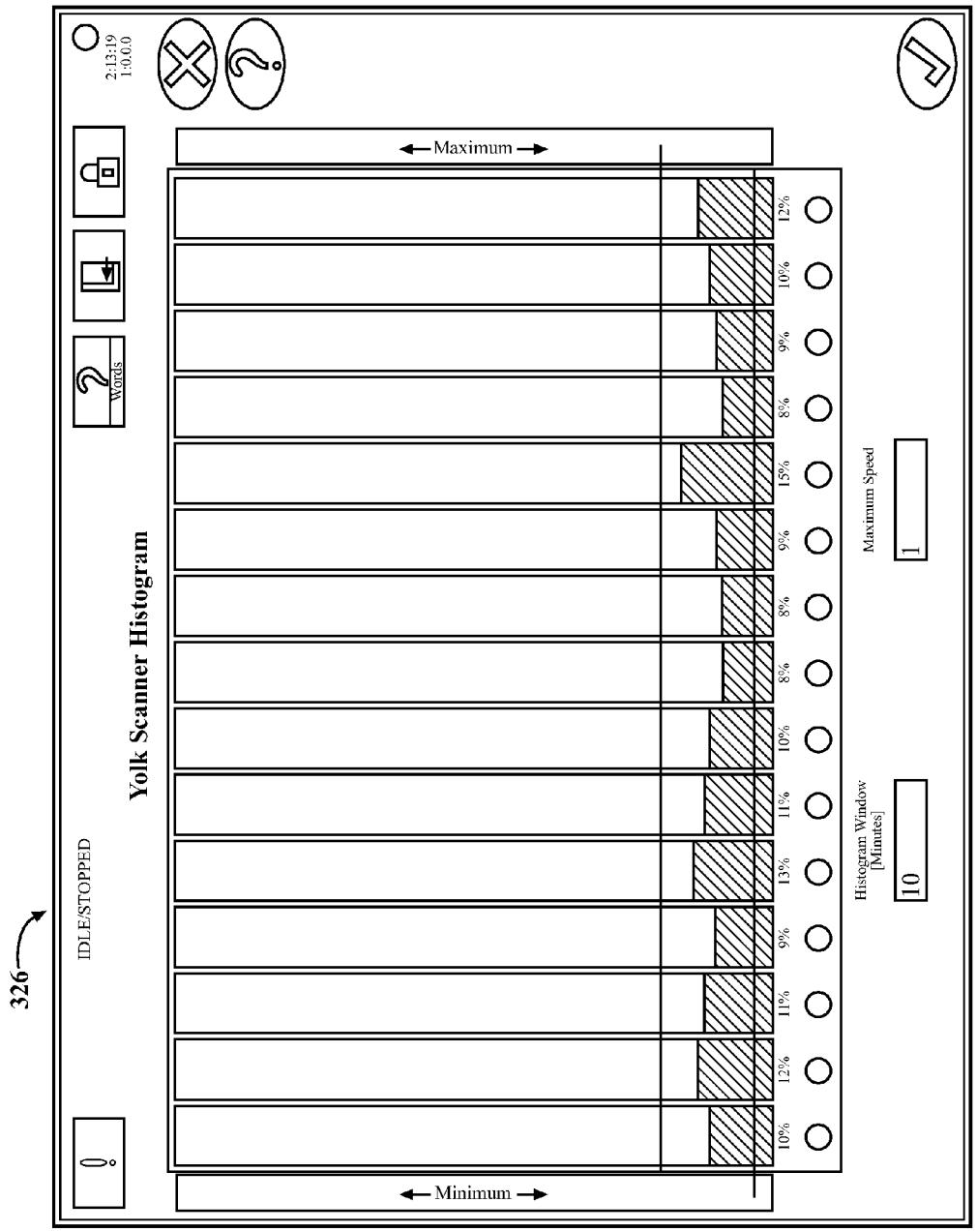
FIG. 34 is a control screen used to display a histogram of eggs rejected by the yolk scanner associated with the egg breaker subassembly and over a recent time period adjustable by the operator, as produced by a revolving list of histograms used to prevent counts from becoming too large to be useful in discovering problems defined by the operator as rates above or below set reject rates and a maximum difference between the upper and lower reject rate extremes.

FIG. 34 is a control screen 326 used to display a histogram of eggs rejected by the yolk scanner associated with the egg breaker subassembly over a recent time period adjustable by the operator, as produced by a revolving list of histograms used to prevent counts from becoming too large to be useful in discovering problems defined by the operator as rates above or below set reject rates, and a maximum difference between the upper and lower reject rate extremes.

Figure 35:
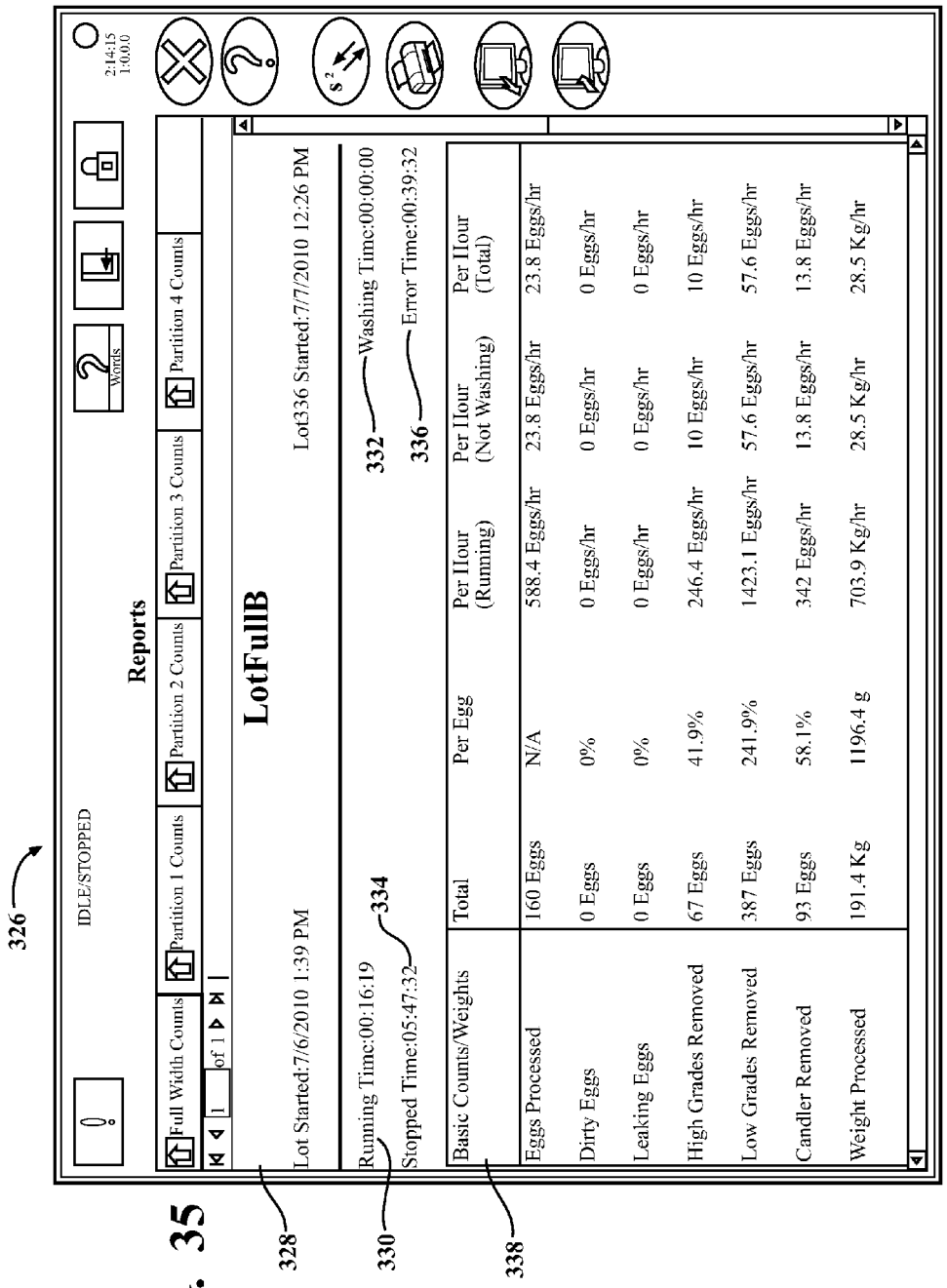
FIG. 35 is a control screen used to display, export and print reports of any partition of the machine including date pertaining to the lot start and stop dates and times, machine running time, machine washing time, machine break time, machine error time, egg counts, dirty egg counts, leaking egg counts, high-grade removal counts, low-grade removal counts, hand removal counts, total egg weight processed, low-grade weight removed, high-grade weight removed, hand removed weight, weight of egg sent to the breaker, cup wash count, cup reject count, average wash temperatures, average wash pH values, minimum wash temperatures, minimum wash pH values, maximum wash temperatures, maximum wash pH values, per egg rates, per hour rates for all of the listed as appropriate.

Progressing to FIG. 35, control screen 326 is used to display, export and print reports of any partition of the machine including date pertaining to the lot start and stop dates and times (see field 328), machine running time 330, machine washing time 332, machine break time 334, machine error time 336 and, as further collectively referenced by overall field 338, a series of individual included statistics for each of egg counts, dirty egg counts, leaking egg counts, high-grade removal counts, low-grade removal counts, hand removal counts, total egg weight processed, low-grade weight removed, high-grade weight removed, hand removed weight, weight of egg sent to the breaker, cup wash count, cup reject count, average wash temperatures, average wash pH values, minimum wash temperatures, minimum wash pH values, maximum wash temperatures, maximum wash pH values, per egg rates, per hour rates for all of the listed as appropriate.

Figure 36:
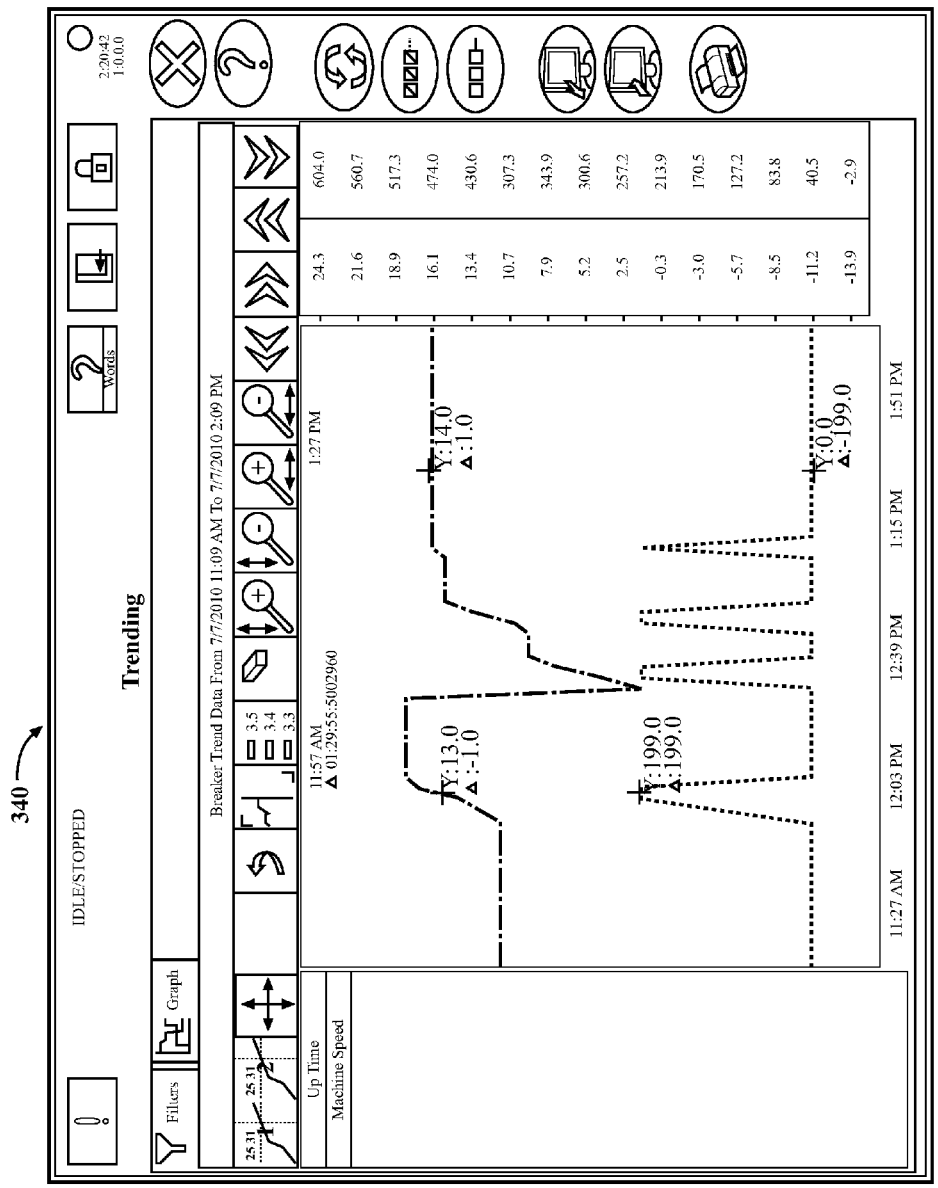
FIG. 36 is a control screen used to display, import and export trending data including running time, idle time, wash time, error time, machine speed, egg fill rate, processed egg count, high-grade egg count, low-grade egg count, hand removed egg count, cracked egg count, dirty egg count, leaking egg count, rejected cup count, washed cup count, weight processed, high-grade weight total, low-grade weight total, hand removed weight total, broken weight total, wash temperatures and wash pH values, the trend data being selected in any combination of those listed and zoomed and panned to the liking of the operator, as well as having cursors placed to get exact values and difference between samples.

Progressing to FIG. 36, control screen 340 is used to display, import and export trending data including (for ease of presentation without specific field callouts) each of running time, idle time, wash time, error time, machine speed, egg fill rate, processed egg count, high-grade egg count, low-grade egg count, hand removed egg count, cracked egg count, dirty egg count, leaking egg count, rejected cup count, washed cup count, weight processed, high-grade weight total, low-grade weight total, hand removed weight total, broken weight total, wash temperatures and wash pH values. Beyond that shown, the trend data is capable of being selected in any combination of those listed and zoomed and panned to the liking of the operator, as well as having cursors placed to get exact values and difference between samples.

Figure 37:
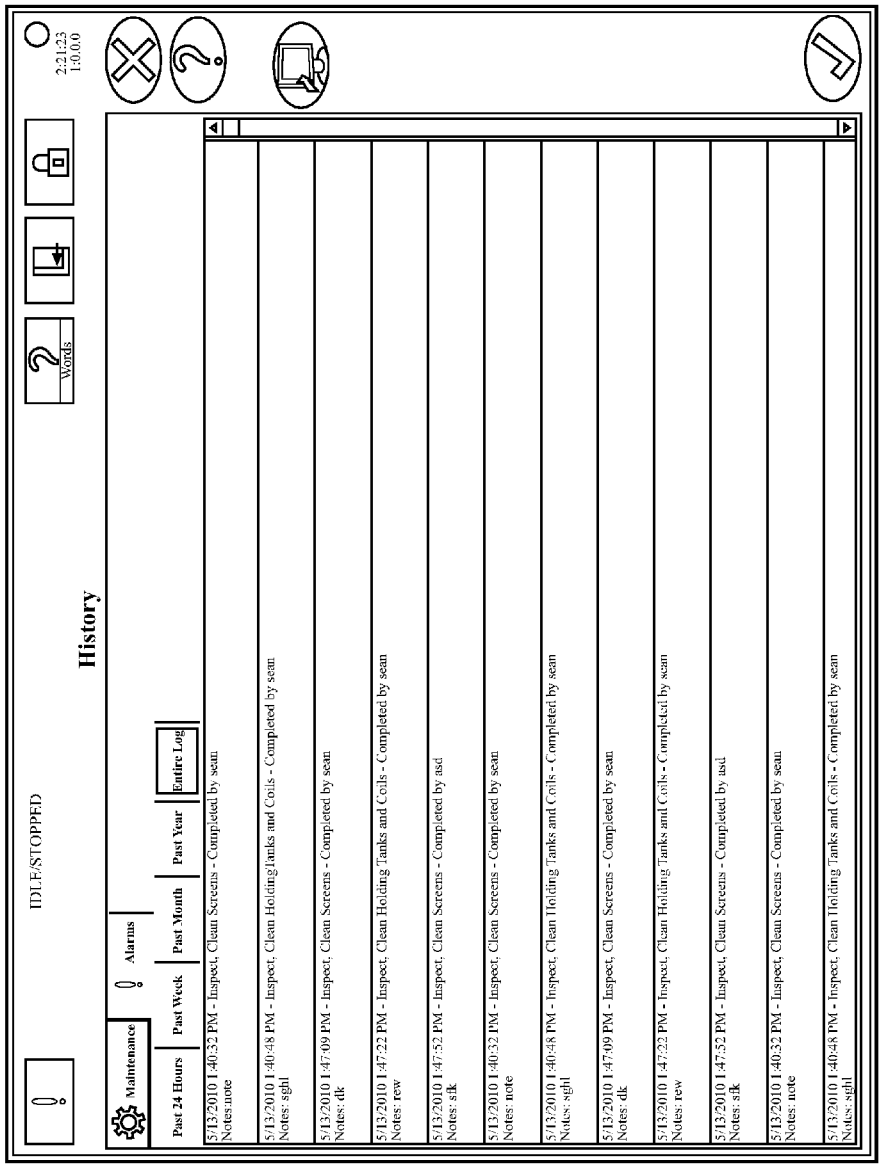
FIG. 37 is a control screen used to display and export logs of all preventative maintenance tasks completed in a given time period.
Figure 38:
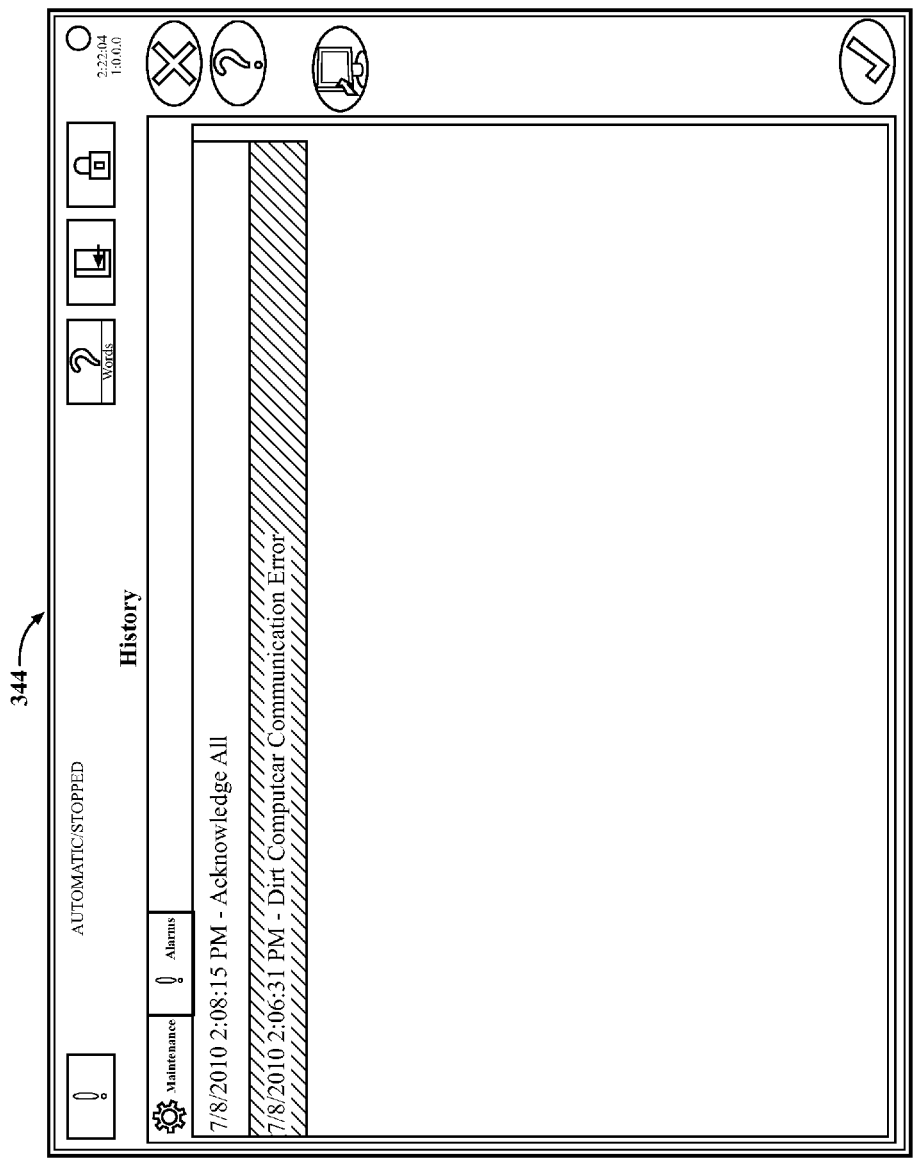
FIG. 38 is a control screen used to display and export a log of alarms and warnings, as well as self expiration of alarms and warnings and user acknowledgement of events.

FIG. 37 is a control screen 342 used to display and export logs of all preventative maintenance tasks completed in a given time period. FIG. 38 is a control screen 344 used to display and export a log of alarms and warnings, as well as self expiration of alarms and warnings and user acknowledgement of events.

Figure 39:
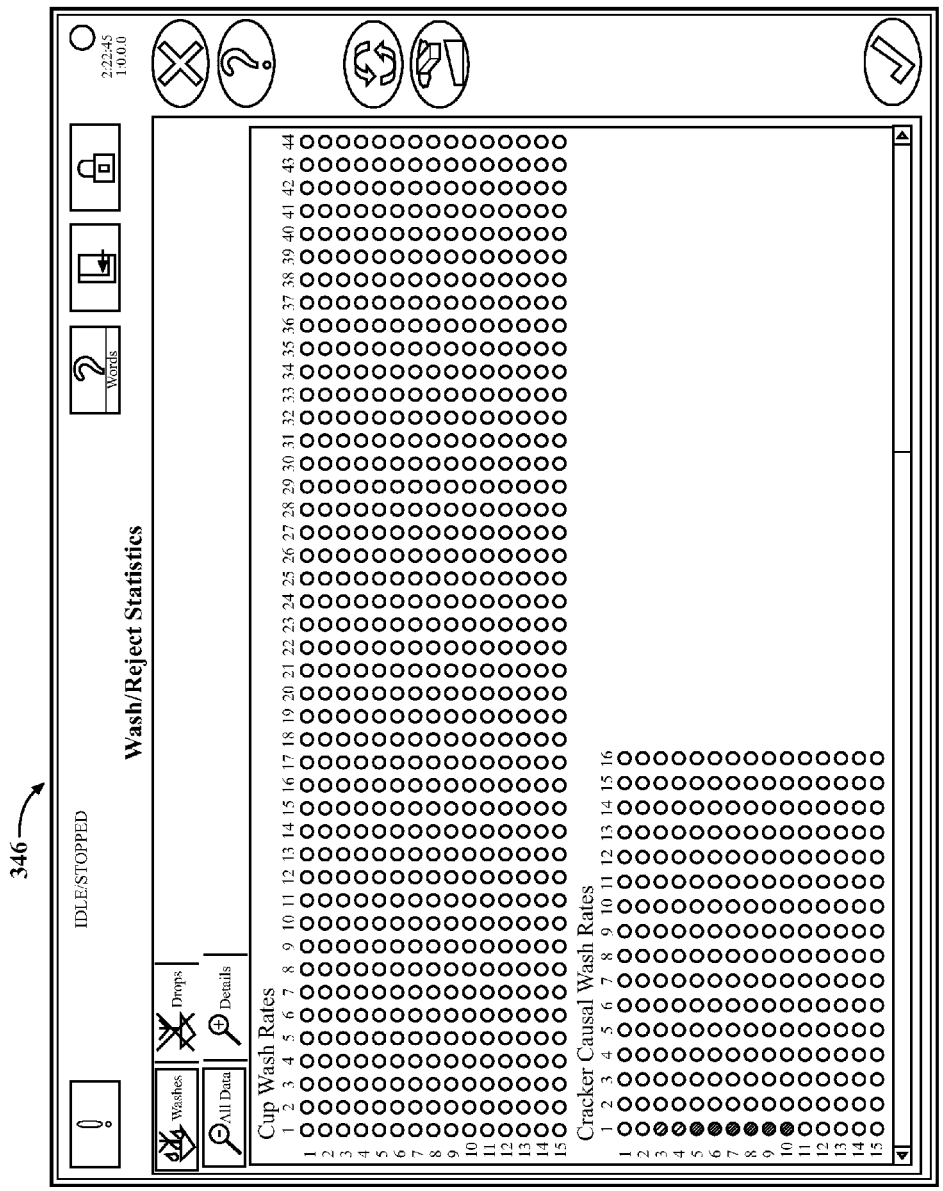
FIG. 39 is a control screen used to monitor the reject and wash rates for all cups and crackers on the breaker by displaying a color along the blue to red color gradient representing the rate, which can be viewed in detail by clicking any column of data.
Figure 40:
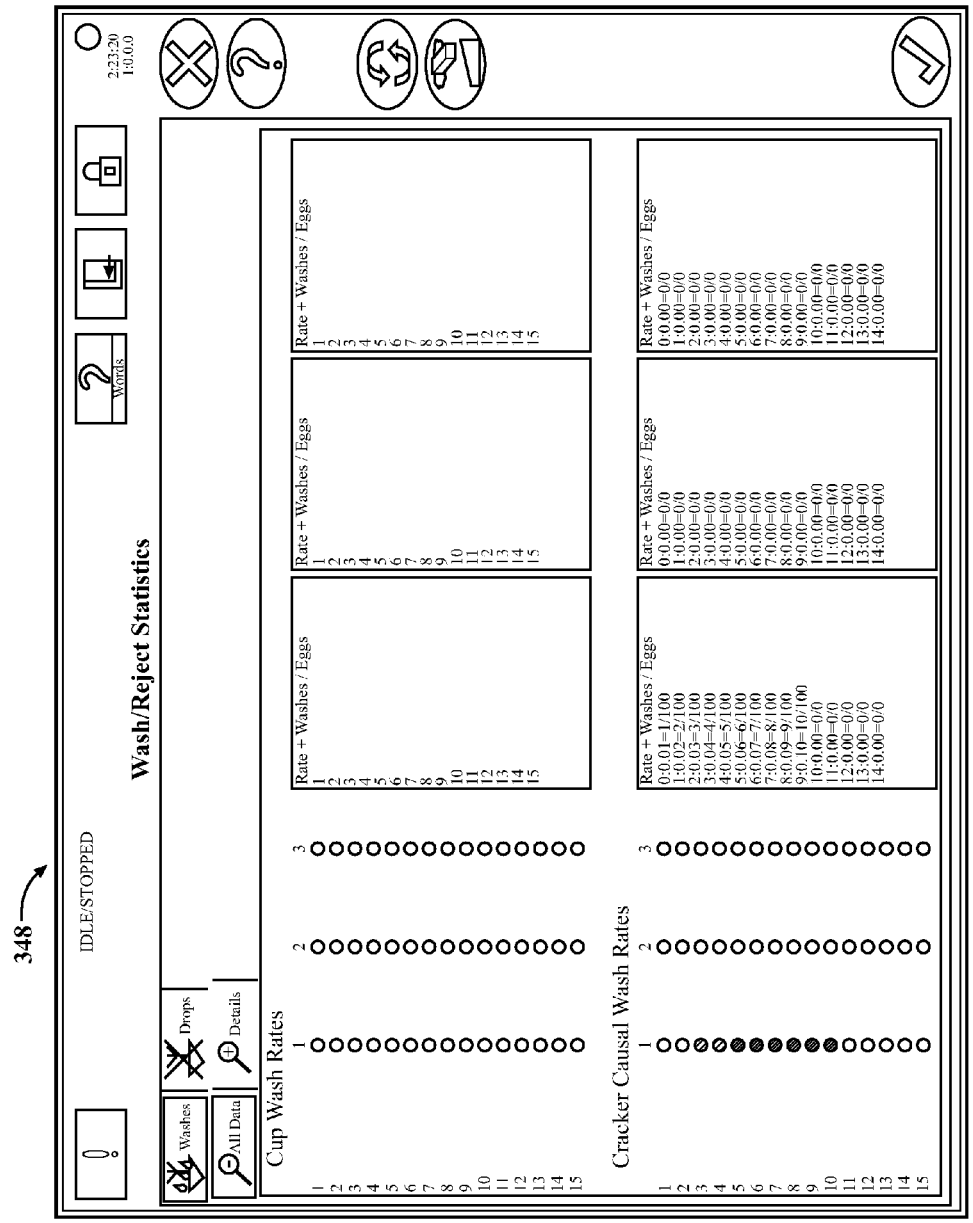
FIG. 40 is a control screen used to view details of cup and cracker wash rates or reject rates including a color representation and associated numerical representation.

FIG. 39 is a control screen 346 used to monitor the reject and wash rates for all cups and crackers on the breaker by displaying a color along the blue to red color gradient representing the rate, which can be viewed in detail by clicking any column of data. FIG. 40 is a control screen 348 used to view details of cup and cracker wash rates or reject rates including a color representation and associated numerical representation.

Figure 41:
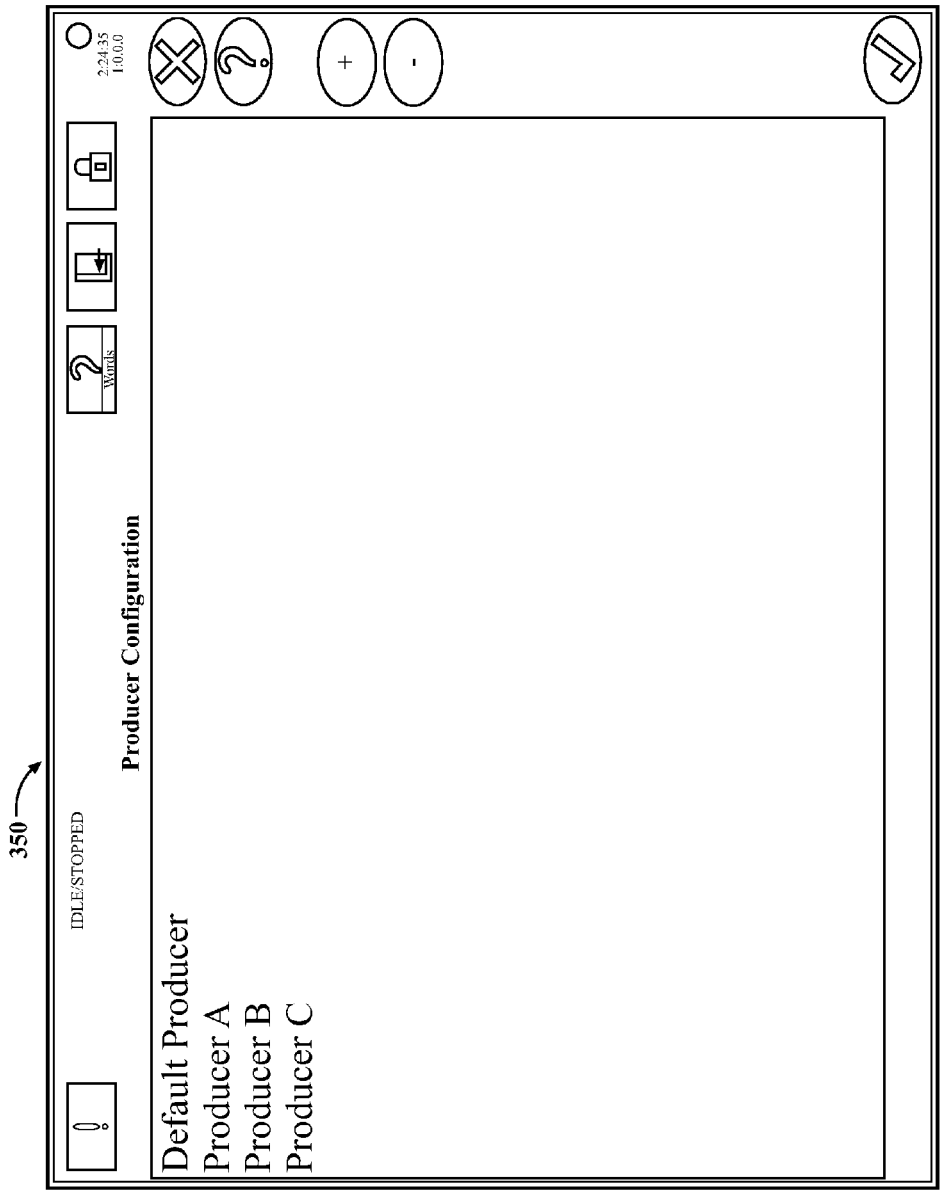
FIG. 41 is a control screen used to enter names of producers which are in turn available for assignment to partitions lots and reports.
Figure 42:
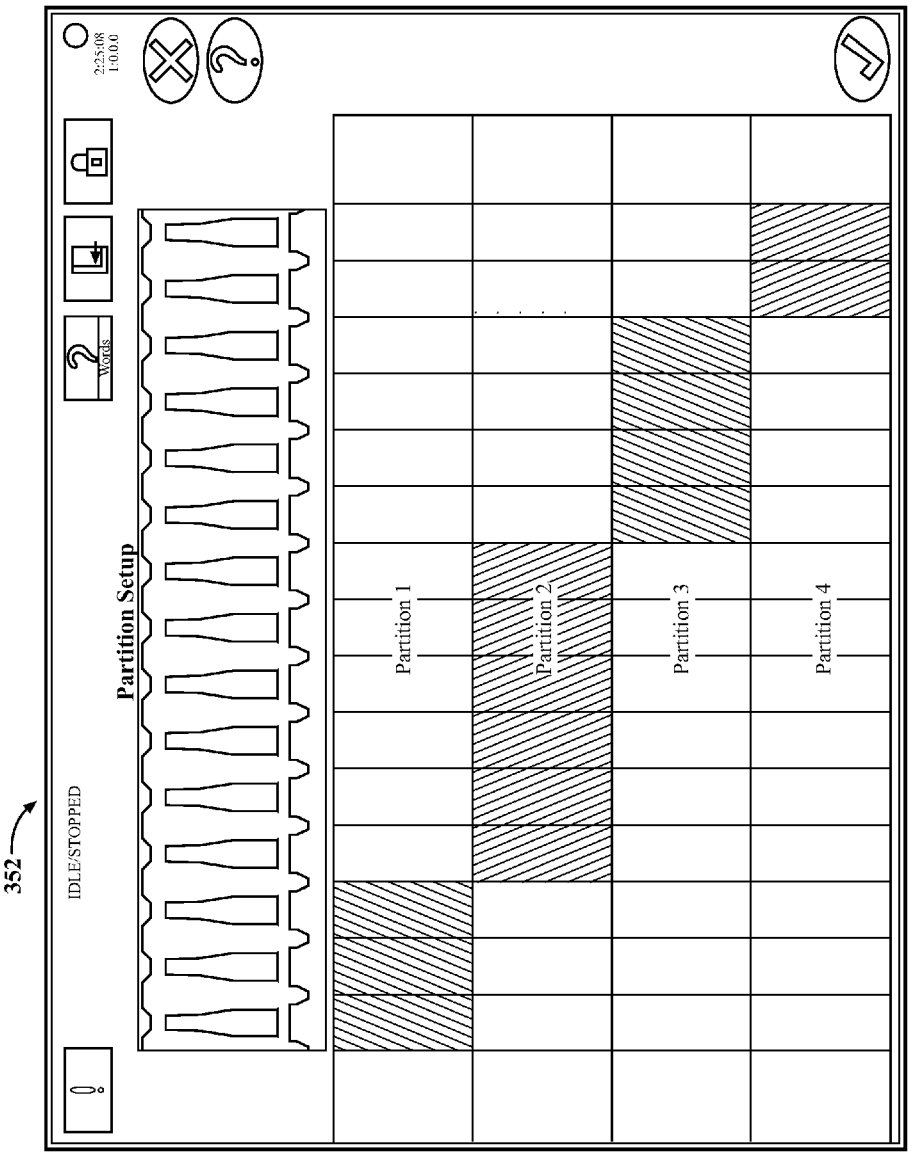
FIG. 42 is a control screen used to define partitions sizes and locations, which allows the control program to track data on each lane and associated data with the assigned partition.

Progressing to FIG. 41, control screen 350 is used to enter names of producers (such as corresponding to each of the individual laying houses previously identified at 14, 16 and 18) which are in turn available for assignment to partitions lots and reports. FIG. 42 is a control screen 352 used to define partitions sizes and locations, which allows the control program to track data on each lane and associated data with the assigned partition.

Figure 43:
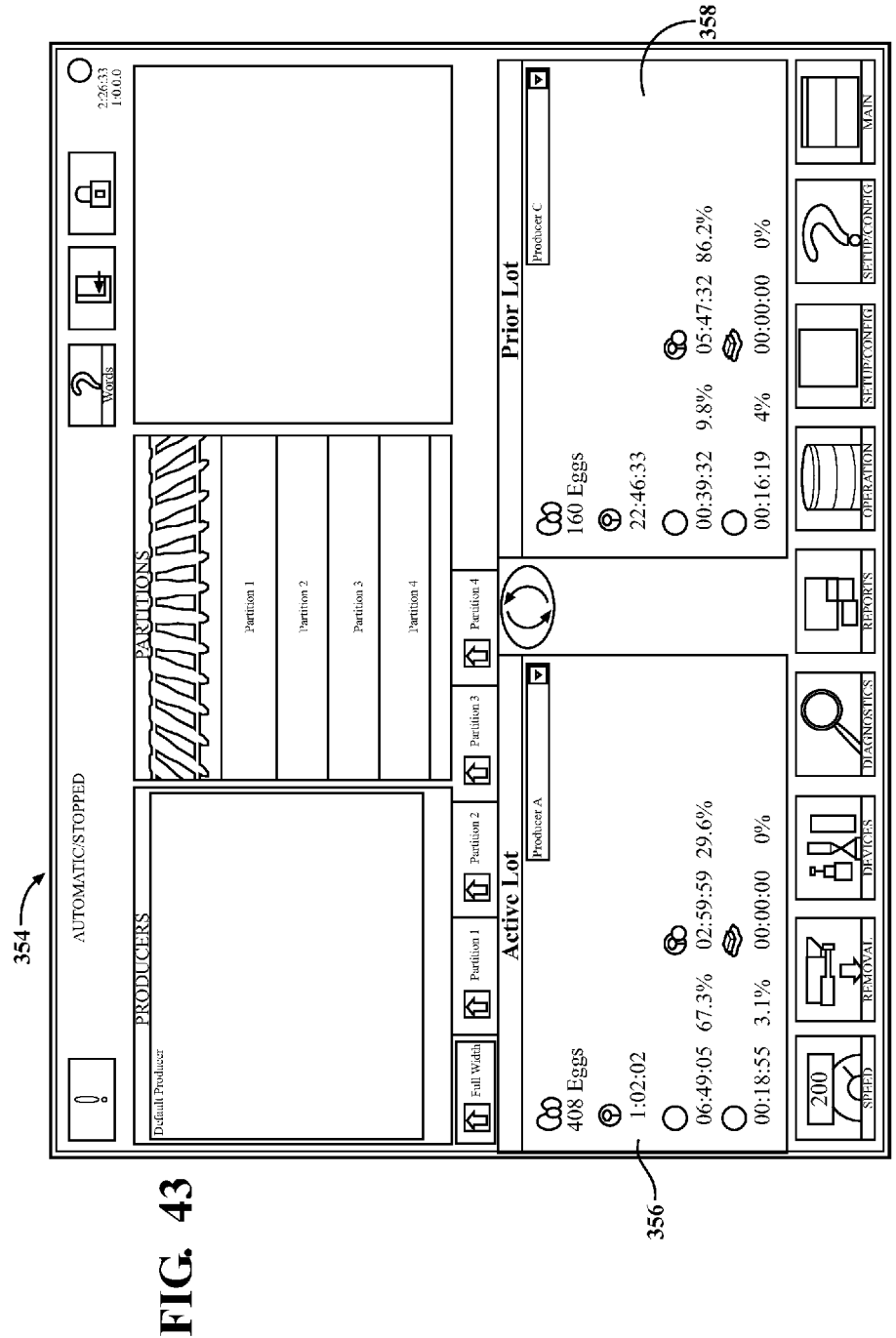
FIG. 43 is a control screen used to preview lot data for machine and defined partitions, and which includes an active lot where incoming data is placed as the machine operates, and a prior lot which contains a complete report of the last lot before an operator causes a lot swap, which will be written out to permanent storage on the next lot swap event.

FIG. 43 is a control screen 354 used to preview lot data for machine and defined partitions, and which includes an active lot 356 where incoming data is placed as the machine operates, and a prior lot 358 which contains a complete report of the last lot before an operator causes a lot swap, and typically which will be written out to permanent storage on the next lot swap event.

Figure 44:
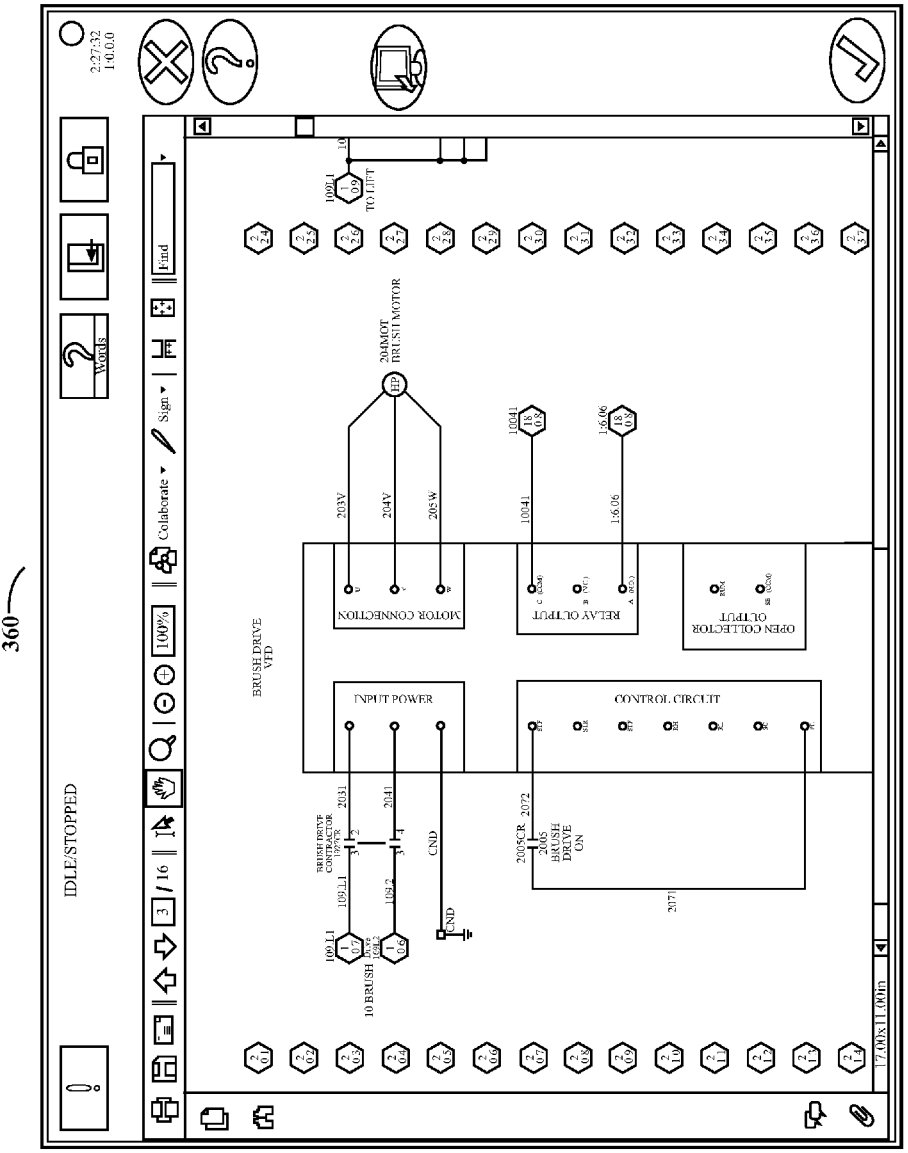
FIG. 44 is a control screen used to view and print documentation, schematic, and manual files installed on the machine, which can be fully customized on a site by site basis.
Figure 45:
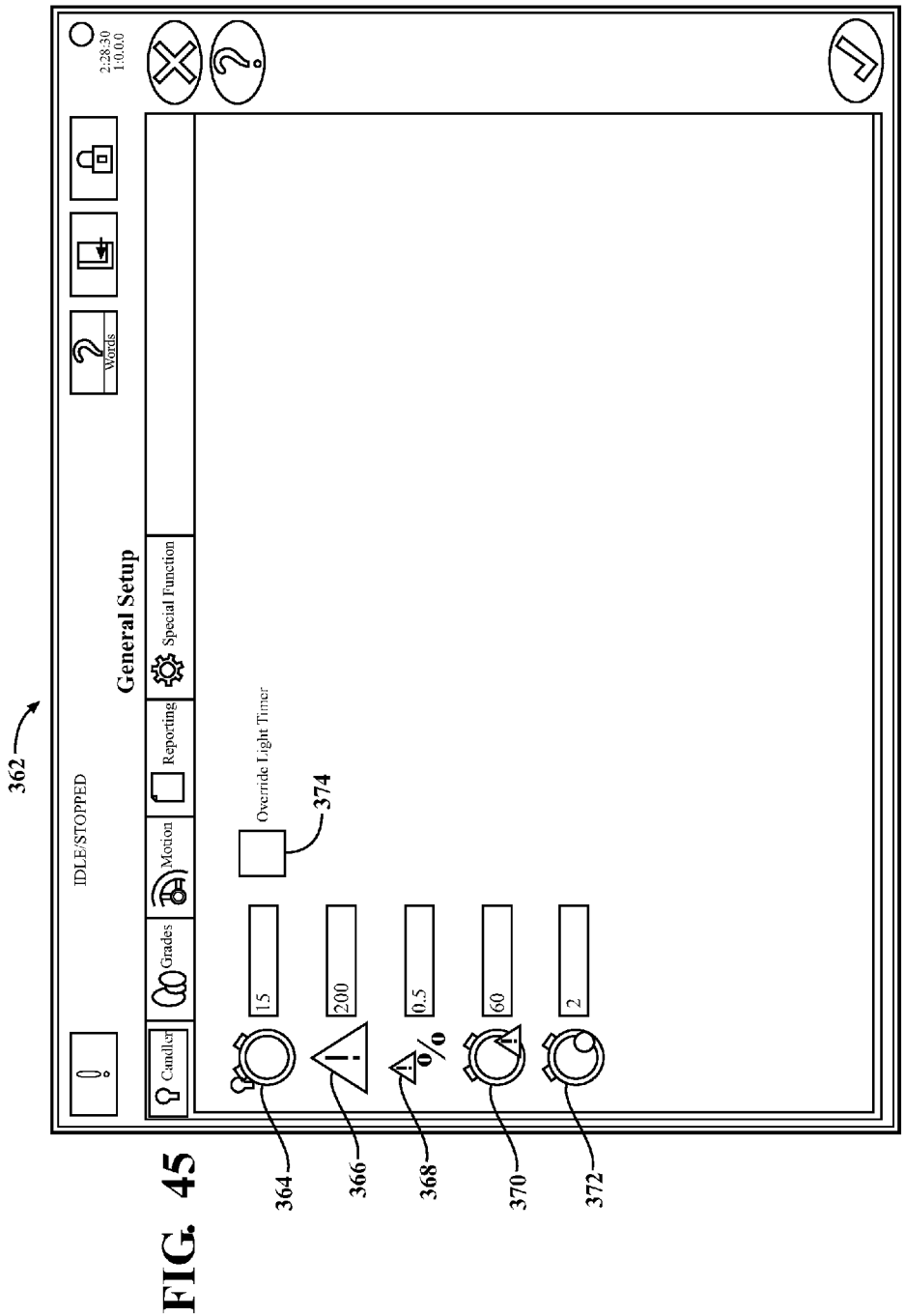
FIG. 45 is a control screen used to define a Candler operator station preferences including automatic shutoff time, maximum speed when slow button pressed, maximum speed percentage when slow button pressed, time slow button stays in effect after pressing, time slow button must be held to stop machine, and whether lights should be turned off automatically or solely operated at Candler station.

FIG. 44 is a control screen 360 used to view and print documentation, schematic, and manual files installed on the machine, which can be fully customized on a site by site basis. FIG. 45 is a control screen 362 used to define a Candler operator station preferences (see again 76 in FIG. 8) and including automatic shutoff time 364, maximum speed when slow button pressed 366, maximum speed percentage when slow button pressed 368, time slow button stays in effect after pressing 370, time slow button must be held to stop machine 372, and whether lights should be turned off automatically or solely operated at Candler station 374.

Figure 46:
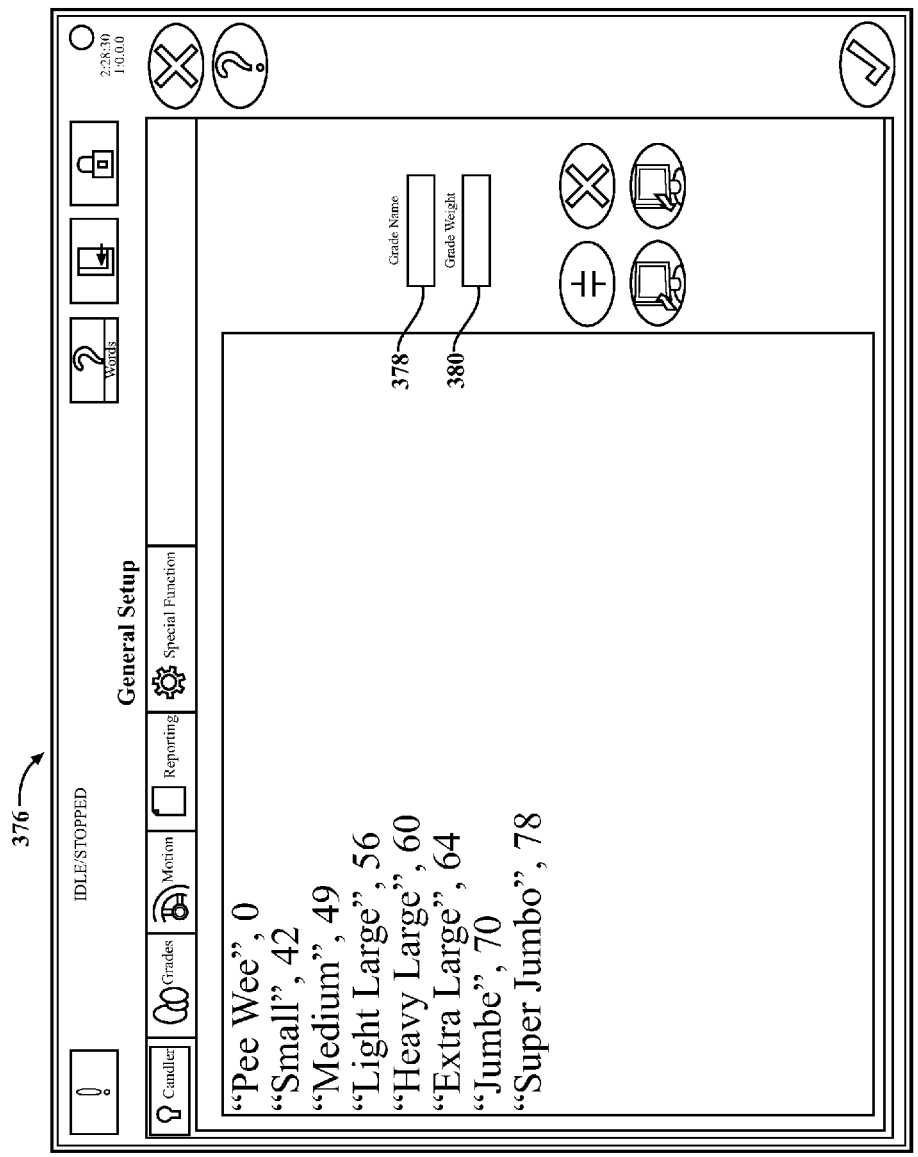
FIG. 46 is a control screen used to define egg grades used for determining if an egg qualifies for high-grade removal.
Figure 47:
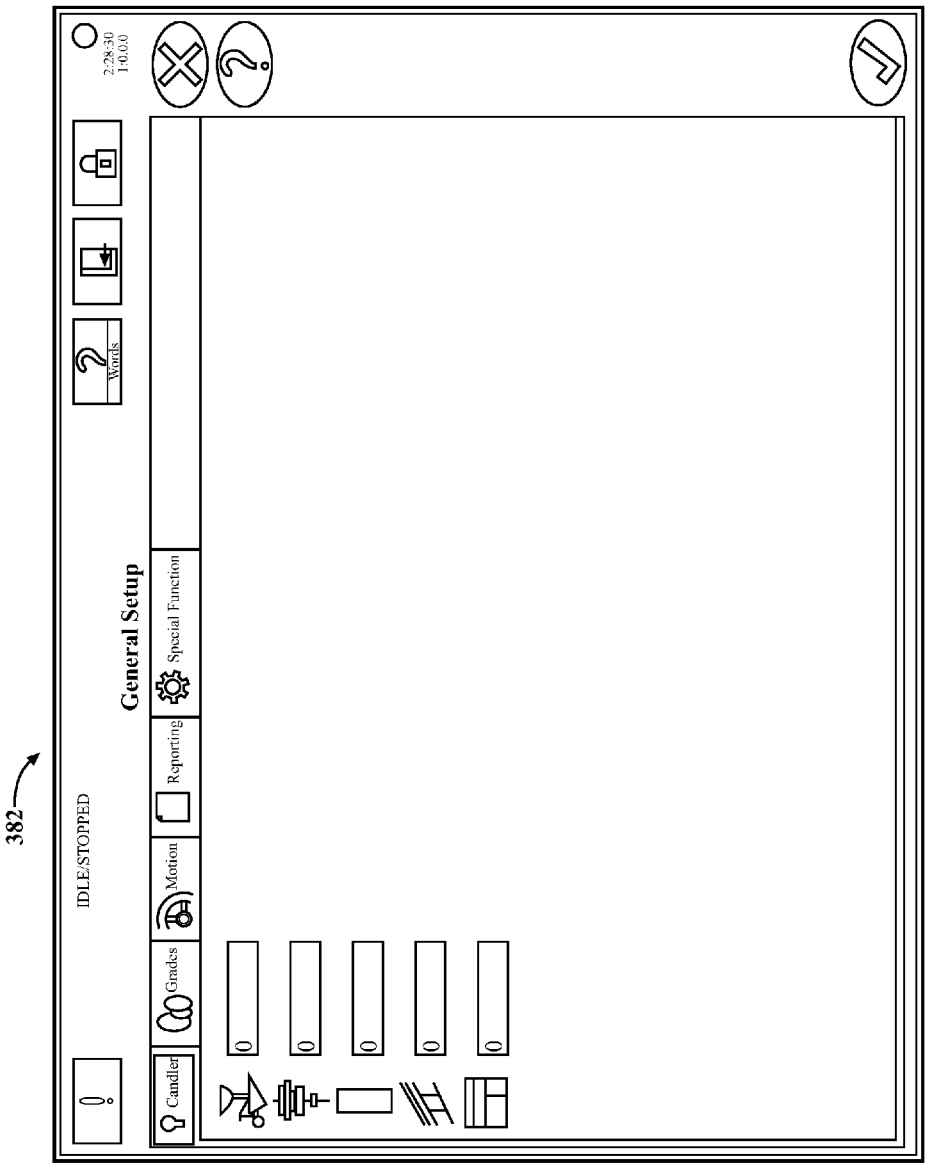
FIG. 47 is a control screen used to define offsets for servo home switches, which prevents any need for manually relocating switches to align machine components.

FIG. 46 is a control screen 376 used to define egg grades used for determining if an egg qualifies for high-grade removal, this screen also including grade name 378, grade weight 380 designation fields. FIG. 47 is a control screen 382 used to define offsets for servo home switches, which prevents any need for manually relocating switches to align machine components.

Figure 48:
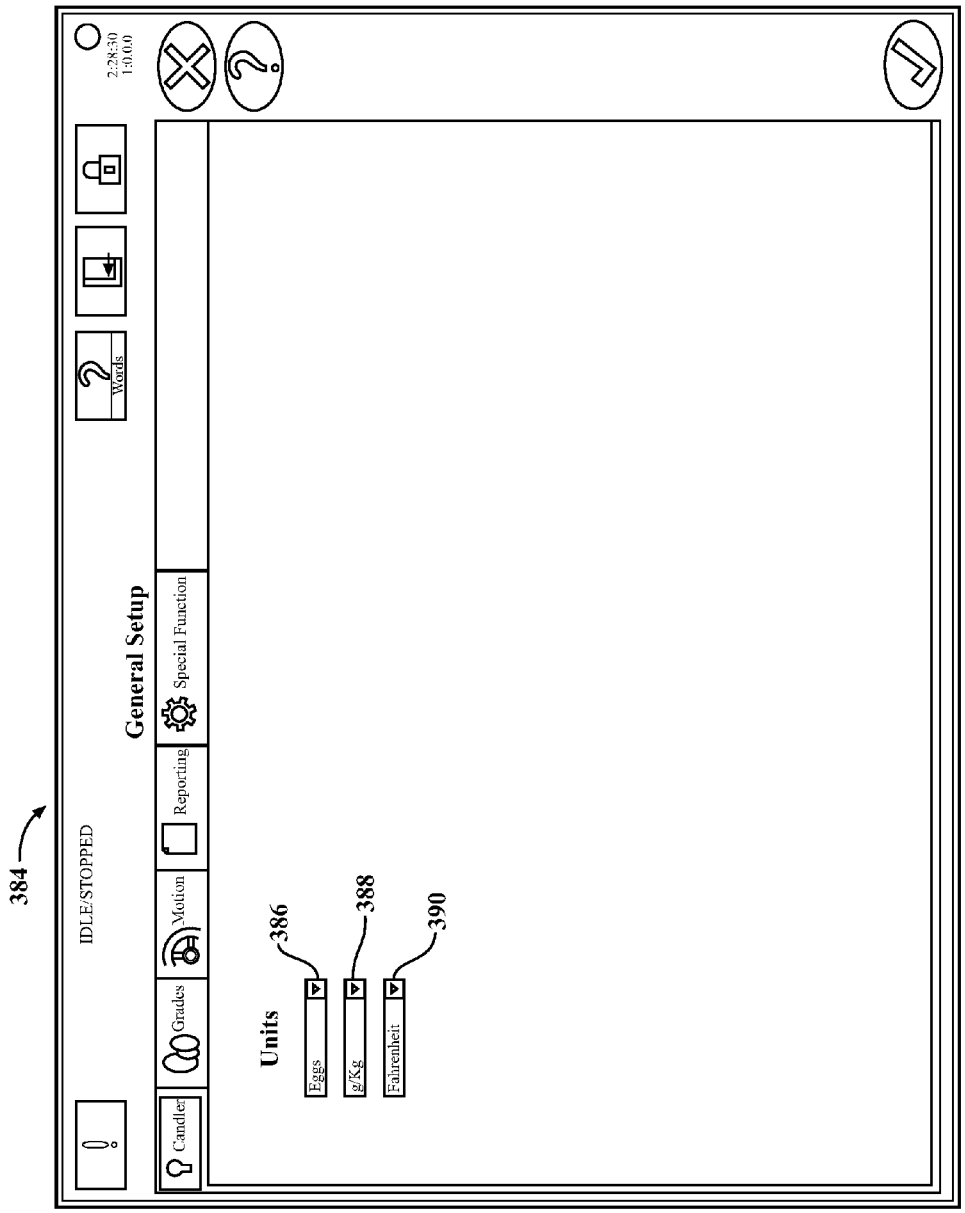
FIG. 48 is a control screen used to customize units displayed on reports and other control screens when reporting egg counts, weights, and temperatures.
Figure 49:
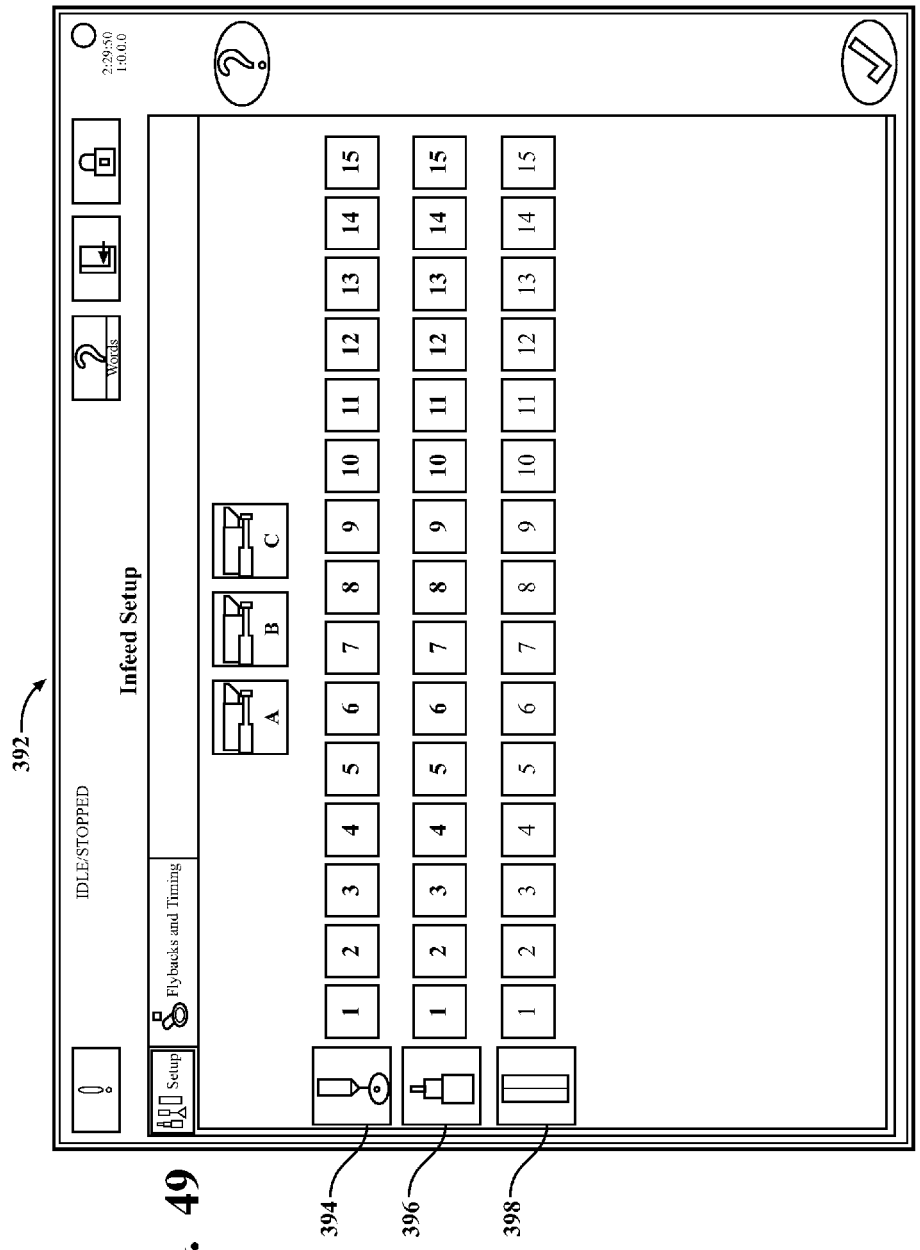
FIG. 49 is a control screen which provides access to specifying what gates, scales and crack lanes are installed, and the direction scales and crack lanes are wired as well as the orientation of the dirt detector camera system.

FIG. 48 is a control screen 384 used to customize units displayed on reports and other control screens when reporting egg counts 386, weights 388, and temperatures 390. FIG. 49 is a control screen 392 of an infeed setup and which provides access to specifying what gates 394, scales 396 and crack lanes 398 are installed, and the direction scales and crack lanes are wired as well as the orientation of the dirt detector camera system.

Figure 50:
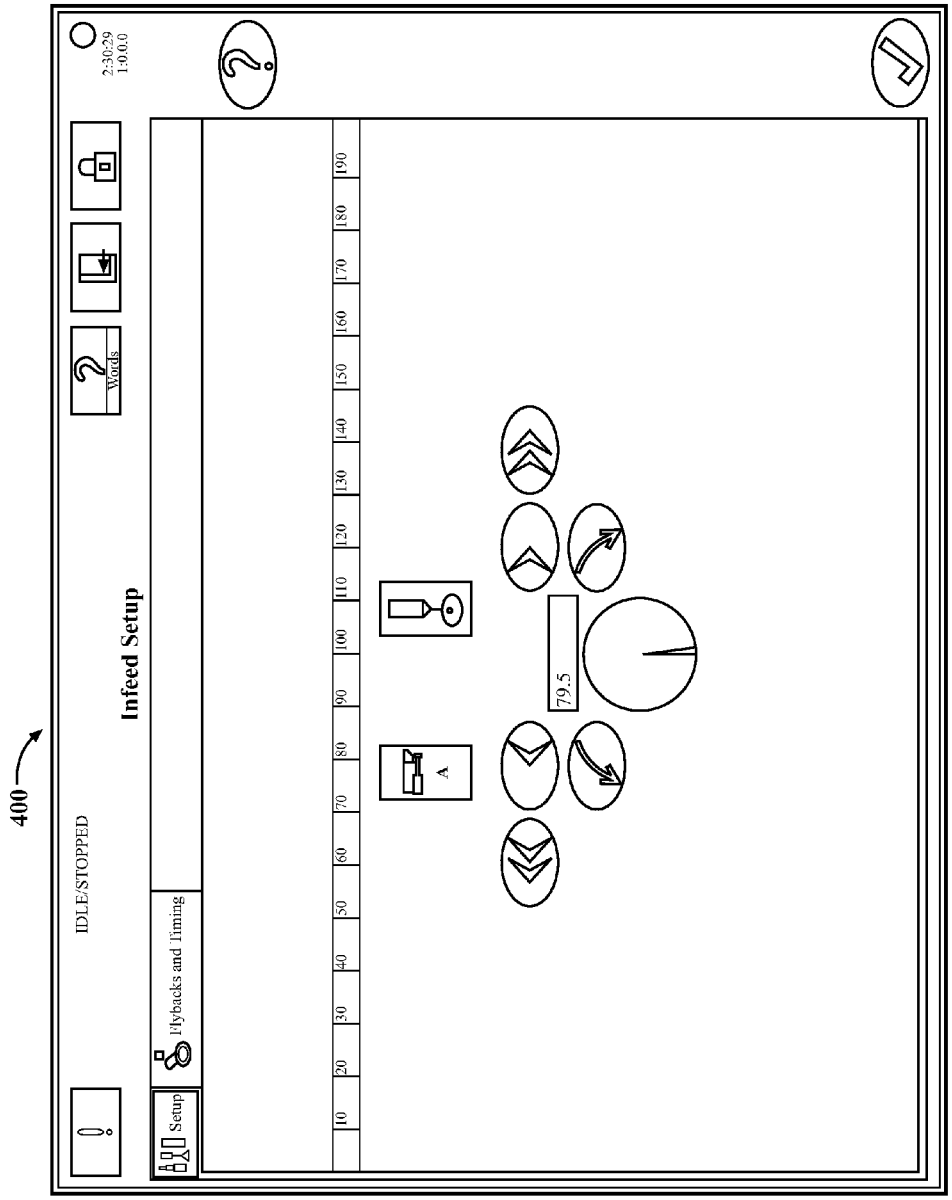
FIG. 50 is a control screen used to display and adjust the relative location of all devices installed on a scale of 0 (breaker infeed) and 500 (far outsize size of normal device layout)
Figure 51:
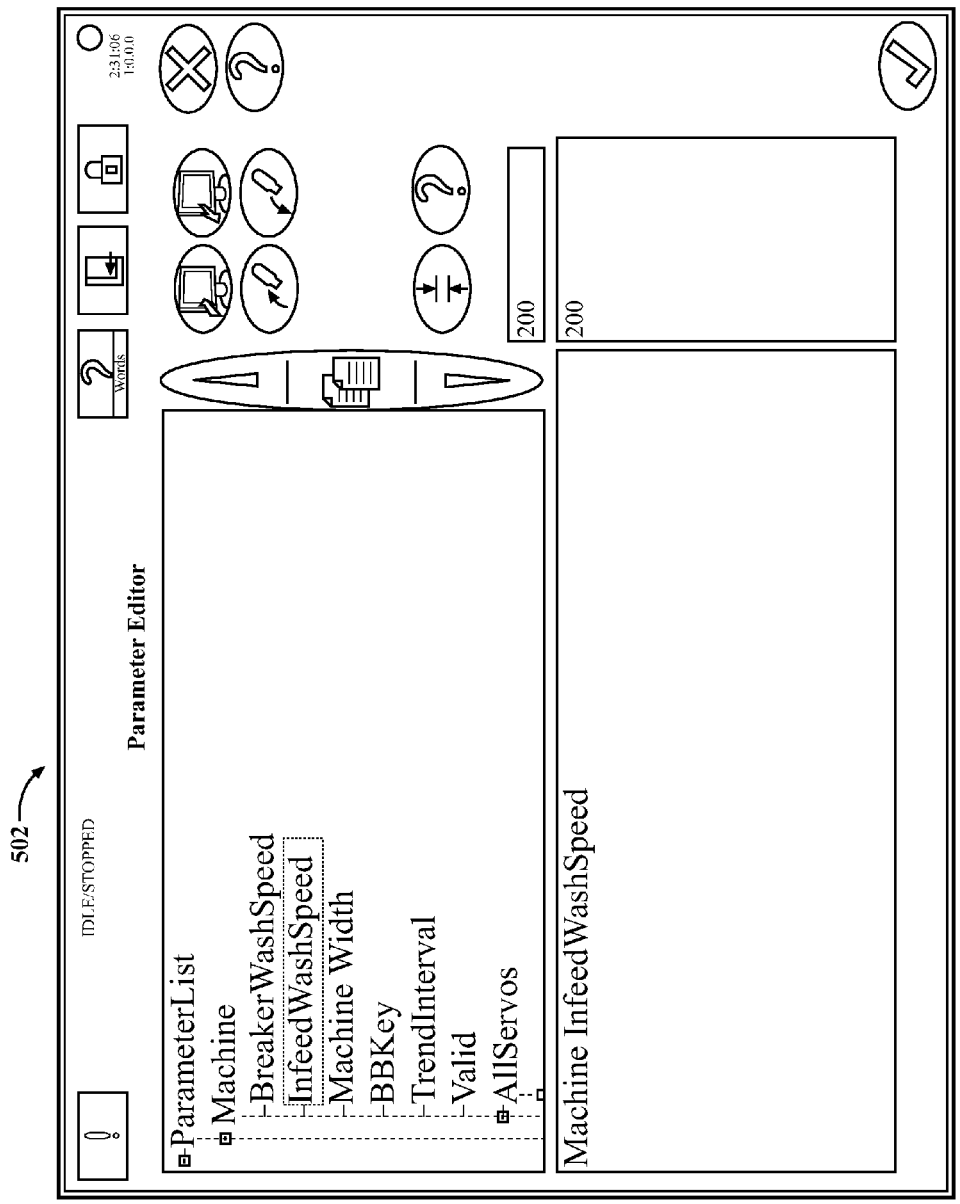
FIG. 51 a control screen used to load, save, look up documentation on, and edit all parameters in the control software including parameters not available on other control screens.

FIG. 50 is a control screen 400 used to display and adjust the relative location of all devices installed on a scale of 0 (breaker infeed) to 500 (far outsize size of normal device layout). Finally, FIG. 51 illustrates a last control screen 502 used to load, save, look up documentation on, and edit all of the parameters incorporated within the control software and including parameters not available on other control screens.

It is understood that the processor based system explained with reference to illustrations FIGS. 19-51 consists of only one possible depiction of a software based flow scheme for accomplishing multi-stage egg tracking, data gathering and disposition, and that the present invention also contemplates the inclusion of other processor controlling schemes, such as intended to aggregate egg related data between individual egg subassemblies or stations beginning with an accumulator and including any (but not necessarily each and every) of a washer, inspector/removal and breaker subassembly.

The processor control scheme as further depicted herein provides a number of advantageous features for assembling detailed, comprehensive and enduring records of each egg originating from an in-source location (such as again a laying house or other bulk feed supply) following through egg gate removal or egg breaking and reduction to yolk and albumen components. The multi-interfacing capabilities of the processor functionality further provides the ability to detect any negative trending of operation of any of the machine components (most notably but not limited to gate removal eggs and egg breakers) and which can allow for replacement or reconfiguration prior to resulting in any significant egg losses.

Having described my invention, other and additional preferred embodiments will become apparent to those skilled in the art to which it pertains, and without deviating from the scope of the appended claims.

I claim:

1. An egg transfer system for providing automated inspection and tracking of eggs, comprising:
   an inlet for receiving a volume of eggs, said inlet further including an egg accumulator;
   an egg inspection subassembly downstream from said inlet and including a number of inspection stations for determining various properties of each egg;
   an egg breaker subassembly interfacing with an outlet of said egg inspection subassembly;
   a processor communicating with each of said inlet and said inspection subassembly and compiling a data record of each egg including, at a minimum, positional information from said inlet and egg property information from said inspection subassembly;
   said processor providing an output communication to at least said inspection subassembly in order to instruct the removal, through at least one gate defined in said subassembly, of eggs within a parameter set by said processor and prior to said eggs advancing to said breaker subassembly; and
   a post breakage vision scanner in operative communication with said processor for determining at least yolk properties of each broken egg, said processor updating said data record.

2. The egg transfer system as described in claim 1, further comprising an egg washer subassembly interposed between said accumulator and said inspection subassembly.

3. The egg transfer system as described in claim 2, further comprising at least one conveying belt feeding the eggs to an inlet of said accumulator, said accumulator further comprising a plurality of individual lanes.

4. The egg transfer system as described in claim 2, said processor establishing at least one egg parameter through said washer subassembly and including at least one from the group selected from wash temperature, rinse temperature, conductivity, detergent level, time in wash and pH level.

5. The egg transfer system as described in claim 3, said egg property information compiled by said processor through said egg inspection subassembly further comprising sensor supplied data inputs from at least one of a vision inspection component for determining shell color and cleanliness and for determining shell cracking, a digital scale associated with each of said plurality of individual lanes for individually weighing each egg and a pre-breaker sensor located in proximity to each lane downstream from said digital scales for determining the presence or absence of an egg at a positional and advancing location originally identified at said accumulator.

6. The egg transfer system as described in claim 5, further comprising said processor grading and segregating the eggs into one of a number of classes for either removal or transfer to said breaker subassembly.

7. The egg transfer system as described in claim 6, said inspection assembly further comprising removal of desirable shell eggs through said gate for alternate applications other than being sent to said breaker subassembly for reduction of yolk and albumen components.

8. The egg transfer system as described in claim 6, said inspection subassembly further comprising a plurality of gates including a first gate for removing leaking or major defective eggs, a second gate for rerouting dirty eggs back to said washer subassembly and a third gate for rerouting desirable shell eggs for alternate applications other than being sent to said breaker subassembly for reduction of yolk and albumen components.

9. The egg transfer system as described in claim 1, said egg breaker subassembly further comprising a post breaker vision inspection unit for determining at least yolk properties of each egg.

10. The egg transfer system as described in claim 1, said egg breaker subassembly further comprising nozzles creating an air disturbance across a plurality of yolk cups and albumen trays in order to signal to an operator the existence of rotten egg products.

11. The egg transfer system as described in claim 2, said accumulator further comprising a plurality of lane dividers for segregating inputted eggs into dedicated lanes prior to delivery to a multi-row spool conveyor for delivery to and conveyance through said egg washer subassembly.

12. The egg transfer system as described in claim 11, further comprising a second spool section interconnecting said washer subassembly with said egg inspection subassembly.

13. The egg transfer system as described in claim 8, said processor further assigning a data packet to a location subsequent to said breaker subassembly holding a specified shell egg contents.

14. The egg transfer system as described in claim 10, further comprising a first manual removal station located at said candling station associated with said egg inspection subassembly and a second manual removal station located subsequent to said egg breaker subassembly.

15. A non-transitory computer writeable media incorporated into a processor for compiling and assembling a data file for each of a plurality of eggs conveyed through an egg transfer system and for instructing the system as to the handling and disposition of each egg, said processor comprising:
    a first subroutine for establishing the data file with positional information of an advancing egg at an inlet;
    a second subroutine for adding to each data file egg property information recorded from an inspection subassembly located downstream from the inlet;
    a third subroutine for communicating to at least the inspection subassembly in order to instruct the removal, through at least one gate, of eggs within a parameter set by said processor and prior to said eggs being advanced to an egg breaker; and
    a fourth subroutine post breaker for communicating with a vision inspection unit in operative communication with said processor for determining at least yolk properties of each egg and for updating said data file.

16. The computer writeable media as described in claim 15, further comprising a fifth subroutine for compiling additional information to each data file of each egg passing through a washer subassembly interposed between the inlet and inspection subassembly and including at least one from the group selected from wash temperature, rinse temperature, conductivity, detergent level, time in wash and pH level.

17. The computer writeable media as described in claim 15, said second subroutine further comprising providing sensor supplied data inputs from at least one of a vision inspection component for determining shell color and cleanliness and for determining shell cracking, a digital scale associated with each of a plurality of lanes for individually weighing each egg and a pre-breaker sensor located in proximity to each lane downstream from the digital scales for determining the presence or absence of an egg at a positional and advancing location originally identified at the inlet and prior to being forwarded to an egg breaker subassembly.

18. The computer writeable media as described in claim 17, further comprising a fifth subroutine succeeding said third subroutine for grading and segregating the eggs at the inspection subassembly into one of a number of classes for either removal or transfer to the breaker subassembly.

19. The computer writeable media as described in claim 18, said fifth subroutine further comprising said processor directing eggs to each of a plurality of gates including a first gate for removing leaking or major defective eggs, a second gate for rerouting dirty eggs back to the washer subassembly and a third gate for rerouting desirable shell eggs for alternate applications other than being sent to the breaker subassembly for reduction of yolk and albumen components.

20. An egg processing system incorporating data collection functionality for assembling a file pertaining to each of a plurality of eggs and determining, based upon the assembled file, a disposition of each egg, said system comprising:
    an accumulator inlet for receiving a volume of eggs;
    a washer subassembly for washing each of said eggs;
    an egg inspection subassembly downstream from said washer subassembly and including a number of inspection stations for determining various properties of each egg, said egg inspection subassembly further including a plurality of removal gates;
    a breaker subassembly succeeding said inspection and removal subassembly for reducing selected eggs to yolk and albumen components;

egg transfer subsystems including individual pluralities of spool bars interconnecting each of said accumulator, washer subassembly, inspection subassembly, and breaker subassembly;

a processor having a plurality of communication lines fed by sensors mounted at specified locations within each of said subassemblies and said interconnecting egg transfer subsystems, said processor progressively compiling a data record associated with an assigned and advancing egg position; and said processor providing an output communication to said inspection subassembly in order to instruct removal of defective eggs through a first selected one of said gates, a rerouting of dirty eggs to said washer subassembly via a second selected one of said gates and, removal of higher quality shell eggs as determined by the assembled data record of said processor for that advancing egg position through a third selected one of said gates and prior to a remaining quantity of eggs proceeding to said breaker subassembly.

* * * * *